US012274531B2

United States Patent
Harris et al.

(10) Patent No.: US 12,274,531 B2
(45) Date of Patent: Apr. 15, 2025

(54) OPTOACOUSTIC PROBE

(71) Applicant: Seno Medical Instruments, Inc., San Antonio, TX (US)

(72) Inventors: Jeffrey N. Harris, San Antonio, TX (US); Steven Solis, San Antonio, TX (US); Carlos Avila, San Antonio, TX (US); George Lamberson, San Antonio, TX (US)

(73) Assignee: SENO MEDICAL INSTRUMENTS, INC., San Antonio, TX (US)

( * ) Notice: Subject to any disclaimer, the term of this patent is extended or adjusted under 35 U.S.C. 154(b) by 1201 days.

(21) Appl. No.: 16/197,762

(22) Filed: Nov. 21, 2018

(65) Prior Publication Data

US 2019/0150749 A1  May 23, 2019

Related U.S. Application Data

(60) Provisional application No. 62/590,218, filed on Nov. 22, 2017.

(51) Int. Cl.
*A61B 5/00*     (2006.01)

(52) U.S. Cl.
CPC ........ *A61B 5/0095* (2013.01); *A61B 2562/12* (2013.01); *A61B 2562/16* (2013.01)

(58) Field of Classification Search
CPC .............. A61B 5/0095; A61B 2562/16; A61B 2562/12; A61B 2562/185; G01N 29/2418
See application file for complete search history.

(56) References Cited

U.S. PATENT DOCUMENTS

| 2014/0206978 | A1* | 7/2014 | Ackerman | ........... | A61B 8/4444 600/407 |
| 2014/0345385 | A1* | 11/2014 | Irisawa | ................ | A61B 8/4416 73/609 |
| 2015/0150433 | A1* | 6/2015 | Gazdzinski | .......... | A61B 1/0002 600/109 |

FOREIGN PATENT DOCUMENTS

WO    WO-2008089768 A1 *  7/2008   ......... A61B 5/14528

OTHER PUBLICATIONS

Yingchun Ding, Bing Xiao, Anisotropic elasticity, sound velocity and thermal conductivity of TiO2 polymorphs from first principles calculations, Computational Materials Science, https://doi.org/10.1016/j.commatsci.2013.09.061. (https://www.sciencedirect.com/science/article/pii/S092702561300596X) (Year: 2014).*

* cited by examiner

*Primary Examiner* — Yi-Shan A Yang
*Assistant Examiner* — Nicholas A Robinson
(74) *Attorney, Agent, or Firm* — Josef L. Hoffmann; The Small Patent Law Group LLC

(57) ABSTRACT

An optoacoustic probe for optoacoustic imaging of a tissue is provided. The probe has a distal end operable to contact the tissue and a proximal end. A transducer assembly is configured to receive optoacoustic return signals. An optical window is configured to carry light along a light path to the tissue. The housing comprises a distal portion that has a probe face that includes an acoustic opening into which the transducer assembly is disposed and an optical opening into which the optical window is disposed. The transducer assembly and the optical window extend proximally from the probe face. A gasket is disposed within the optical opening at the probe face and extends at least partially around the optical window. The gasket is configured to form an optoacoustic barrier to at least partially optically and (Continued)

acoustically isolate at least a portion of the optical window from the housing of the probe.

6 Claims, 12 Drawing Sheets

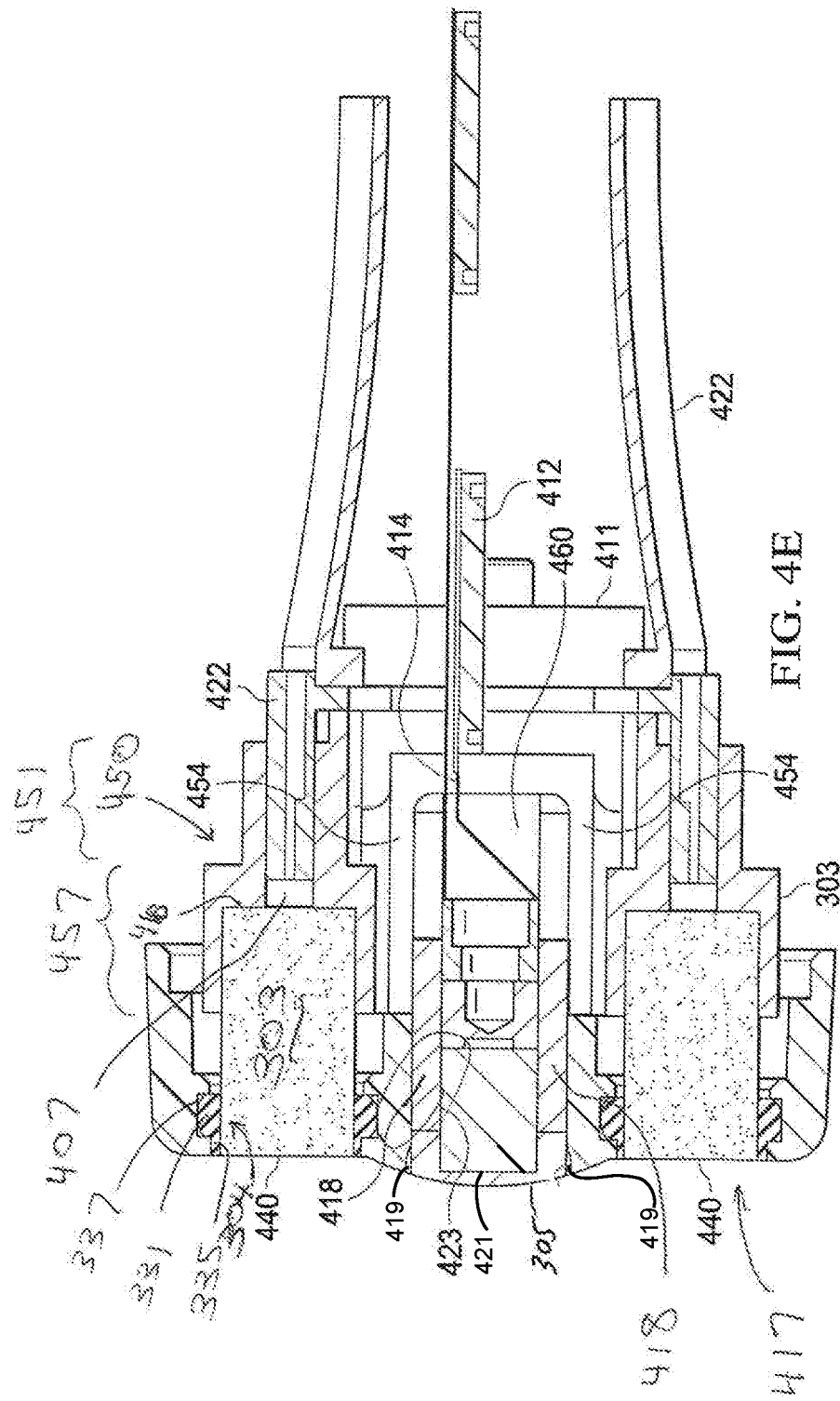

OPTOACOUSTIC PROBE

CROSS REFERENCE TO RELATED APPLICATIONS

This application claims benefit to U.S. Provisional Application No. 62/590,218, filed Nov. 22, 2017, titled "OPTOACOUSTIC PROBE", the subject matter of which is herein incorporated by reference in its entirety.

The present application relates to the following co-pending application: "PROBE WITH OPTOACOUSTIC ISOLATOR", Ser. No. 13/746,905, filed Jan. 22, 2013. The complete subject matter of the above identified co-pending application is expressly incorporated herein by reference in its entirety.

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

TECHNICAL FIELD

The present invention relates in general to the field of medical imaging, and in particular to a system relating to optoacoustic imaging.

BACKGROUND

Optoacoustic imaging systems visualize thin tissue slices noninvasively through skin at a tissue site. A tissue site may contain a variety of tissue structures that may include, for example, tumors, blood vessels, tissue layers, and components of blood. In optoacoustic imaging systems, light is used to deliver optical energy to a planer slice of the tissue site, which as a result of optical absorption with the tissue structures, produce acoustic waves. An image spatially representing the tissue site can be generated by performing image reconstruction on acoustic signals that return to an ultrasound transducer array. Because biological tissue scatters impinging optical energy in many directions the optical energy can be absorbed by tissue structures outside of a targeted region, which can generate acoustic return signals that interferes with the imaging of tissue structures within the targeted region.

Optoacoustic imaging systems have been proposed that seek to combine an acoustic transducer and optical transmitter in a common probe housing. However, convention optoacoustic (OA) probes exhibit certain limitations. The acoustic transducer is positioned adjacent to light path components, such as distal ends of a fiber array, a light guide and optical window. The light path components emit stray light rays at various points along the light path. The stray light rays create acoustic waves that are generated internally within the housing of the OA probe, and the internally generated acoustic waves are detected by the acoustic transducer as noise. The noise is introduced into the electrical signals output from the transducers.

Further, OA probes experience reflective optical signals. The reflective optical signals may cause heat to build up along the optical path, which may cause burning and degradation of optical components, such as the optical fibers, optical windows, and the like.

A need therefore exists for a more effective design for an OA probe that avoids undue generation of light induced noise in the acoustic signals.

BRIEF SUMMARY

New and useful systems, apparatuses, and methods for providing optoacoustic imaging are set forth in the appended claims. Illustrative embodiments are also provided to enable a person skilled in the art to make use the claimed subject matter.

Objectives, advantages, and a preferred mode of making and using the claimed subject matter may be understood best by reference to the accompanying drawings in conjunction with the following detailed description of illustrative embodiments.

In accordance with embodiments herein, an optoacoustic probe for optoacoustic imaging of a tissue is provided. The probe has a distal end operable to contact the tissue and a proximal end. A transducer assembly is configured to receive optoacoustic return signals. An optical window is configured to carry light along a light path to the tissue. The housing comprises a distal portion that has a probe face that includes an acoustic opening into which the transducer assembly is disposed and an optical opening into which the optical window is disposed. The transducer assembly and the optical window extend proximally from the probe face. A gasket is disposed within the optical opening at the probe face and extends at least partially around the optical window. The gasket is configured to form an optoacoustic barrier to at least partially optically and acoustically isolate at least a portion of the optical window from the housing of the probe.

Optionally, the transducer assembly may comprise an acoustic lens in acoustic communication with an acoustic transducer. The acoustic lens may have a distal face and a proximal end. The distal face may be adjacent the probe face and the proximal end may be adjacent the acoustic transducer. The gasket may be positioned between the optical window and the acoustic lens. The housing may be made from an optically reflective material that may comprise at least one of acrylonitrile-butadiene styrene or polybutylene terephthalate.

Optionally, the gasket may comprise a crystal structure having anisotropic thermal expansion properties that may form the optoacoustic barrier by constrain generation of acoustic waves from stray light within the gasket, thereby constraining propagation of acoustic waves from the gasket to the housing. The gasket may comprise silicone embedded with the crystalline structure. The crystalline structure may comprise at least one of i) titanium dioxide or ii) boron nitride, at a level of from 1% to 15% by weight of the gasket to provide the at least partial optical isolation. The gasket may comprise silicone embedded with microspheres at a level of from 2% to 25% by weight of the gasket to provide the at least partial acoustic isolation.

In accordance with embodiments herein, a method for assembling an optoacoustic probe is provided. The method comprises a housing having a probe face that defines an optical opening and an acoustic opening. The method inserts a transducer assembly into the acoustic opening and disposes a tubular gasket within the optical opening at the probe face such that the gasket extends at least partially around the optical opening. The method loads an optical window through the probe face into the gasket and the optical opening until a distal portion of the optical window is located proximate the probe face, such that the compressed gasket securely holds the distal portion of the optical window and configures the gasket as an optoacoustic barrier that at least partially optically and acoustically isolates the distal portion of the optical window from the housing of the probe.

Optionally, the housing may include a groove extending about the optical opening. The gasket may include a raised rib extending about a perimeter of the gasket and a flange extending along a distal edge of the gasket. The method may further comprise loading the gasket from the proximal end towards the distal end through the probe face by pulling on the flange until the rib is firmly seated within the groove. The method may shape the flange to be flush with the probe face. The transducer assembly may comprise an acoustic lens in acoustic communication with an acoustic transducer. The acoustic lens may have a distal face and a proximal end. The distal face may be adjacent the probe face and the proximal end may be adjacent the acoustic transducer. The gasket may be positioned between the optical window and the acoustic lens.

Optionally, the method may comprise forming the gasket to comprise a crystal structure having isotropic thermal expansion properties that may form the optoacoustic barrier by constrain generation of acoustic waves from stray light within the gasket, thereby constraining propagation of acoustic waves from the gasket to the housing. The crystal structure may be boron nitride. The gasket may further comprise a whitening material that may include TiO2 in addition to the crystal structure, at least one of the crystal structure and the whitening material creating optical scattering. The method may form the gasket from an elastomeric material that may be embedded with the crystalline structure and may form the crystalline structure from at least one of titanium dioxide or boron nitride at a level of from 1% to 15% by weight of the gasket to provide the at least partial optical isolation. The method may form the gasket from an elastomeric material that may be embedded with microspheres at a level of from 2% to 25% by weight of the gasket to provide the at least partial acoustic isolation.

In accordance with embodiments herein, an optoacoustic probe for optoacoustic imaging of a tissue is provided. The probe has a distal end operable to contact the tissue and a proximal end. The probe comprises a transducer assembly. A transducer is configured to receive optoacoustic return signals. An optical window is configured to carry light along a light path to the tissue. A housing comprises a distal portion that has a probe face that includes an acoustic opening into which the transducer assembly is disposed and an optical opening into which the optical window is disposed. The transducer assembly and the optical window extend proximally from the probe face. The transducer is held in the acoustic window. A transducer isolator is provided within the housing. The transducer isolator extends along one or both sides of the transducer between the transducer and the optical window. The transducer isolator is configured to provide an acoustic barrier between the transducer and the optical window.

Optionally, the transducer isolator may comprise a void that is air-filled. The transducer isolator may comprise an acoustic attenuating material. The acoustic attenuating material may comprises at least one of: neoprene rubber, a closed-cell foam or a polytetrafluoroethylene polymer.

In accordance with embodiments herein, an optoacoustic probe for optoacoustic imaging of a tissue is provided. The probe has a distal end operable to contact the tissue and a proximal end. A transducer assembly includes a transducer that is configured to receive optoacoustic return signals. An optical window is configured to carry light along a light path to the tissue. The housing comprises a probe face that includes an acoustic opening into which the transducer assembly is disposed and an optical opening into which the optical window is disposed. The transducer assembly and the optical window extend proximally from the probe face. An acoustic lens is provided over the transducer. The acoustic lens comprises a carrier material and an optoacoustic barrier material.

Optionally, the optoacoustic barrier material may comprise at least one of titanium dioxide, boron nitride, barium sulfate, aluminum dioxide, or combinations thereof. The optoacoustic barrier material may comprise boron nitride that may be present at a level from 1% to 10% by weight of the acoustic lens. The optoacoustic barrier material may comprise titanium dioxide that may be present at a level from 4% to 6% by weight of the acoustic lens. The carrier material of the acoustic lens may comprise room temperature vulcanized silicone. The acoustic lens may have a distal lens surface adjacent to the probe face. The distal lens surface may have a multi-layer coating comprising a transition metal tie layer distal to the distal lens face, a gold layer distal to the transition metal tie layer, and diamond-like carbon layer distal to the gold layer. The distal surface of the acoustic lens may be adjacent to a distal surface of the probe face, and the distal surface of the lens may comprise a coating comprising a polytetrafluoroethylene polymer. The acoustic lens may comprise an isolating material selected from the group consisting of titanium dioxide, boron nitride, barium sulfate, and mixtures thereof.

In accordance with embodiments herein, an optoacoustic probe for optoacoustic imaging of a tissue is provided. The probe has a distal end operable to contact the tissue and a proximal end. The probe comprises a transducer assembly, an optical window and a light path in optical communication with the optical window and a housing. The housing comprises a distal portion that has a probe face that includes an acoustic opening into which the transducer assembly is disposed and an optical opening into which the optical window is disposed. The transducer assembly and the optical window extend proximally from the probe face. A non-gassing (NG) support bracket defines a non-gassing optical transition zone located at an interface between the light path and a proximal end of the optical window. The NG support bracket is configured to avoid producing out gas in a presence of heat due to light emitted from the light path.

Optionally, the light path may comprise a light guide. The NG support bracket may include proximal and distal sections having a passage therethrough. The proximal section may be configured to receive at least a distal portion of the light guide. The distal section may be configured to receive and support a proximal portion of the optical window. The optical transition zone may be located at an intermediate point between the proximal and distal sections of the bracket. The light path may comprise an array of optical fibers that has a distal end adjacent to a proximal end of the light guide. The optical window may be configured to discharge a uniform energy distribution of no more than 20 mJ/cm$^2$. The optical transition zone may be an air void. The optical window may comprise a diffuser along the proximal end. The diffuser may have a holographic diffusing coating.

The probe for optoacoustic imaging of a tissue, may have a distal end operable to contact the tissue and a proximal end, which may comprise an acoustic element, an optical element, and a housing. The housing may comprise a probe face at the distal end of the probe, the probe face defining an acoustic element opening into which the acoustic element is disposed and an optical opening into which the optical element is disposed, the acoustic element and the optical element extending proximally from the probe face. The housing may also comprise a barrier member extending proximally from the probe face between at least a portion of the optical element and at least a portion of the acoustic element.

Optionally, the acoustic element of the optoacoustic probe may comprise an acoustic lens in acoustic communication with an acoustic transducer, the acoustic lens having a distal face and a proximal end, the distal face being adjacent the probe face, and the proximal end being adjacent being adjacent the acoustic transducer, wherein the barrier member is between the optical element and the acoustic lens. Optionally, the barrier member of the optoacoustic probe may be integral with the probe face. Optionally, the housing and the barrier member of the optoacoustic probe may be made from an optically reflective material, including acrylonitrile-butadiene styrene or polybutylene terephthalate. Optionally, the barrier member of the optoacoustic probe may comprise a receiver for the acoustic transducer. Optionally, the acoustic element of the optoacoustic probe may comprise an acoustic lens having a distal face, and the probe face comprises a rim defining the perimeter of the acoustic element opening and extending distally from the probe face, and the distal surface of the acoustic lens and the distal surface of the rim form a continuous surface.

Optionally, the optoacoustic probe may further comprise a gasket disposed between the optical opening and the barrier member, the tubular gasket having a distal end terminating at the probe face and a distal end, and having a flange at the distal end, wherein the optical element is disposed in the tubular gasket. Optionally, the housing of the optoacoustic probe may further comprise a first lateral member, a second lateral member and a third lateral member, the lateral members extending proximally from the probe face and configured with the barrier member to form a receiver for the tubular gasket, wherein the lateral members and the barrier member have a retaining feature into which the flange is disposed. Optionally, the tubular gasket of the optoacoustic probe may comprise an elastomeric material (e.g., RTV silicone), titanium dioxide at a level of from 4% to 6% by weight of the tubular gasket and/or boron nitride. Optionally, the tubular gasket of the optoacoustic probe may further comprise microspheres.

Optionally, the distal end of the barrier member, the distal end of the isolator, and the distal end of the acoustic transducer of the optoacoustic probe may form a convex surface on the probe face. Optionally, the barrier member and the acoustic element of the optoacoustic probe define a void between at least a portion of the optical element and at least a portion of the barrier member. Optionally, the void may be air-filled. Optionally, the acoustic element of the optoacoustic probe may comprise an acoustic lens in acoustic communication with an acoustic transducer, the acoustic lens having a distal face and a proximal end, the distal face being adjacent the probe face, and the proximal end being adjacent being adjacent the acoustic transducer, wherein the void is between the barrier member and the transducer. Optionally, the optoacoustic probe may further comprise an isolator disposed between the barrier member and the acoustic lens. Optionally, the acoustic isolator of the optoacoustic probe comprises an acoustic attenuating material comprises neoprene rubber. Optionally, the acoustic isolator of the optoacoustic probe comprises an acoustic attenuating material which comprises a closed-cell foam. Optionally, the optoacoustic probe may further comprise an isolator disposed between the acoustic element and the barrier member, the isolator comprising a tubular isolator member into which the acoustic transducer is disposed, the isolator comprising an acoustic attenuating material. Optionally, the acoustic attenuating material of the optoacoustic probe comprises neoprene rubber. Optionally, the resilient acoustic attenuating material of the optoacoustic probe may comprise a closed-cell foam or a polytetrafluoroethylene polymer. Optionally, the barrier member of the optoacoustic probe has a recess feature adjacent the probe face, and the isolator member has a flange disposed within the recess feature.

In an embodiment, a method for assembling an acoustic probe may comprise a housing having a probe face defining an optical opening and having a distal surface, a tubular gasket disposed in the optical opening, and an optical element disposed in the tubular gasket, wherein the tubular gasket has a proximal end and a distal end terminating at the probe face with a flange at the distal end, and the housing comprises a barrier member, a first lateral member, a second lateral member and a third lateral member, the barrier member and lateral members extending proximally from the probe face and configured to form a receiver for the tubular gasket, and wherein the lateral members and the barrier member have retaining features into which the flange is disposed and that are located at a first distance proximal from the probe face. The method may also comprise disposing an optical/gasket construct in the optical opening, the optical/gasket construct comprising a tubular member having a first end defining a flange and a second end such that the tubular member has a length longer than the first distance, wherein the optical element is disposed in the tubular member, the second end extends distally from the probe face, and the flange is proximal to the retaining feature; pulling the tubular member so that the tubular member moves distally within the receiver causing the flange to be received in the retaining feature; and cutting the tubular member to form the tubular gasket, such that the distal end of the tubular gasket and the distal surface of the probe face for a continuous surface.

In an embodiment, an optoacoustic probe for optoacoustic imaging of a tissue may have a distal end operable to contact the tissue and a proximal end, the probe comprising an acoustic lens having a distal surface the acoustic lens comprising a carrier material and boron nitride; an optical element; and a housing comprising a probe face having a distal surface at the distal end of the probe, the probe face defining an acoustic lens opening into which the acoustic lens is disposed and an optical opening into which the optical element is disposed, wherein the distal surface of the acoustic lens is adjacent to the distal surface of the probe face. Optionally, the carrier material of the acoustic lens of the optoacoustic probe may comprise room temperature vulcanized silicone. Optionally, the acoustic lens of the optoacoustic probe may comprise boron nitride at a level of from 1% to 10% by weight of the acoustic lens.

In an embodiment, an optoacoustic probe for optoacoustic imaging of a tissue may have a distal end operable to contact the tissue and a proximal end, the probe comprising an acoustic lens; an optical element; and a housing comprising a probe face at the distal end of the probe, the probe face defining an acoustic lens opening into which the acoustic lens is disposed and an optical opening into which the optical element is disposed, wherein the acoustic lens has a distal lens surface adjacent to the probe face; the distal lens surface having a multi-layer coating comprising a transition metal tie layer distal to the distal lens face, a gold layer distal to the transition metal tie layer, and diamond-like carbon layer distal to the gold layer. Optionally, the acoustic lens of the optoacoustic probe may comprise room temperature vulcanized silicone and an isolating material selected from the group consisting of titanium dioxide, boron nitride, barium sulfate, and mixtures thereof. Optionally, the isolating material of the optoacoustic probe may comprise titanium dioxide at a level of from 4% to 6% by weight of the acoustic lens.

In an embodiment, an optoacoustic probe for optoacoustic imaging of a tissue may have a distal end operable to contact the tissue and a proximal end, the probe comprising an acoustic lens having a distal surface; an optical element; and a housing comprising a probe face having a distal surface at the distal end of the probe, the probe face defining an acoustic lens opening into which the acoustic lens is disposed and an optical opening into which the optical element is disposed; wherein the distal surface of the acoustic lens is adjacent to the distal surface of the probe face, and the distal surface of the lens comprises a coating comprising a polytetrafluoroethylene polymer. Optionally, the acoustic lens of the optoacoustic probe may comprise room temperature vulcanized silicone and an isolating material selected from the group consisting of titanium dioxide, boron nitride, barium sulfate, and mixtures thereof. Optionally, the isolating material of the optoacoustic probe may comprise titanium dioxide at a level of from 4% to 6% by weight of the acoustic lens.

In an embodiment, an optoacoustic probe for optoacoustic imaging of a tissue may have a distal end operable to contact the tissue and a proximal end, the probe comprising an acoustic element; a first optical element and a first fiberoptic array in optical communication with the first optical element; a second optical element and a second fiberoptic array in optical communication with the second optical element. The probe may also comprise a housing comprising a probe face at the distal end of the probe, the probe face having a height and a width, and defining an acoustic element opening, a first optical element opening into which the first optical element is disposed, and a second optical element opening into which the second optical element is disposed, an acoustic element receiver into which the acoustic element is disposed, extending proximally from the acoustic element opening, acoustic element receiver having a rear face opposite and in a plane parallel to the acoustic element opening. The probe may also comprise a bracket comprising a transverse member parallel to the probe face and having a first end, an opposite second end, and a middle section attached to the rear face of the acoustic element receiver, the bracket comprising a first optical element receiver at the first end of the transverse member and extending orthogonally and distally from the transverse member; and a second optical element receiver at the second end of the transverse member and extending orthogonally and distally from the transverse member, wherein the first optical element comprises a tubular member at the distal end of the first optical receiver into which the first optical element is disposed, and a slot at the proximal end of the first optical receiver into which the first optical array is disposed, and the second element receiver comprises a tubular member at the distal end of the second optical receiver into which the second optical element is disposed, and a slot at the proximal end of the second optical receiver into which the second optical array is disposed.

Optionally, the first fiberoptic array of the optoacoustic probe has a distal end adjacent to the first optical element, the array comprising a plurality of optical fibers terminating in an array of fiber ends at the distal end of the array and a support member at the proximal end of the array, the support member having a first flange disposed against the proximal face of the transverse member. Optionally, the second fiberoptic array of the optoacoustic probe has a distal end adjacent to the second optical element, the array comprising a plurality of optical fibers terminating in an array of fiber ends at the distal end of the array and a support member at the proximal end of the array, the support member having a second flange disposed against the proximal face of the transverse member. Optionally, the optoacoustic probe may further comprise a clamping member attached to the proximal face of the transverse member, such that the first flange is disposed between the clamping member and the transverse member and the second flange is disposed between the clamping member and the transverse member. Optionally, the optoacoustic probe may further comprise a connector extending from the clamping member, through the transverse member, and terminating in the rear face of the transducer receiver. Optionally, the probe face of the optoacoustic probe has a distal face and the first optical element comprises an optically transparent plate having a distal face and a diffuser, the optically transparent plate being disposed in the first optical element opening such that the distal surface of the optically transparent plate and the distal surface of the probe face form a continuous surface.

In an embodiment, an optoacoustic probe for optoacoustic imaging of a tissue may have a distal end operable to contact the tissue and a proximal end, the probe comprising an acoustic transducer; an optical cover comprising an optically transparent plate having a distal surface; and a housing comprising a probe face having a distal surface at the distal end of the probe, the probe face defining a transducer opening into which the acoustic transducer is disposed, and an optical opening into which the optically transparent plate is disposed such that the distal surface of the optically transparent plate and the distal surface of the probe face form a continuous surface.

In an embodiment, an optoacoustic probe for optoacoustic imaging of a tissue may have a distal end operable to contact the tissue and a proximal end, the probe comprising: an acoustic element; an optical element comprising a diffuser having a proximal end, the proximal end of the diffuser comprising a concave surface; a housing comprising a probe face at the distal end of the probe, the probe face defining an acoustic element opening into which the acoustic element is disposed, and an optical opening into which the optical element is disposed; and a fiberoptic array having a distal end in optical communication with the cylindrical lens, the array comprising a plurality of optical fibers terminating in an array of fiber ends at the distal end of the array, wherein the optical fibers are disposed in a plurality of rows spaced at least about 2 mm apart.

In an embodiment, an optoacoustic probe for optoacoustic imaging of a tissue may have a distal end operable to contact the tissue and a proximal end, the probe comprising: an acoustic element; an optical element comprising a diffuser having a proximal end, the proximal end of the diffuser having a holographic diffusing coating; a housing comprising a probe face at the distal end of the probe, the probe face defining an acoustic element opening into which the acoustic element is disposed, and an optical opening into which the optical element is disposed; and a fiberoptic array having a distal end in optical communication with the proximal end of the diffuser.

In an embodiment, an optoacoustic probe for optoacoustic imaging of a tissue may have a distal end operable to contact the tissue and a proximal end, the probe comprising an acoustic element; an optical element having a proximal end; a housing comprising a probe face at the distal end of the probe, the probe face defining an acoustic element opening into which the acoustic element is disposed, and an optical opening into which the optical element is disposed; a fiberoptic array having a distal end in optical communication with the proximal end of the optical end, the distal end of the fiberoptic array and the proximal end of the optical end defining a gap; an optical sensor disposed in the gap.

In an embodiment, an optoacoustic probe for optoacoustic imaging of a tissue may have a distal end operable to contact the tissue and a proximal end, the probe comprising an acoustic lens having a proximal end; an acoustic transducer having a distal end in acoustic communication with the proximal end of the acoustic lens, the distal end of the acoustic transducer being coated with gold; an optical element; and a housing comprising a probe face at the distal end of the probe, the probe face defining an acoustic element opening into which the acoustic lens is disposed and an optical opening into which the optical element is disposed.

In an embodiment, an optoacoustic probe for optoacoustic imaging of a tissue may have a distal end operable to contact the tissue and a proximal end, the probe comprising an acoustic element; an optical element having a proximal end; a housing comprising a probe face at the distal end of the probe, the probe face defining an acoustic element opening into which the acoustic element is disposed, and an optical opening into which the optical element is disposed; and a fiberoptic array having a distal end in optical communication with the proximal end of the optical element, the fiberoptic array comprising a plurality of optical fibers, each fiber having an unjacketed portion at the distal end of the fiberoptic array, and a jacketed portion extending proximally from the unjacketed portion.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

FIG. 4E shows a cutaway view of an alternative embodiment of a distal housing portion.

FIG. 4I shows an enlarged cross-sectional view of a distal portion of the probe housing.

Figure 1:
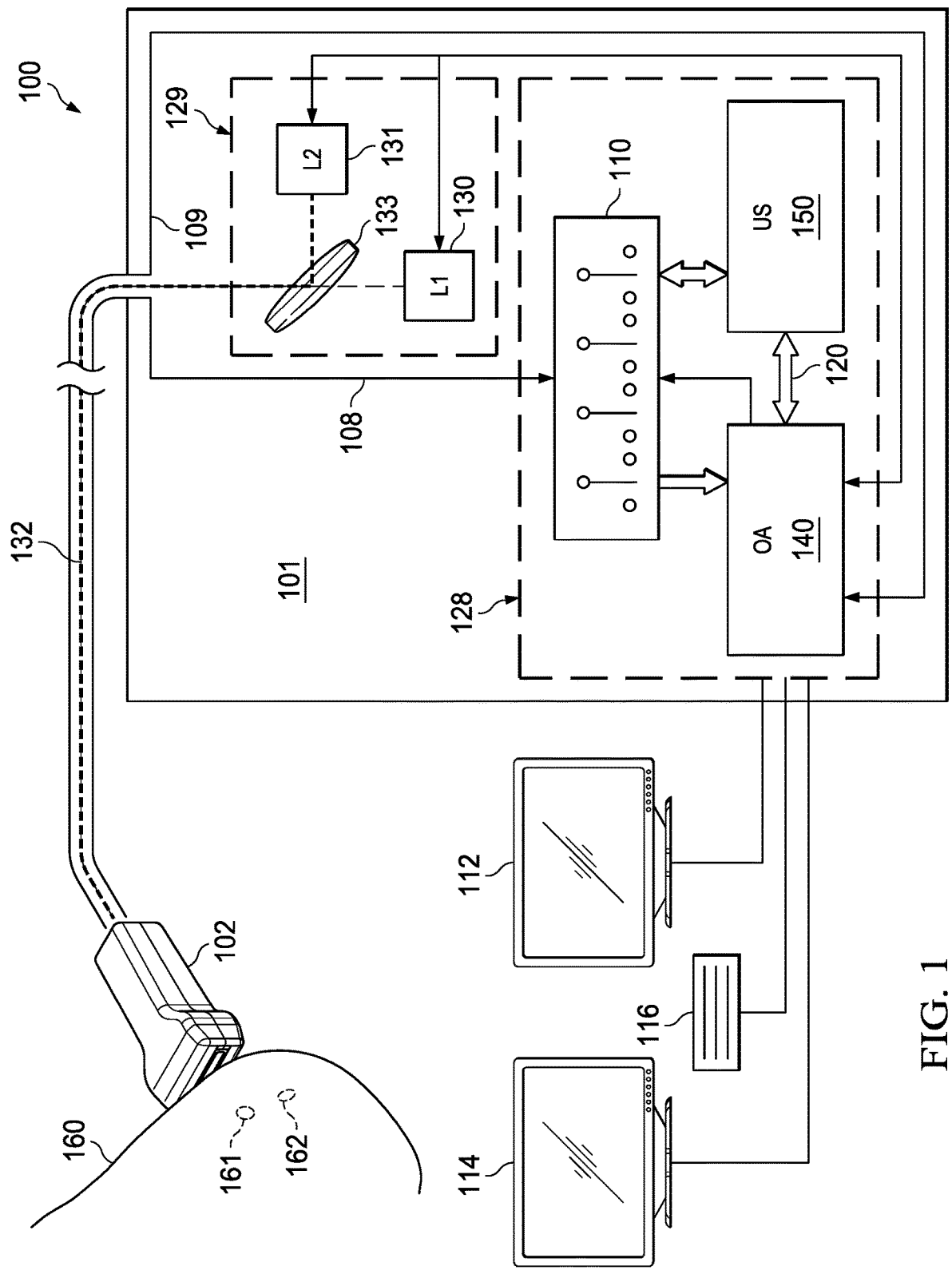
FIG. 1 shows a schematic block diagram illustrating an embodiment of a combined optoacoustic and ultrasound system that may be used as a platform for the methods and devices disclosed herein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

The systems and methods are described below with reference to, among other things, block diagrams, operational illustrations and algorithms of methods and devices to provide optoacoustic imaging with out-of-plane artifact suppression. It is understood that each block of the block diagrams, operational illustrations and algorithms and combinations of blocks in the block diagrams, operational illustrations and algorithms, can be implemented by means of analog or digital hardware and computer program instructions.

These computer program instructions can be stored on computer-readable media and provided to a processor of a general purpose computer, special purpose computer, ASIC, or other programmable data processing apparatus, such that the instructions, which execute via the processor of the computer or other programmable data processing apparatus, implements the functions/acts specified in the block diagrams, operational block or blocks and or algorithms.

In some cases, frequency domain-based algorithms require zero or symmetric padding for performance. This padding is not essential to describe the embodiment of the algorithm, so it is sometimes omitted from the description of the processing steps. In some cases, where padded is disclosed in the steps, the algorithm may still be carried out without the padding. In some cases, padding is essential, however, and cannot be removed without corrupting the data.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

Reference will now be made in more detail to various embodiments of the present invention, examples of which are illustrated in the accompanying figures. As will be apparent to one of skill in the art, the data structures and processing steps described herein may be implemented in a variety of other ways without departing from the spirit of the disclosure and scope of the invention herein and should not be construed as being limited to the embodiments set forth herein. Rather, these embodiments are provided so that this disclosure will be thorough and complete, and will fully convey the concept of the disclosure to those skilled in the art.

System and Method for Presenting Optoacoustic Data

Embodiments herein may be implemented in connection with one or more of the systems and methods described in one or more of the following patents, publications and/or published applications, all of which are expressly incorporated herein by reference in their entireties:

U.S. Pat. No. 7,999,161, titled "Laser-Activated Nanothermolysis Of Cells" filed Jul. 23, 2007;

U.S. Pat. No. 9,289,191, titled "System and method for Acquiring Optoacoustic Data and Producing Parametric Maps Thereof", and filed Jun. 13, 2012;

U.S. Pat. No. 9,517,055, titled "System And Method For Acquiring Optoacoustic Data And Producing Parametric Maps Using Subband Acoustic Compensation" filed Nov. 25, 2013;

U.S. Pat. No. 9,724,072, titled "System And Method For Mixed Modality Acoustic Sampling" filed Dec. 13, 2013;

U.S. Pat. No. 9,456,805, titled "System And Method For Acquiring Optoacoustic Data And Producing Parametric Maps Using Interframe Persistent Artifact Removal" filed Dec. 19, 2013;

U.S. Publication 2016/0199037, titled "System And Method For Acquiring Optoacoustic Data And Producing Parametric Maps thereof" filed Mar. 22, 2016;

U.S. Publication 2017/0035388, titled "System And Method For Mixed Modality Acoustic Sampling" filed Oct. 18, 2016;

U.S. Pat. No. 9,792,686, titled "System And Method For Acquiring Optoacoustic Data And Producing Parametric Maps Using Subband Acoustic Compensation" filed Nov. 17, 2016;

U.S. Publication 2017/0296151, titled "System And Method For Mixed Modality Acoustic Sampling" filed Jun. 30, 2017;

U.S. Publication 2013/0109950, titled "Handheld Optoacoustic Probe" filed Nov. 2, 2011;

U.S. Publication 2016/0296121, titled "Handheld Optoacoustic Probe" filed May 2, 2016;

U.S. Pat. No. 8,686,335, titled "System And Method For Adjusting The Light Output Of An Optoacoustic Imaging System" filed Dec. 31, 2011;

U.S. Pat. No. 9,528,936, titled "System And Method For Adjusting The Light Output Of An Optoacoustic Imaging System" filed Mar. 31, 2014;

U.S. Publication 2017/0108429, titled "System And Method For Adjusting The Light Output Of An Optoacoustic Imaging System" filed Dec. 27, 2016;

U.S. Pat. No. 9,330,452, titled "Statistical Mapping In An Optoacoustic Imaging System" filed Mar. 11, 2013;

U.S. Pat. No. 9,836,838, titled "Statistical Mapping In An Optoacoustic Imaging System" filed May 3, 2016;

U.S. Publication 2018/0061050, titled "Statistical Mapping In An Optoacoustic Imaging System" filed Nov. 6, 2017;

U.S. Pat. No. 9,610,043, titled "System And Method For Producing Parametric Maps Of Optoacoustic Data" filed Jun. 13, 2012;

U.S. Publication 2017/0100040, titled "System And Method For Producing Parametric Maps Of Optoacoustic Data" filed Dec. 21, 2016;

U.S. Publication 2013/0338501, titled "System And Method For Storing Data Associated With The Operation Of A Dual Modality Optoacoustic/Ultrasound System" filed Jun. 13, 2012;

U.S. Publication 2013/0338475, titled "Optoacoustic Imaging System With Fiber Optic Cable" filed Jun. 13, 2012;

U.S. Publication 2014/0194723, titled "Multi-Layer Coating For Optoacoustic Probe" filed Jan. 13, 2014;

U.S. Publication 2017/0150890, titled "Optoacoustic Probe With Multi-Layer Coating" filed Jan. 31, 2017;

U.S. Pat. No. 9,615,750, titled "Methods And Compositions For Carrier Agents And Clearing Agents Used In Optoacoustic Imaging Systems" filed Jun. 14, 2012;

U.S. Publication 2013/0116538, titled "Optoacoustic Imaging Systems And Methods With Enhanced Safety" filed Oct. 19, 2012;

U.S. Publication 2015/0297090, titled "Optoacoustic Imaging Systems And Methods With Enhanced Safety" filed Jan. 23, 2015;

U.S. Publication 2013/0289381, titled "Dual Modality Imaging System For Coregistered Functional And Anatomical Mapping" filed Nov. 2, 2012;

U.S. Pat. No. 9,757,092, titled "Method For Dual Modality Optoacoustic Imaging" filed Nov. 2, 2012;

U.S. Publication 2014/0039293, titled "Optoacoustic Imaging System Having Handheld Probe Utilizing Optically Reflective Material" filed Jan. 22, 2013;

U.S. Publication 2017/0014101, titled "Dual Modality Imaging System For Coregistered Functional And Anatomical Mapping" filed Sep. 27, 2016;

U.S. Publication 2013/0303875, titled "System And Method For Dynamically Varying The Angle Of Light Transmission In An Optoacoustic Imaging System" filed Nov. 2, 2012;

U.S. Pat. No. 9,445,785, titled "System And Method For Normalizing Range In An Optoacoustic Imaging System" filed Dec. 21, 2012;

U.S. Pat. No. 9,282,899, titled "System And Method For Detecting Anomalous Channel In An Optoacoustic Imaging System" filed Dec. 21, 2012;

U.S. Publication 2014/0005544, titled "System And Method For Providing Selective Channel Sensitivity In An Optoacoustic Imaging System" filed Dec. 21, 2012;

U.S. Publication 2016/0317034, titled "System And Method For Providing Selective Channel Sensitivity In An Optoacoustic Imaging System" filed Jul. 11, 2016;

U.S. Pat. No. 9,445,786, titled "Interframe Energy Normalization In An Optoacoustic Imaging System" filed Jan. 22, 2013;

U.S. Publication 2017/0000354, titled "Interframe Energy Normalization In An Optoacoustic Imaging System" filed Sep. 19, 2016;

U.S. Publication 2014/0206978, titled "Probe With Optoacoustic Isolator" filed Jan. 22, 2013;

U.S. Pat. No. 9,743,839, titled "Playback Mode In An Optoacoustic Imaging System" filed Mar. 15, 2013;

U.S. Publication 2017/0332916, titled "Playback Mode In An Optoacoustic Imaging System" filed Jul. 27, 2017;

U.S. Pat. No. 9,398,893, titled "System And Method For Diagnostic Vector Classification Support" filed Mar. 11, 2014;

U.S. Pat. No. 10,026,170, titled "System And Method For Diagnostic Vector Classification Support" filed Jul. 19, 2016

U.S. application Ser. No. 16/022,138, titled "System And Method For Diagnostic Vector Classification Support" filed Jun. 28, 2018;

U.S. Pat. No. 9,730,587, titled "Diagnostic Simulator" filed Mar. 15, 2013;

U.S. Publication 2017/0332915, titled "Diagnostic Simulator" filed Jul. 27, 2017;

U.S. Pat. No. 8,823,928, titled "Light Output Calibration In An Optoacoustic System" filed Mar. 15, 2013;

U.S. Pat. No. 9,163,980, titled "Light Output Calibration In An Optoacoustic System" filed Jul. 11, 2014;

U.S. Pat. No. 9,814,394, titled "Noise Suppression In An Optoacoustic System" filed Mar. 15, 2013;

U.S. Publication 2018/0078144, titled "Noise Suppression In An Optoacoustic System" filed Nov. 13, 2017;

U.S. Pat. No. 9,733,119, titled "Optoacoustic Component Utilization Tracking" filed Mar. 15, 2013;

U.S. Publication 2017/0322071, titled "Optoacoustic Component Utilization Tracking" filed Jul. 27, 2017;

U.S. Publication 2015/0101411, titled "Systems And Methods For Component Separation In Medical Imaging" filed Oct. 13, 2014;

U.S. Publication 2015/0305628, titled "Probe Adapted To Control Blood Flow Through Vessels During Imaging And Method Of Use Of Same" filed Feb. 27, 2015

U.S. Publication 2016/0187481, titled "Opto-Acoustic Imaging System With Detection Of Relative Orientation Of Light Source And Acoustic Receiver Using Acoustic Waves" filed Oct. 30, 2015.

Optoacoustic/ultrasound imaging systems as described below visualize thin tissue slices noninvasively through skin at a tissue site. The term "tissue site" broadly refers to locations or targets of animal and human tissues and organs such as, for example, breast tissue. A tissue site may contain a variety of different "tissue structures" that may include, for example, tumors, blood vessels, tissue layers, and components of blood. As described below, a sinogram may contain a sample recording of acoustic activity occurring over a period of time in response to one or more light events impinging on the tissue site. The acoustic activity captured in the sinogram may include an optoacoustic response, i.e., the acoustic signal that is created as a result of the electromagnetic energy being absorbed by materials within the tissue site such as, for example, various tissue structures that absorb the electromagnetic energy. These optical signals result from the release of thermo-elastic stress confinement within the tissue structures in response to the light events.

Turning to FIG. 1, and as described generally below under the heading Optoacoustic System and Method is a device 100, including a probe 102 connected via a light path 132 and an electrical path 108 to a system chassis 101. Within the system chassis 101 is housed a light subsystem 129 and a computing subsystem 128. The computing subsystem 128 includes one or more computing components for, among other things, optoacoustic control and analysis. In an embodiment, through the sampling of transducers in the probe 102, the device 100 can obtain data received in response to: stimulation caused by pulsed light sources 130, 131 (i.e., the optoacoustic return signal); and to stimulation caused by acoustic output of the ultrasound transducer elements.

In an embodiment, to obtain an optoacoustic return signal corresponding to a single light event occurring in a volume of tissue, the transducers in the probe 102 can be sampled for a period of time after the light event. In an embodiment, the transducers in the probe 102 can be sampled for a period of time after the light event approximately equal to the time it would take sound to travel a desired distance in the tissue. In an embodiment, the desired distance may be at least one centimeter. In an embodiment, the desired distance may be at least two centimeters. In an embodiment, the period of sampling would correspond to the amount of time it would take sound to travel at least one, but not more than 15 centimeters in tissue. The sampling rate should be sufficient to obtain sufficient information in the optoacoustic return signal. In an embodiment, the sampling rate is above 20 megahertz (MHz), in another embodiment, the sampling rate is above about 30 MHz.

As discussed further below, in an embodiment, the device 100 comprises at least two light sources 130, 131 operating at different light wavelengths. In an embodiment, with two light sources 130, 131 operating at different light wavelengths, the optoacoustic return signal from one light event from each of the light sources can be used in the method and system for presenting the optoacoustic data. In an embodiment, the device 100 comprises a single light source that may be operated at different wavelengths, such as a tunable laser that can change wavelengths quickly enough for use as described herein. In an embodiment, the device 100 comprises at least two light sources 130, 131, each being capable of tuning to a plurality of different wavelengths. In an embodiment, the device 100 comprises one light source 130 operating a one light wavelength, and at least one additional light source 131 capable of being tuned to a plurality of different wavelengths.

As used herein, the term sinogram refers to sampled data or processed sampled data corresponding to a single light event. The term sinogram is also used at times to refer to an image presented by using the original or filtered sampled data as gray scale or color data, wherein there is a correspondence between the samples in the data and the voxels in the image. In an embodiment, using optoacoustic return signals from two different light events, each corresponding to a different wavelength of light, the term short sinogram refers to the sinogram corresponding to the shorter wavelength of light generating a light event, and the term long sinogram refers to the sinogram corresponding to the longer wavelength of light generating a light event. Because more than two different wavelengths may be used, the use of the terms short and long wavelength are intended to embody the extended context of a system with an arbitrary number of wavelengths.

In an embodiment, as discussed in more detail below, sinograms are processed to produce an envelope image. As used herein the term short envelope image refers to an envelope image corresponding to the short sinogram, and the term long envelope image refers to an envelope image corresponding to the long sinogram. In an embodiment, the short sinogram and long sinogram are each processed separately to produce a short envelope image and a long envelope image, respectively. The short and long envelope images are then used together to generate parametric images. From the parametric images, maps can be created of oxygenation, hemoglobin and masked oxygenation. These maps can be co-registered data representing an ultrasound image of substantially the same volume, and can thereafter produce one or more of an oxygenation image, a hemoglobin image and a masked oxygenation image. In an embodiment, the oxygenation image, hemoglobin image and masked oxygenation image reflect information about the composition of the volume of tissue. The terms parametric map and parametric image are in some instances used interchangeably. The use of the term map generally relates to the correspondence between the image and a volume. Parametric maps may be represented in numerous ways, including, for example, as a single-channel (i.e., grayscale) representation, as a color (i.e., RGB) representation, or as a color with transparency (RGBA) representation. Parametric maps may be used to convey qualitative or quantitative information about one or more parameters. A parametric map or parametric image may be represented in computer memory or presented as a displayed representation, thus, as used herein, the term "image" or "map" do not necessarily imply a visual representation.

For a variety of reasons, sinograms may contain unwanted, inaccurate or insufficiently scaled data. These maladies of sinogram data may result from myriad reasons, including characteristics of the measuring instrument (e.g., the probe) or the light used, characteristics of the volume (i.e., the tissue), characteristics of the interaction between the volume and the probe or light, external stimuli, or other sources. Regardless of the source, a variety of processes can be used to remove unwanted aspects of the sinogram data.

Generally in each of the following steps for processing the sinogram, the processing is performed on the time domain signal. In a preferred embodiment (and as discussed below) the probe 102 includes an acoustic lens that enables the sinogram data to be more focused on what is on the plane below that of the transducers—the image plane. In an embodiment, the probe comprises an acoustic lens having a focal length of between 10 and 40 millimeters. In an illustrative embodiment, the probe comprises an acoustic lens having a focal length of 20 millimeters. In an embodiment, the probe may comprise an acoustic lens having a focal length that can be zoomed in or out, in hardware, or in software.

As discussed above, in an illustrative embodiment, each channel of the sinogram data represents approximately 100 millimeters of distance in the volume. The acoustic lens generally rejects at least some portion of a signal propagating from points outside (e.g., orthogonal) to the image plane. Each transducer, however, receives signal from substantially all points of the image plane that lie within the approximately 100 millimeters distance. The received signal for a channel can be thought of as comprising the area of a semicircle of radius 100 millimeters on the image plane.

Figure 2:
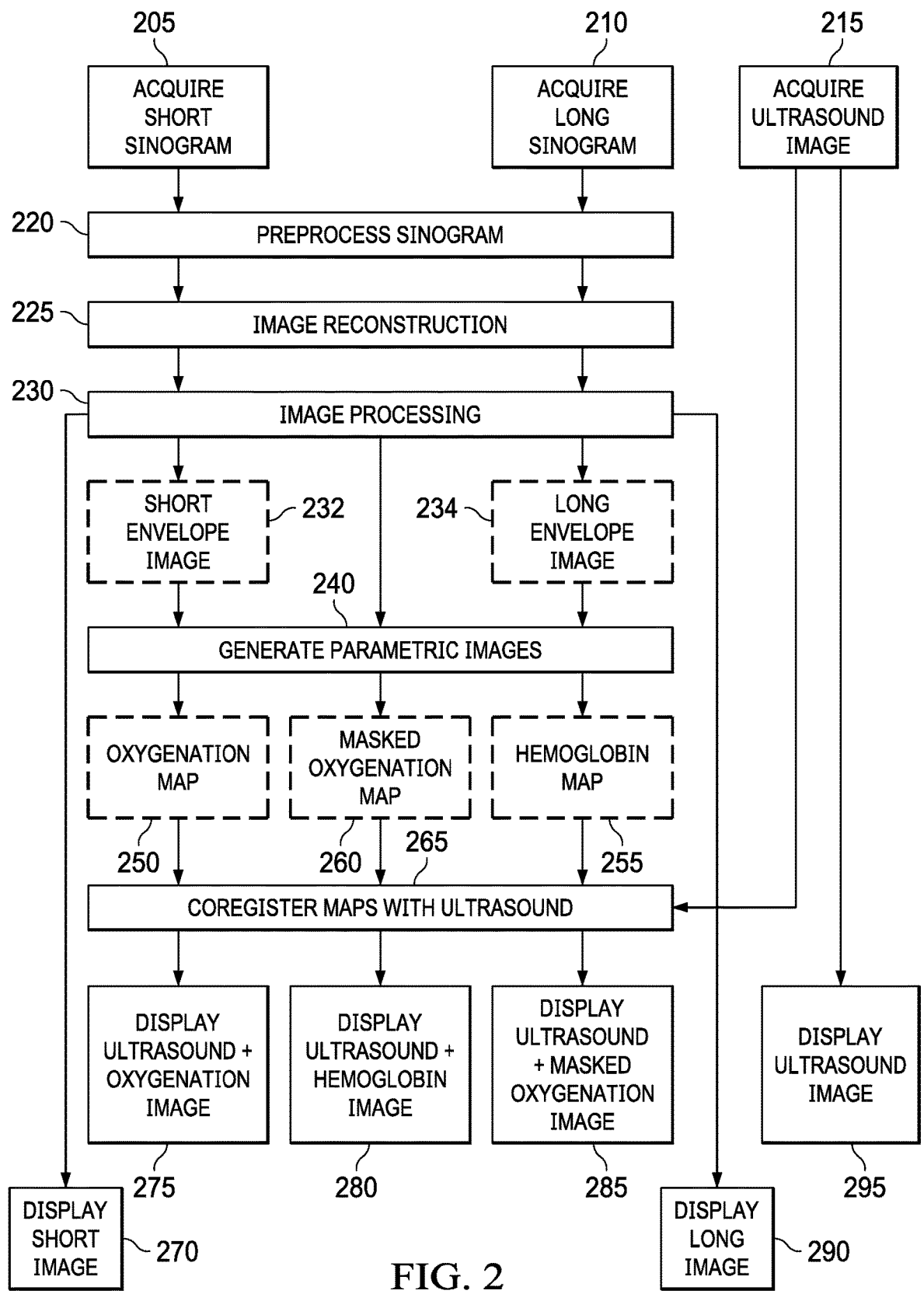
FIG. 2 shows a flow for an illustrative embodiment of a method of providing output images resulting from optoacoustic data, and from optoacoustic data combined with ultrasound data.

Turning to FIG. 2, an overview of an example process is shown, beginning with the acquisition of three sets of data, namely, a short sinogram (step 205), a long sinogram (step 210) and an ultrasound image (step 215), and processing the data to produce up to six separate images that may be useful in viewing various aspects of that acquired data. In an example embodiment, the three sets of acquired data may be acquired using a probe 102 (FIG. 1). For the purposes of illustration herein, it may be presumed that probe 102 movement is minimal, if any, between the acquisition of the three sets of data in steps 205, 210 and 215. In an example embodiment, a reasonable frame rate (e.g., 10 Hz), coupled with a reasonably steady hand used in handholding the probe may yield the three data sets having substantially minimal movement occurring there-between. It should be noted that the process described herein is not limited to being used with the three identified data sets. Use of additional data sets, such as, for example, data sets from additional wavelengths of light, may be used to further improve the resulting images.

As will be discussed in more detail below, the short and long sinogram data are preprocessed (step 220) in one or more separate manners to reduce or compensate for undesired data in the sinogram, including characteristics of the measuring instrument (e.g., the probe) or the light used, characteristics of the volume (i.e., the tissue), characteristics of the interaction between the volume and the probe or light, external stimuli, or other sources. After the preprocessing, separate short and long images are reconstructed (step 225). In an embodiment, separate real and imaginary components of complex short and long images result from the reconstruction step. In an embodiment, the processing (step 230) of the reconstructed images is performed. The processing (step 230) may remove additional artifacts that can be identified in the reconstructed images, and in any event creates a short envelope image (232) and a long envelope image (234). In an embodiment, the short and long envelope images (232, 234) are used to generate parametric images (step 240) process. The generated parametric images (step 240) process outputs an oxygenation map (250), a hemoglobin map (255) and a masked oxygenation map (260). In an embodiment, any or all of the three maps are coregistered with, and overlaid on an ultrasound image (step 265). A display can be provided for display of one or more of the displayable images displayed in steps 270, 275, 280, 285, 290 and 295. In an embodiment, a group of two or more of the images may be displayed on the same screen, and may be commonly scaled and sized. In an embodiment, the group of all six images may be displayed on the same screen, and may be commonly scaled and sized.

In an embodiment, the system performing processing on the optoacoustic data, and/or the system displaying the optoacoustic output—which may, but need not be the same as the system acquiring the sinogram—would provide the operator the ability to vary parameters used in processing, when processing or viewing optoacoustic images. In an embodiment, the system performing processing on the optoacoustic data, and/or the system displaying the optoacoustic output would provide the operator the ability to switch on and off, and potentially vary the order of, the processing steps used to process the optoacoustic images.

Optoacoustic System and Method

Returning to FIG. 1, generally, device 100 provides an optoacoustic system that may also be employed as multi-modality, combined optoacoustic and ultrasound system. In an embodiment, the device 100 includes a probe 102 connected via a light path 132 and an electrical path 108 to a system chassis 101. Within the system chassis 101 is housed a light subsystem 129 and a computing subsystem 128. The computing subsystem 128 includes one or more computing components for ultrasound control and analysis and optoacoustic control and analysis; these components may be separate, or integrated. In an embodiment, the computing subsystem comprises a relay system 110, an optoacoustic processing and overlay system 140 and an ultrasound instrument 150.

In an embodiment, the light subsystem 129 is capable of producing pulses of light of at least two different wavelengths. In an embodiment, the light subsystem 129 outputs should be capable of producing short pulses of light in each of those wavelengths, e.g., a pulse lasting less than about 100 ns, and potentially as short as about 5 ns. As will be apparent to one of ordinary skill in the art from this disclosure, the inventions disclosed herein may also be practiced using pulsed light comprising pulses lasting greater than 100 ns. In an embodiment, the light subsystem 129 includes two separate light sources 130, 131. The output of the light subsystem 129 is delivered to the probe 102 via the light path 132. In an embodiment, the light sources 130, 131 are lasers producing light in the infrared, near-infrared, and/or visible spectrum. In an embodiment, light source 130 and light source 131 each produce light at a different wavelength in the infrared or near-infrared spectrum. In an embodiment, the light path 132 used to deliver light from the light subsystem 129 to the probe 102 is a fiber optic bundle comprising multiple strands of optical fiber. Optionally, the light path 132 may utilize a liquid filled or silicon structure to deliver the light. In an embodiment, the light path 132 comprises sufficient optical fibers of sufficient size (diameter) to carry a short, high powered pulse of light to the distal end of the light path 132. In an embodiment, the total pulse energy carried over the light path 132 may be on the order of one or more millijoules. In an embodiment, the total energy per light pulse delivered from the light path 132 is less than about 100 millijoules. In an embodiment, the total energy per light pulse carried over the light path 132 is in the range of about 50-90 millijoules, and the light path 132 comprises between about 1,000 and 2,000 optical fibers of between about 100 and 300 microns each. In an embodiment, a single fiber can be used as the light path 132. In such embodiment, the fiber may be 1000-1500 microns in diameter. Of course, the diameter of such single fiber may be smaller, e.g., 400 microns. Given the required total pulse energy carried over the fiber, one skilled in the art can calculate the diameter required of the fiber accordingly.

In an illustrative embodiment, the light subsystem 129 may use Nd:YAG and Alexandrite lasers as its two light sources 130, 131, although other types or wavelengths, and additional lights, may also be used. Light sources 130, 131 should be capable of producing a short pulse of light, e.g., a pulse lasting less than about 100 ns, and more preferably around 5 ns. In an embodiment, the two light sources 130, 131 can be separately triggered. In an embodiment, the light output by the light sources 130, 131 may be projected onto the same light path 132 through the use of an optical element 133 that generally permits one light 130 to pass through from a first side to a second side, while reflecting one light source 131 that strikes the second side. The use of optical element 133 or a similar element permits the alignment of the output of two light sources 130, 131 such as lasers onto proximal end of the light path 132. In an embodiment, optical elements 133 can align the light output from more than two lasers, for example, through the use of multiple optical elements 133. In an embodiment, multiple light systems and light paths may be employed, with the light of each light system being carried on separate fibers or fiber groups that may be intermingled and/or randomized (discussed further below) and/or grouped at their distal ends. Intermingled, as used in this context, refers to the mapping of the fibers in the light path such that fibers are generally distributed in a relatively even manner in the distal groupings. Thus, a plurality of adjacent fibers on the proximal end of the light path would generally be about evenly divided in groupings on the distal end. As an illustrative example, where there are two distal groupings, any arbitrary selection of a sufficient group of adjacent fibers on the proximal end should be about evenly split between the two distal groupings. The randomization, intermingling and/or grouping need not take place at any specific location on the light path 132. In other words, for example, the division of a fiber cable from one proximal group to two distal groups can occur at any point along the light path 132, or along substantially the entire length of the light path 132. Similarly, the randomization and/or intermingling need not take place along the entire length of the light path, but rather, for example, may take along a distance of, e.g., a few centimeters or more near either end of the light path, or anywhere else along the light path 132. Randomizing fibers between one end and the other end of a light path prevents a local anomaly affecting an adjacent group of the fibers on the input from affecting a significant adjacent group of the fibers on the output. Intermingling fibers between one end and the other end of a light path prevents a local anomaly affecting an adjacent group of the fibers on the input from disproportionately affecting one group or subgroup of fibers on the output.

Where the light path terminates in multiple groupings (or subgroupings) of fibers, the distal ends of the groupings (or subgroupings) may be fused, or lapped and polished, or just secured together (removable or otherwise). In an embodiment, the distal end of the light path is formed into a plurality of groups that are spaced in such a manner so as to permit light to emit on each side of the transducer array. In an embodiment, the distal end of the light path is formed into a plurality of groups that are spaced in such a manner so as to permit light to emit around the entire transducer array. In an embodiment, the distal end of the light path is formed into two or more groups, and the two or more groups subdivided into subgroups that are separately secured by a light bar guide, which light bar guide may be associated with the group. In an embodiment, optical elements 133 can consist of optical elements that are used to measure the light energy to determine energy per light pulse.

Although the total energy per light pulse carried over the light path 132 is in the order of tens of millijoules, because the pulse of light sources 130, 131 is so short, the peak power output over the light path 132 is frequently approaching or in the megawatt range. Accordingly, the output of light sources 130, 131 has the capacity to cause the optical fibers and/or the cladding on the optical fibers to burn, discolor or otherwise degrade. Such degraded optical fibers and/or cladding, whether burnt, discolored, or otherwise, can exacerbate the problem as they begin to transmit less light power and cause more heating. In an embodiment, at least some of the cladding may be removed from the optical fibers prior to the initial operation of the probe to prevent fiber burnout. In an embodiment, sufficient number and size optical fibers are present in the light path 132 to permit handling of the peak power loads and avoid fiber burnout. To accommodate higher peak power, a larger fiber bundle can be used. It will be apparent to a person of skill in the art that the peak power capacity of a fiber bundle can be increased by increasing the number of optical fibers, or the diameter of optical fibers, or both. Notably, however, as the dimension of the fiber bundle increases, the weight and flexibility of the light path 132 may become less desirable. Moreover, when using more optical fibers, or optical fibers of a larger diameter, the output of light subsystem 129 must be delivered to the light path 132 across the wider diameter of the larger bundle. In an embodiment, regardless of the ultimate size of the proximal end of light path 132, the output of light subsystem 129 should be distributed sufficiently across its cross section to prevent burn out failures when operating in expected peak power ranges. In an embodiment, the fibers of the proximal end of the light path 132 may be fused to form a fused entry point to the light path 132 for the output of light subsystem 129. In an embodiment, the fiber ends can be fused by applying heat. In an embodiment, a fused end may be surrounded with a metal ring. In an embodiment, a fused end may be surrounded with a stainless steel ring. Once the proximal end of light path 132 has been fused, it will resist burnout at substantially higher peak power. For example, using a fused end light path 132 may permit carriage of three, four or even five times as much peak power. The ability to carry substantially higher peak power in a given light path 132 permits use of a more flexible and lighter fiber optic bundle to carry the same peak power as an un-fused light path 132. Thus, in an embodiment, where a ½" (12.7 mm) fiber optic bundle may have been required in an un-fused bundle of optical fibers forming a light path, a ¼" (6.35 mm) fiber optic bundle with a fused proximal end may be used to carry the same peak power. A ¼" (6.35 mm) fiber optic bundle with a fused proximal end is approximately ¼ of the weight and much more flexible than a ½" (12.7 mm) fiber optic bundle. Moreover, fusing of the proximal end of light path 132 may produce an even smaller fused area to illuminate using light source 132 as the fusing removes the inter-fiber spaces that would have existed in the bundled end of the round-cross-section optical fibers. Accordingly, one or more of the following advantages may be attained by fusing the proximal end of the optical fibers comprising the light path 132: reduced weight of the light path; increased flexibility of the light path; reduced failure; increased reliability; higher peak power capacity.

In an embodiment, the proximal end of the light path 132 may be separated into separate groups for separate light sources 130, 131 in a light source 132, and light output by the light sources 130, 131 may be projected onto different proximal groups of the light path 132. More than two separate lights may be used, and the proximal end of the light path 132 may be separated into at least one group for each light. Each group of fibers at the proximal end of the light path 132 may be fused together to form a fused entry point to the light path 132 for the light with which it is associated. In an embodiment, the fibers of a light path having multiple groups on the proximal and are intermingled with respect to the groups or subgroups on the proximal ends. In an embodiment, the fibers of a light path having multiple groups on the proximal and are randomized with respect to the groups or subgroups on the proximal ends. In an embodiment, a light path is provided with a fused proximal end (input) and at least two groups on its distal end (outputs), the fibers being intermingled and randomized, thus preventing a local anomaly affecting adjacent fibers at the input of the light path from: (i) causing an anomaly affecting a substantial number of adjacent fibers on an output; and (ii) disproportionately affecting one of the outputs. In an embodiment, a light path is provided with at least two groups on its proximal end (inputs) and at least two groups on its distal end (outputs), the fibers being intermingled and randomized, thus preventing a local anomaly affecting adjacent fibers at an input of the light path from: (i) causing an anomaly affecting a substantial number of adjacent fibers on an output; and (ii) disproportionately affecting one of the outputs. In an embodiment, a light path is provided with at least two fused groups on its proximal end (inputs) and at least two fused groups on its distal end (outputs), the fibers being intermingled and randomized, thus preventing a local anomaly affecting adjacent fibers at an input of the light path from: (i) causing an anomaly affecting a substantial number of adjacent fibers on an output; and (ii) disproportionately affecting one of the outputs.

In an embodiment, optical fiber of the type that may be used in light path 132 includes a transparent core surrounded by a transparent cladding material with a lower index of refraction. The core may be made from any transparent material, although excellent results have been observed using pure glass (i.e., silica). In an embodiment, where optical fibers are to be fused into a bundle, the cladding may be removed in the area to be fused. In an embodiment, the cladding may be removed using a chemical process. For example, for some cladding, hot sulfuric acid or acetone may be used. The removal of cladding prior to fusing reduces the chance of particles of the cladding material becoming embedded in the fused end; as such particles may interfere with the light transmission across light path 132.

In an embodiment, the light output by the light sources 130, 131 is sent towards a fused optical fiber bundle at the proximal end of light path 132 via a light path, which may include optical element 133, internal to the light subsystem 129. In an embodiment, light subsystem 129 is a laser system capable of outputting laser light pulses, at one or more wavelengths, onto light path 132. In an embodiment, light path 132 is a fiber optic bundle having a fused end proximal to the light subsystem 129.

In an embodiment, the device 100 also comprises an electrical path 108 running to and/or from the probe 102 to the system chassis 101. In an embodiment, electrical path 108 runs to and/or from the probe 102 to a relay system 110 within the system chassis 101. The electrical path 108 may run near, alongside or coaxially with the light path 132 from the probe 102 toward their respective connections on the system chassis 101. In an embodiment, the electrical path 108 comprises a plurality of separate coaxial wires. In an embodiment, the electrical path 108 is run in a common jacket with at least a portion of the light path 132. Running electrical path 108 in a common jacket with at least a portion of the light path 132 reduces the number of cables running from the system chassis 101 to the probe 102. Running electrical path 108 in a common jacket with at least a portion of the light path 132 may minimize the diameter and weight of, and increase the durability of, the combined cables (i.e., light path 132 and electrical path 108) running from the system chassis 101 to the probe 102.

In an embodiment, the plurality of coaxial wires is woven around at least a portion of the light path 132. As discussed above, many considerations go into the number of separate optical fibers used in light path 132. As discussed further below, numerous design considerations go into the number of separate electrical leads or traces forming the electrical path 108. In an embodiment, there are about 128 leads (corresponding to 128 transducer elements) or about 256 leads (corresponding to 256 transducer elements) forming the electrical path 108. In an embodiment, there are approximately 1,000 separate optical fibers forming the light path 132. For example, the fiber:lead ratio may be about 4:1. As will be apparent, it is possible to comingle the optical fibers and leads or traces in the electrical path in a variety of ways, including, for example, bundling a group of individual fibers with a single electrical lead or trace, or bundling proportionally larger groupings of fibers and leads together. In an embodiment, the bundling of fibers and leads or traces would be done generally in the proportion of fibers: leads in the system.

One or more displays 112, 114, which may be touch screen displays, are provided for displaying images and all or portions of the device 100 user interface. One or more other user input devices (not shown) such as a keyboard, mouse and various other input devices (e.g., dials and switches) may be provided for receiving input from an operator. As an option, power and control path(s) 109 carry power to the probe 102 and control signals between the probe 102 and the computing subsystem 128.

In an embodiment, the connections between the probe 102 and the system chassis 101 may be formed into a flexible cable, which may consist of the light path 132, the control path(s) 109 and the electrical path 108. The flexible cable may be covered in a common outer jacket or sheath for convenience and ease of use. In an embodiment, a medial portion of the light path 132 forms the core of the single flexible cable, and medial portions of the electrical path 108 and/or control path(s) 109, if any, may be wrapped or braided about the medial portion of the light path 132. In an embodiment, a common outer jacket or sheathing encloses a fiber optic bundle forming a medial portion of the light path 132, a coaxial bundle forming a medial portion of the electrical path 108, and control path(s) 109, if any. In an embodiment, the fibers forming a medial portion of the light path, and the wires forming a medial portion of the electrical path 108, as well as control path(s) 109, if any, may be intertwined or intermingled with each other along the medial portion of the connections between the probe 102 and the system chassis 101.

In an embodiment, the distal end of the flexible cable(s) connecting the probe 102 and the system chassis 101 is associated with, and non-removably integrated as part of the probe 102. In an alternative embodiment, the distal end of the flexible cable(s) connecting the probe 102 and the system chassis 101 is removably associated with the probe 102. To removably associate the flexible cable(s) connecting the probe 102 and the system chassis 101 requires both optical fiber connection for the light path 132 and electrical connection for the electrical path 108 and control path(s) 109, if any.

In an embodiment, the light path 132 is split into two sections, and the two sections are brought together using an optical fiber connector in close proximity to the probe 102. The optical fiber connector may be physically located within the probe 102, or be located outside the probe 102. In an embodiment, an optical fiber connector would mechanically couple and align the cores of the fibers making up the light path 132 so that light can pass from one section to the other without significant loss. In an embodiment, the facing ends of the two sections of the light path 132 are fused, and may be first stripped of cladding and then fused, to mitigate issues of core alignment. Regardless of whether the fiber ends are fused, the ends internal to light path 132 that are being connected by the optical fiber connector may be lapped and polished to improve light transmission. In an embodiment, probe 102 has a removable access panel that permits access to optical and/or electrical connectors located within the probe.

To support removability of the electrical path 108 and control path(s) 109, if any, removable electrical connectors may be provided. In an embodiment, flex circuit is elongated so that connectors which are connected to the end of electrical path 108 are accessible from a removable access panel, thereby permitting the disconnection of electrical path 108. In an embodiment, electrical path 108 (and control path(s) 109, if any) is split into two sections, and the two sections are brought together using an electrical connector in close proximity to the probe 102. The electrical connector may be physically located within the probe 102, or be located outside the probe 102. In an embodiment, an electrical connector would electrically couple the two portions of the electrical path 108 so that signals can pass from one section to the other without significant loss.

In an embodiment, the signals carried on the probe-side portion of electrical path 108 are analog signals, and are terminated into an analog-to-digital converter, and the signals carried on the other portion of the electrical path—the portion that connects to the system chassis 101—are digitized representations of the analog signals carried on the probe-side portion of the electrical path 108. In an embodiment, the signals carried on the electrical path 108 are digital signals given that the analog-to-digital conversion is performed in the body of the probe handle. In an embodiment, the probe-side optical connector(s) and electrical connector(s) for the flexible cable(s) that operationally connects the system chassis 101 to the probe 102 are integrated into a single connector that can be operated to quickly disconnect the probe 102 from the cable.

Probe (102)

Figure 3:
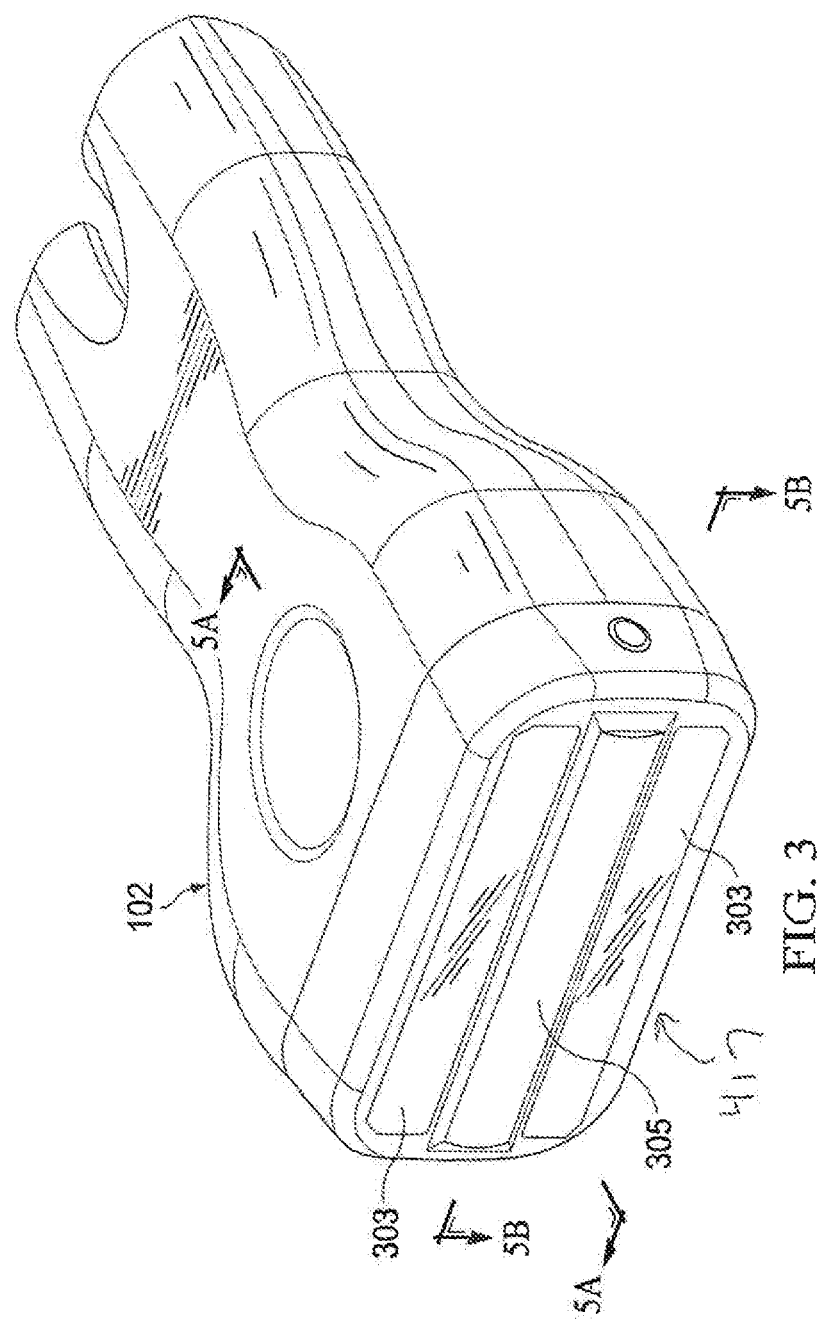
FIG. 3 shows a schematic orthogonal view of an embodiment of a probe that may be used in connection with the methods and other devices disclosed herein.

Turning now to FIG. 3, the probe 102 includes an ultrasound transducer covered by an acoustic lens 305. The probe 102 includes distal and proximal ends. A probe face 417 of the probe 102 is at the distal end. The term "acoustic lens," as used herein, is not limited to an element having a particular structural, mechanical, or optical characteristic. Instead, the term is used to refer to an element that may or may not affect acoustic energy passing through the acoustic lens 305, but will permit at least a substantial portion of the acoustic energy incident thereon to pass through the acoustic lens 305 such that the acoustic energy may be detected by the ultrasound transducer elements. In various embodiments, the acoustic lens 305 may include one or more components that cumulatively form a region through which acoustic energy may pass through in reaching the ultrasound transducer. The acoustic lens comprises an isolating material selected from the group consisting of titanium dioxide, boron nitride, barium sulfate, and mixtures thereof. The isolating material may be embedded throughout the acoustic lens, or alternatively, the isolating material may be formed as an outer layer provided on a distal surface of the lens.

In an embodiment, the ultrasound transducer comprises an array of transducer elements that can both transmit and receive acoustic energy. In an embodiment, at least some of the ultrasound transducer elements are capable of detecting ultrasound frequencies over a wide range. For example, ultrasound transducer elements may be capable of detecting ultrasound in the range from about 50 kHz to 20 MHz. This range can be achieved by applying a high impedance load (e.g., in the range of 5,000 to 50,000 ohms) to achieve a lower frequency response. The ultrasound transducer elements are capable of generating electrical energy in response to receiving ultrasound acoustic energy. The electrical energy generated by the ultrasound transducer elements receiving ultrasound is transmitted to the computing subsystem 128 via electrical path 108.

The probe 102 also includes one or more optical windows 303 through which the light carried on light path 132 can be transmitted to the surface of a volume 160, for example, a three-dimensional volume. In an embodiment, it is desirable to locate one side of the optical window 303 as close as practical to the acoustic lens 305. The total area of an optical window 303 is important to maximize energy for a given fluence incident on the surface of the volume 160.

In an embodiment, the multiple strands of optical fiber making up the light path 132 are terminated in two light bars (not shown). In an embodiment, the ultrasound transducer elements (not shown) are arranged in an array that runs along a geometric plane and are generally spaced equidistant from each other. In an embodiment, the light bars (not shown) are oriented longitudinally, on each side of the planar array of ultrasound transducer elements. Preferably the ultrasound transducer elements generate electrical energy in response to both ultrasound acoustic energy received in response to stimulation caused by the pulsed light sources 130, 131 (i.e., the optoacoustic return signal) and to ultrasound acoustic energy received in response to acoustic output of the ultrasound transducer elements.

Referring back to FIG. 1, in use, the probe 102 may be placed in close proximity with organic tissue, phantom or other volume 160 that may have one or more inhomogeneities 161, 162, such as e.g., a tumor, within. An ultrasound gel (not shown) or other material may be used to improve acoustic coupling between the probe 102 and the surface of the volume 160 and/or to improve optical energy transfer. The probe 102, when in proximity with the surface of the volume 160, can emit a pulse of a light through the optical windows 303 or an ultrasound through acoustic lens 305, and then generate electrical energy corresponding to ultrasound detected in response to the emitted light or sound.

In an embodiment, the computing subsystem 128 can trigger activity from light subsystem 129 over control signal line 106. In an alternative embodiment, the light subsystem 129 can create the trigger signal and inform the computing subsystem 128 of its activity over control signal line 106. Such information can be used to by the computing subsystem 128 to begin the data acquisition process. In this respect, it is noted that communication over control signal line 106 can flow both ways between the computing subsystem 128 (and/or the optoacoustic processing and overlay system 140 therein) and the light subsystem 129.

In an embodiment, computing subsystem 128 can utilize control signal line 106 to control the start time and duration of light pulses from each light source 130, 131 and/or the power supplied to the light source 130,131. The computing subsystem 128 can also trigger the probe 102 to emit ultrasound acoustic energy via the ultrasound transducer elements behind the acoustic lens 305.

In an embodiment, the computing subsystem 128 receives electrical signals representative of the ultrasound detected by the ultrasound transducer elements, in response to an ultrasound transmitted signal or an optically generated ultrasound signal, behind the acoustic lens 305 via electrical path 108. In an embodiment, the electrical signal representative of the ultrasound detected by the ultrasound transducer elements behind the acoustic lens 305 is the analog electrical signal created by the elements themselves. In such embodiment, the electrical signals representative of the ultrasound detected by the ultrasound transducer elements behind the acoustic lens 305 is transmitted to the computing subsystem via electrical path 108, and electrical path 108 is selectively directed by relay system 110 to the optoacoustic processing and overlay system 140 or the ultrasound instrument 150 for processing of the detected ultrasound. In such embodiment, the ultrasound instrument 150 can receive the same input (over the same connector) as it would receive from an ultrasound probe.

In another embodiment, the electrical signal representative of the ultrasound detected by the ultrasound transducer elements behind the acoustic lens 305 is digitized by an analog-to-digital converter which can be housed in the probe 102. In such embodiment, time-resolved electrical signal representative of the ultrasound detected by the ultrasound transducer elements behind the acoustic lens 305 is transmitted across the electrical path 108. Where the electrical signal is digitized at the probe 102, as will be apparent to one of skill in the art, the relay system 110 may be implemented to deliver digital data to the optoacoustic processing and overlay system 140 or the ultrasound instrument 150 or may not be needed at all.

The signal representative of the ultrasound detected by each of the plurality of ultrasound transducer elements behind the acoustic lens 305 may be carried on a separate wire over the electrical path 108. Alternatively, the signal representative of the ultrasound detected by a plurality of ultrasound transducer elements behind the acoustic lens 305, or even all of the ultrasound transducer elements behind the acoustic lens 305, may be multiplexed (e.g., time division or frequency division) utilizing a multiplexer in the probe and a demultiplexer in the computing subsystem 128.

In an embodiment, the ultrasound instrument 150 processes ultrasound-induced acoustic signals to produce ultrasound images and the optoacoustic processing and overlay system 140 processes light-induced acoustic signals to produce optoacoustic images. In an embodiment, the ultrasound instrument 150 and optoacoustic processing and overlay system 140 can be combined into an integrated system performing the combined functions of both. As discussed above, in an embodiment, electrical signals representative of ultrasound detected by the probe 102 and delivered to the computing subsystem 128 via electrical path 108 is switched between the ultrasound instrument 150 and the optoacoustic instrument via relay system 110 in accordance with whether the signal results from ultrasound stimulation or light stimulation.

In an embodiment, tomographic images reflecting the ultrasound-stimulated data may be generated by the ultrasound instrument 150 and tomographic images reflecting the light-stimulated data may be generated by the optoacoustic processing and overlay system 140.

Images, including tomographic images, produced by the optoacoustic processing and overlay system 140 can be stored in a computer memory in that system, along with data associated with sequence or time and date of the image data that was captured. Images, including tomographic images, produced by the ultrasound instrument 150 may be transmitted to the optoacoustic processing and overlay system 140 via a suitable interface 170, where they can be stored, along with images generated from the light-stimulated data, in a time-synchronized manner. In an embodiment, images stored in the memory of the optoacoustic processing and overlay system 140 can be recorded to another memory, e.g., a non-volatile memory internal to, or external to, the device.

In an embodiment, the optoacoustic processing and overlay system 140 can overlay images produced by the ultrasound instrument with images produced by optoacoustic instrument for storage in the memory and/or display on one or more displays 112, 114. In an embodiment, the overlaid optoacoustic image may be shown in a distinct color to distinguish it from the ultrasound image. In an embodiment, the overlaid optoacoustic image may contain colors that correspond to details discernable through optoacoustic imaging, such as, for example, blood oxygenation. In an embodiment, oxygenated blood is shown more in red than blue, while deoxygenated blood is shown in more blue than red. As used herein, the expression overlaid includes merging of the image by mixing as well as traditional overlaying of the image.

In an embodiment, the device 100 may be configured to operate in a cycle comprising a sequence of successively generating and acquiring data relating to one of the device's modalities, i.e., ultrasound or optoacoustic. The minimum time spacing between successive operations of the device's modalities depends on the device 100 components and their ability to fully execute and recycle for use. In an embodiment, a user can select between a variety of preprogrammed cycles such as, for example: ultrasound only; wavelength one only; wavelength two only; wavelength one and two (which may be caused, e.g., by separate lasers, or by a single, quickly tunable, laser); multiple iterations of wavelength one and two followed by ultrasound; and/or multiple iterations of ultrasound followed by wavelength one and/or two. Other and further combinations will be apparent to one of skill in the art. Moreover, where the device 100 is capable of generating more than two wavelengths, numerous additional preprogrammed cycles may be desirable. In an embodiment, additional cycles can be added by the machine operator. In an embodiment, the data collection of an entire cycle is generally intended to be directed to substantially the same portion of volume 160 and to be accomplished in rapid succession. In an embodiment, the device 100 cycles are normally in the range of 1 to 50 per second, and more typically in the range of 2 to 20 per second, as discussed above. The maximum cycle frequency is limited only by the capabilities of the cycle and modalities.

In an embodiment, the displays 112, 114 of device 100 can be configured to show various information depending upon the number of operating cycles selected. In an embodiment, any display 112, 144 or portion of the display can show at least one of the following: an ultrasound only image; a first wavelength response only image; a second wavelength response only image; a combined first and second wavelength response image; and/or an overlay ultrasound image and a wavelength response or combined wavelength response image. The combined first and second wavelength image may comprise a differential or other combinatorial means to provide the image. In an embodiment, an image can be displayed corresponding to each of the separate data collections in a cycle, or corresponding to the sum or difference between any or all of them.

In an embodiment, the device can be operated using a three-phase data collection operation, one phase generating and collecting data in response to ultrasound stimulus, one phase generating and collecting data in response to a first wavelength of light, and one phase generating and collecting data in response to a second wavelength of light. In an embodiment, having a light source capable of generating more than two wavelengths, the device can be operated using a multi-phase data collection operation, one phase generating and collecting data in response to ultrasound stimulus, and one phase generating and collecting data in response to each wavelength of light. Other and further combinations will be apparent to one of skill in the art.

Using proper wavelength(s), optoacoustics is effective in identifying blood within a volume 160 and using multiple wavelengths can be used to readily distinguish between oxygenated and deoxygenated blood. Similarly, using proper wavelengths, optoacoustics is effective for measuring localized hemoglobin content within a volume 160. Thus, for example, a malignant tumor, which is characterized by increased blood concentration and decreased oxygenation, will appear very differently in an optoacoustic image than a benign growth, which is not characterized by such an increased blood concentration and has more normal oxygenation. Moreover, specific wavelengths of light can be selected to better distinguish between various biological tissues and organs. While a large spectrum of infrared, near-infrared and visible wavelengths can produce optoacoustic response in biological entities, oxygenated blood is more optoacoustically responsive than deoxygenated blood to a light source having a wavelength of about 1064 nm, while deoxygenated blood is more optoacoustically responsive than oxygenated blood to a light source having a wavelength of about 757 nm. The number and specific wavelength(s) of light used in the device 100 are selected in accordance with the makeup of the volume and the type of target that is of interest.

In an embodiment, employing an Nd:YAG laser to emit a pulse of light having a predominant wavelength of about 1064 nm and employing an Alexandrite laser to emit a pulse of light having a predominant wavelength of about 575 nm, the Nd:YAG laser will be pulsed first, followed by a delay of about 50 milliseconds, followed by the pulsing of the Alexandrite laser. The cycle length before the following pulse of the Nd:YAG laser may be 100 milliseconds or more. Thus, in an embodiment, the pulses/delays may be as follows: Nd:YAG pulse, 50 millisecond delay, Alexandrite pulse, 50 millisecond delay, yielding a frequency of about 10 Hz, and a cycle time of about 100 milliseconds. Generally, regardless of the total cycle time, the time between the first and second light events should be as short as reasonably practical. Thus, in another embodiment, the pulses/delays may be as follows: Nd:YAG pulse, 50 millisecond delay, Alexandrite pulse, 150 millisecond delay, yielding a frequency of about 5 Hz, and a cycle time of about 200 milliseconds. In yet another embodiment, the pulses/delays may be as follows: Nd:YAG pulse, 50 millisecond delay, Alexandrite pulse, 250 millisecond delay, or a 450 millisecond delay, or a 950 millisecond delay, yielding, respectively, a frequency of about 3.33, 2 and 1 Hz, and cycle times of about 300, 500 and 1,000 milliseconds. In an embodiment, the Alexandrite laser may be pulsed before the Nd:YAG laser. In an embodiment, a graphical user interface (GUI) is provided for operating a clinical optoacoustic system, the GUI including, without limitation: controls that permit operator selection of the cycle time and/or the order of light source pulsing.

Housing (400)

Figure 4A:
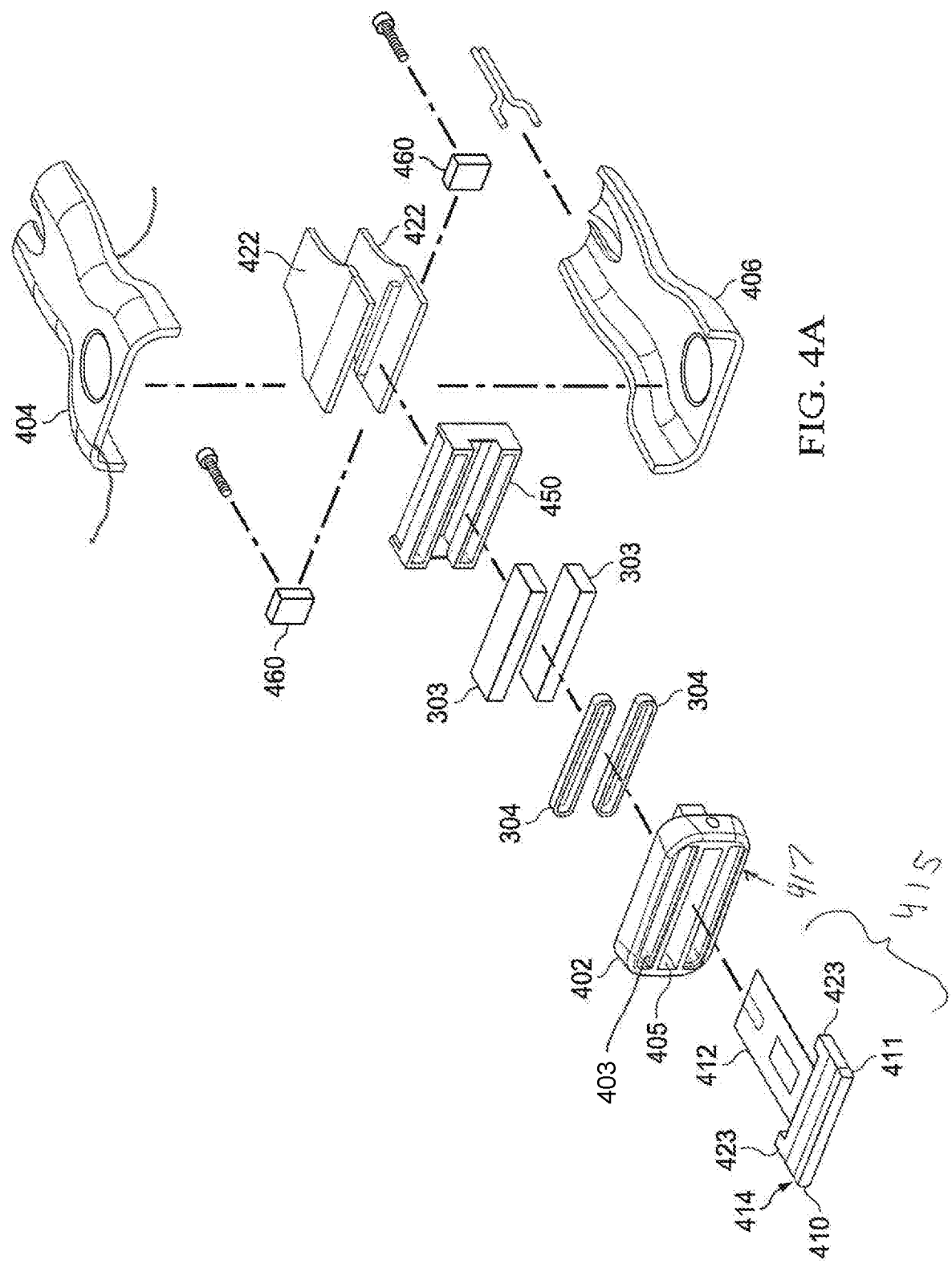
FIG. 4A shows an exploded view of an embodiment of the probe shown in FIG. 3.
Figure 4B:
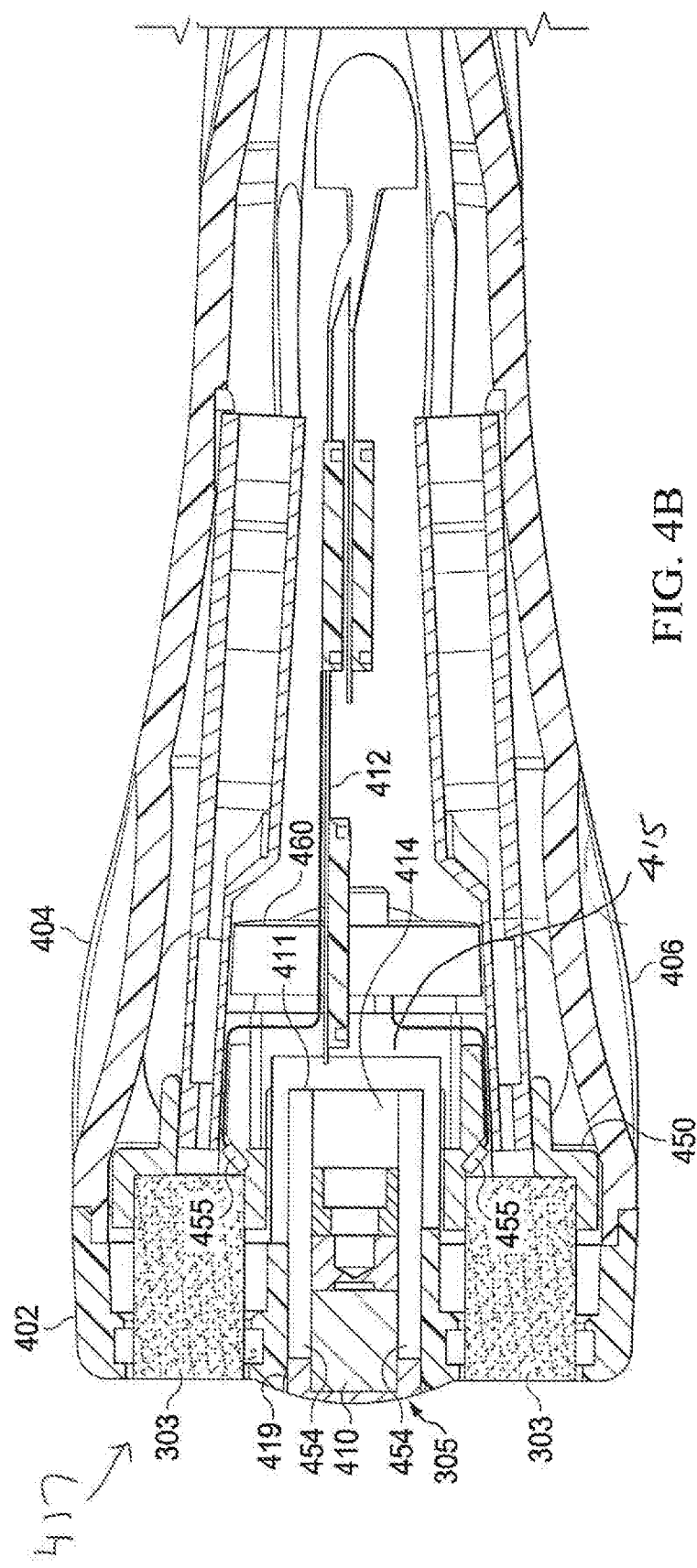
FIG. 4B shows a cross-sectional view of the probe shown in FIG. 3.

FIGS. 4A and 4B show an exploded view and a cross-sectional view, respectively, of an embodiment of the probe 102 shown in FIG. 3. In the embodiment of FIGS. 4A and 4B, the probe 102 comprises a housing 400 including a distal portion 402 and first and second body portions 404, 406 which are shown separated to illustrate the components within the probe 102. The distal portion 402 includes a probe face 417. The distal portion 402 and the first and second body portions 404, 406 may be made from plastic or any other suitable material. In an embodiment, one or more of those surfaces of the distal portion 402 and the first and second body portions 404, 406 that may be exposed to light, and especially light generated by the light subsystem 129, may be formed from a reflective material, for example, a light colored material, a light scattering material, for example, a material having a scattering coefficient between about 1 and about 10. In an embodiment, one or more of the surfaces of the distal portion 402 and the first and second body portions 404, 406 are highly reflective, for example, being characterized as more than 75% reflective, or being characterized as more than 80% reflective, or being characterized as more than 85% reflective. In an embodiment, one or more of the surfaces of the distal portion 402 and the first and second body portions 404, 406 are very highly reflective, for example, being characterized as more than about 90% reflective. Additionally or alternatively, in an embodiment one or more of the surfaces of the distal portion 402 and the first and second body portions 404, 406 have low optical absorption, for example, being characterized as less than 25% absorptive. In an embodiment, one or more of the surfaces of the distal portion 402 and the first and second body portions 404, 406 have very low optical absorption, for example, being characterized as less than about 10% absorptive. In addition, in an embodiment the material forming one or more of the distal portion 402 and the first and second body portions 404, 406 is acoustically absorbent to absorb, rather than reflect or transmit acoustic energy. In an embodiment, one or more of the distal portion 402 and the first and second body portions 404, 406 is white in color. Additionally or alternatively, in an embodiment, one or more of the distal portion 402 and the first and second body portions 404, 406 is formed from polybutylene terephthalate (PBT), $(C_{12}H_{12}O_4)_n$. Additionally or alternatively, in an embodiment, one or more of the distal portion 402 and the first and second body portions 404, 406 is formed from acrylonitrile butadiene styrene (ABS), $(C_8H_8)_x \cdot (C_4H_6)_y \cdot (C_3H_3N)_z$. Additionally or alternatively, in an embodiment the housing 400 may further comprise a sleeve into which the probe 102 may be fitted. In such embodiments, the sleeve may comprise a suitable material, for example, various plastic and rubber materials, effective to impart desired acoustic properties to the probe 102, such as acoustic absorbency.

Additionally or alternatively, in an embodiment the first and/or second body portions 404, 406 may include one or more regions that are characterized as acoustically reflective, for example, comprising an acoustically-reflective material.

In the embodiment of FIGS. 4A and 4B, the distal portion 402 and the first and second body portions 404, 406 collectively define the shape of the probe 102. In an embodiment, the distal portion 402 and the first and second body portions 404, 406 contribute to a shape that may be characterized as ergonomic, for example, having various contours enabling the probe 102 to be relatively easily and comfortably grasped by a user. For example, in the embodiment of FIGS. 4A and 4B, the probe 102 generally defines an external profile that is slightly tapered along the length of the probe and includes generally rounded surfaces. The external surface may also include grooves or concaved portions, for example, to provide for finger and/or thumb placement.

Figure 4C:
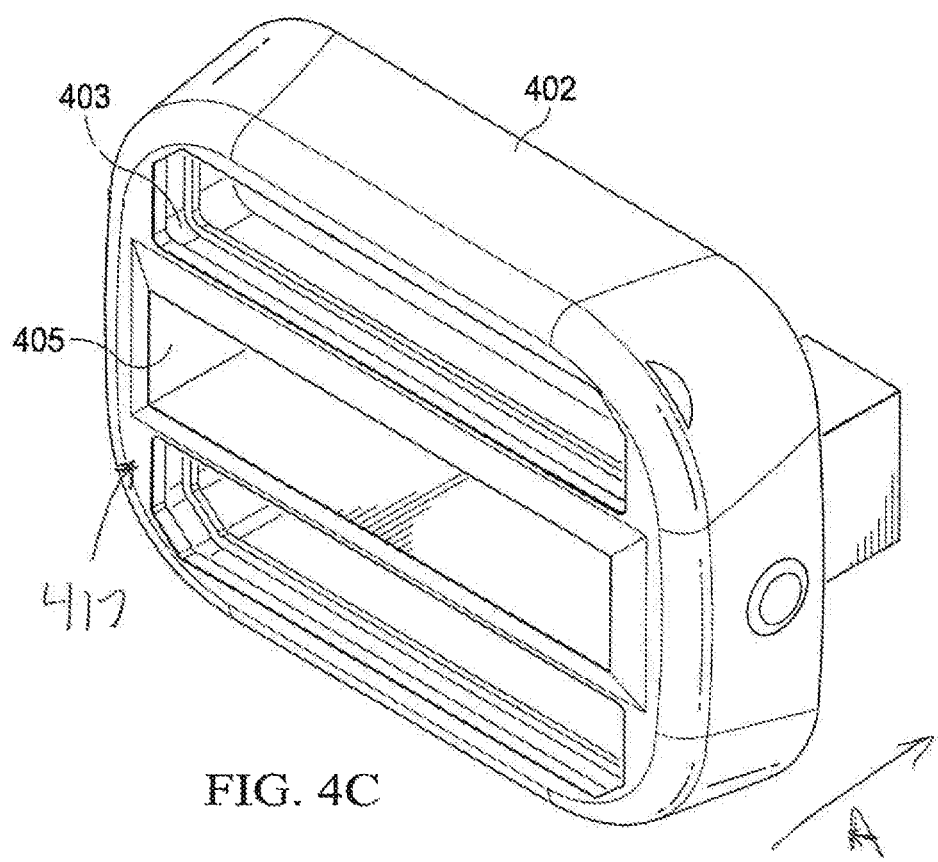
FIG. 4C shows a perspective view of an embodiment of the distal housing portion shown in FIGS. 4A and 4B.

Referring to FIG. 4C, the distal portion 402 of the housing is shown in a perspective view, in isolation. In the embodiment of FIG. 4C, the distal portion 402 has a probe face 417 that includes an acoustic opening 405 into which the transducer assembly 415 is disposed and one or more optical openings 403 into which the optical windows 303 are disposed. The transducer assembly 415 and the optical windows 303 extending proximally from the probe face 417 (in the direction of arrow A). For example, in the embodiment of FIG. 4C, the distal portion 402 includes two optical openings 403 into which two optical windows 303 are fitted and held on opposite sides of the transducer assembly 415. In accordance with embodiments herein, a optical barrier member is positioned to extend proximally from the probe face 417 between at least a portion of the optical window 303 and at least a portion of the transducer assembly 415. The optical barrier member may comprise one or more components as described herein.

The term "optical window," as used here, is not limited to an element having a particular structural, mechanical, or optical characteristic. Instead, the term is used to refer to an element that may or may not effect light passing therethrough, but will permit at least a substantial portion of the light incident on a surface of the optical window that is adjacent, or at least substantially proximate to the light path 132 to exit the probe 102 in a manner that is dependent on the properties of the optical window 303. In an embodiment, the optical window 303 is transparent or substantially transparent, permitting transmission of light, specifically, light emitted from the end of the light path 132, to the volume 160 when the distal end of the probe 102 is in contact with or close proximity to that volume 160. In an embodiment, the optical window 303 is translucent, permitting diffusion and/or transmission of light, specifically, light emitted from the end of the light path 132, to volume 160 when the distal end of the probe 102 is in contact with or close proximity to that volume 160. In an embodiment, the optical windows 303 comprise lenses, permitting the shaping and directing of light, and specifically light emitted from the end of the light path 132, to volume 160 when the distal end of the probe 102 is in contact with or close proximity to the volume 160. In an embodiment, the optical windows 303 are formed from a suitable material. For example, in an embodiment the optical windows 303 are formed from glass.

In an embodiment, the optical window 303 may be configured to diffuse the light received from the end of the light path 132. For example, in an embodiment the optical window may comprise a diffusive coating that is generally configured to cause the light applied to the optical window 303 from the light path 132 to be substantially diffused throughout the optical window 303. In an embodiment, the diffusive coating may be characterized as a holographic coating. In an embodiment, the diffusive coating may be characterized as exhibiting a high refractive index. In an embodiment, the diffusive coating is effective to cause the optical window 303 to reflect less than about 10%, or less than about 9%, or less than about 8%, or less than about 7% of the light applied to the optical window 303, for example, such that the optical window 303 is at least about 90% efficient, or at least about 91% efficient, or at least about 92% efficient, or at least about 93% efficient (and preferably as close to 100% efficient as practical).

Figure 4D:
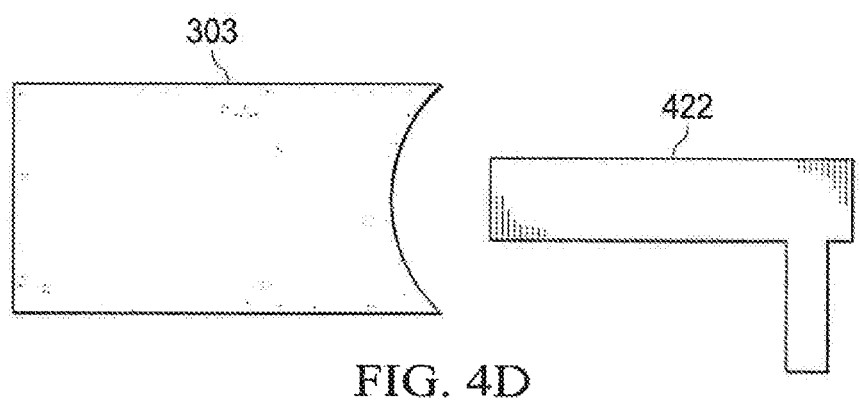
FIG. 4D shows a side view of an embodiment of an optical window.

Additionally or alternatively, in an embodiment the optical window 303 may comprise one or more surfaces configured to cause light incident upon the optical window 303 to be substantially diffused throughout the optical window 303. For example, referring to FIG. 4D, a side view of an optical window 303 is shown. In the embodiment of FIG. 4D, the optical window 303 includes a concave surface that is disposed proximate or adjacent to the end of the light path 132. In such an embodiment, light from the light path 132 may be incident upon the concave surface and the concave surface may cause the light received from the light path 132 to be substantially diffused through the optical window 303, for example, such that light is substantially uniformly emitted from the surface of the optical window 303 intended for contact with the volume 160. In another embodiment, the optical window(s) 303 may have a cylindrical shape with a concave surface on the side proximal to the end of the light path. With at least two rows of optical fibers providing light from the light path through the concave surface and cylindrical body of the optical window 303, the light may be substantially diffused such as to preclude the use of a diffusing coating on the optical window 303. The rows of optical fibers may be separated for uniform distribution of energy. For example, the concave surface and cylindrical body of the optical window 303 may diffuse the light from the light path 132 sufficiently, negating the use of other diffusing methods. In an embodiment, with an 8% loss in reflective energy in the diffuser as described above, the use of the optical window with a cylindrical body and concave surface may be more efficient than the optical windows with a diffuser coating. Optionally, an anti-reflective (AR) coating may be added to approach near 100% efficiency with no loss or substantially close to no loss.

In an embodiment, the optical window 303 is received within the distal portion 402 of the probe 102. For example, in an embodiment the optical window 303 may be supported within a groove in the distal portion 402 by a sealing gasket 304. During assembly, the sealing gasket 304 is inserted into a peripheral groove formed in the housing 400 and extending about the optical opening 403. For example, the sealing gasket 304 may be loaded from the proximal end towards the distal end and probe face (e.g. in a direction opposite to the arrow A). As illustrated in FIG. 4I, the sealing gasket 304 is shaped to include a raised rib 331 that extends about a perimeter of the sealing gasket 304 and is located proximate to a proximal end of the sealing gasket 304. The sealing gasket 304 further includes a flanged 335 extending along a distal edge of the gasket 304. The flanged 335 and rib 331 form a step there between. During the assembly process, the gasket 304 is loaded from the proximal end toward the distal end of the probe 102 by pulling on the flange 335 until the rib 331 is firmly seated within the groove 337. Assembly process further shapes the flange 335 to be flush with the probe face 417. For example, at an intermediate point during the assembly process, the flange 335 may be longer to have a distal edge that facilitates being pulled. Once the flange 335 has been pulled to fully seat the rib 331 in the groove 337, any portion of the flange 335 that extends beyond the probe face 417 is cut off. When fully seated into the groove 337, the sealing gasket 304 extends about the periphery of optical opening 403.

Optionally, in the assembly process, the optical window 303 may be loaded through the probe face 417 in the direction of arrow A (FIG. 4C). The optical window 303 is continued to be pressed through the gasket 304 until the distal portion of the optical window 303 is located proximate (e.g. flush) with the probe face 417. The sealing gasket 304 is inserted into the housing 400 and seated in the peripheral groove in the housing 400 before inserting the optical window 303. Once the sealing gasket 304 is in position, the optical window 303 is loaded through the probe face of the probe and through the sealing gasket 304 and a loading direction extending from the distal end towards the proximal end of the probe. The sealing gasket 304 may include a peripheral protrusion, for example, a flange, extending around exterior surface of sealing gasket 304. The peripheral protrusion may be sized and configured to engage a groove within the distal portion 402 of the probe. When the sealing gasket 304 is engaged with the groove in the distal portion 402, the sealing gasket 304 may form a compression and water seal in order to retain the optical window 303 within the distal portion 402 of the probe. The gasket 304 is sealed at a point flush with the probe face for cleanability and dis-infectability. The sealing gasket 304 is disposed within the optical opening 403 at the probe face 417 and extends at least partially around the optical window 303. The sealing gasket 304 is configured to form an optoacoustic barrier to at least partially optically and acoustically isolate at least a portion of the optical window 303 from the housing 400 of the probe 102. The term "optoacoustic barrier" is used to describe structures that optically isolate and acoustically isolate one structure from another by an amount sufficient to substantially improve performance and operation of the overall optoacoustic probe relative to conventional optoacoustic probes. The phrase "optically isolate", when referring to a particular structure, indicates that the corresponding structure prevents or substantially attenuates/reduces propagation of light through the corresponding structure. The phrase acoustically isolate", when referring to a particular structure, indicates that the corresponding structure prevents or substantially attenuates/reduces propagation of acoustic waves through the corresponding structure. The seal gasket 304 forms a physical barrier to separate the optical window from the housing of the probe. For example, boron nitride can absorb light and will not create sound when doing so. The sealing gasket 304 may be formed from a suitable material, for example, silicone. In an embodiment, the sealing gasket 304 may be characterized as a relatively high-tensile strength material, for example, such that the sealing gasket 304 resists tearing when pulled into position. More particularly, the sealing gasket 304 may be characterized as having an extremely high tear-strength, such that the sealing gasket 304 does not tear when inserting the optical window 303 through the opening in the sealing gasket 304.

In an embodiment, the sealing gasket 304 may be effective to reduce outgassing of one or more probe materials upon exposure to stray light or heat from the light path 132. The sealing gasket 304 is doped and/or filled with boron nitride. The boron nitride may be in any suitable form, for example, in an amorphous form, a hexagonal form, a cubic form, a wurtzite form, or combinations thereof. The boron nitride may be present within the sealing gasket 304 in a suitable amount. Boron nitride is thermally conductive but electrically isolated and thus affords a good dielectric barrier for safety. For example, in an embodiment, the boron nitride may be present in the sealing gasket 304 in an amount from about 1% to about 25%, or about 5%, by weight of the sealing gasket 304. Additionally or alternatively, in an embodiment the sealing gasket 304 further comprises a plurality of microspheres distributed within at least a portion of the sealing gasket 304. In an embodiment, the microspheres may include hollow shells made from phenolic, acrylic, glass, or any other suitable material. In an embodiment, the microspheres are small discrete, hollow spheres that have a diameter of several microns. The hollow space may include gases or may be substantially a vacuum. As used herein the term sphere (for example, a microsphere), is not intended to necessarily limit a structure to a particular shape, for example, a round shape, but rather, is used to describe a structure defining hollow space. A microsphere includes a shell surrounding a space which could be generally cubic, spherical, or any other suitable shape. In an embodiment, air bubbles or low-density particles may be incorporated into the sealing gasket 304 instead of, or in addition to, the microspheres, for example as microbubbles. In an embodiment, the microspheres, low density particles, or air bubbles may range in size from about 25 to about 500 microns. In an embodiment, the microspheres, low density particles, or air bubbles may range in size from about 50 to about 100 microns. In an embodiment, the composition of the sealing gasket 304 may range from 1% to 15% boron nitride and 2% to 25% microspheres, low density particles, or air bubbles and silicon may represent the remaining composition of the sealing gasket 304. The microspheres at the level of from 2% to 25% by weight of the gasket provide at least partial acoustic isolation, while the at least one of titanium dioxide and/or boron nitride at the level of 1% to 15% by weight of the gasket provide at least partial optical isolation. In an embodiment, the microspheres, low density particles, or air bubbles may be present in the sealing gasket in an amount from about 4% to about 6%, or about 5% by weight of the sealing gasket. Not intending to be bound by theory, the boron nitride may be effective to lessen stray light and/or, along with the glass microspheres, prevent unwanted ultrasound waves from transmitting into the housing 400 and/or into the transducer.

In an embodiment, the boron nitride is formed with a crystal structure that exhibits anisotropic thermal expansion properties. Due to the anisotropic thermal expansion properties of the boron nitride structure, when heated, the boron nitride molecules exhibit negative expansion in the "a" direction (with respect to the molecular lattice structure) and exhibit positive expansion in the "c" direction. By way of example, the boron nitride may be formed with a hexagonal or crystal structure. Due to the anisotropic thermal expansion properties of the individual boron nitride molecules, the overall boron nitride hexagonal or crystal structure exhibits low thermal expansion when heated due to exposure to light, due in part to the distribution and orientation of the boron nitride molecules within the overall crystal structure. Light emitting in a random manner upon the boron nitride may cause expansions and contractions that cancel each other, resulting in a low overall thermal expansion. For example, boron nitride may expand when light emits upon a longitudinal axis of the boron nitride. In another example, boron nitride may contract when light emits upon an orthogonal axis of the boron nitride. In another example boron nitride may react proportionally with some expansion and some contraction when light emits upon the boron nitride at an angle that includes at least some boron nitride molecules oriented along a longitudinal axis and at least some boron nitride molecules oriented along the orthogonal axis. In an embodiment, the boron nitride has a low-loss tangent, absorbing energy with no change in temperature. In accordance with the foregoing, the boron nitride absorbs heat without causing an acoustic wave front.

In an embodiment, the sealing gasket 304 may be doped with titanium dioxide ($TiO_2$). For example, one or more surfaces of the sealing gasket 304 may be coated with $TiO_2$ In an embodiment, the $TiO_2$ coating may increase the reflectivity of the sealing gasket 304 and may decrease leakage of light from around the optical window 303.

In an alternative embodiment, the distal portion 402 may include an optical cover which may be relatively thin, for example, an optically transparent plate such as a glass slide. The optical cover may be integrated directly into the distal portion 402, for example, fitted into the optical window opening 403. The distal portion 402 includes an optical cover 440 integrated within the distal portion 402 such that, when the probe 102 is assembled, the optical window 303 is disposed proximate or adjacent to the optical cover 440. In such an embodiment, light is transmitted via the optical window 303 and the optical windows 303 to reach the volume 160.

Referring again to FIGS. 4A, 4B, and 4C, in an embodiment the distal portion 402 is also configured to receive a transducer assembly 415. For example, in the embodiment of FIG. 4C, the distal portion 402 includes a transducer assembly opening 405 into which at least a portion of the transducer assembly 415 is fitted. The transducer assembly 415 may include the array of ultrasound transducer elements (not shown) forming the transducer 410. In an embodiment, the transducer 410 comprises at least 128 transducer elements, although it may be desirable to have a greater number of transducer elements, as additional elements may reduce distortion, and/or increase resolution, accuracy and/or depth of imaging of the device 100. In an embodiment, the ultrasound transducer comprises at least 128 transducer elements, for example, 256 transducer elements. The transducer elements may be piezoelectric elements.

In an embodiment, the transducer assembly 415 further comprises a flex circuit 412 comprising a plurality of electrical traces (not shown) electrically connecting cable connectors 414 to each of the transducer elements. The flex circuit 412 may be secured to a backing 411 of the transducer 410 using a bonding agent such as silicone or epoxy. The cable connectors 414 operatively connect the electrical traces, and thus, the transducer 410, to the electrical path 108. In an embodiment, the electrical path 108 includes a coaxial wire for each ultrasound transducer element in the transducer 410.

In an embodiment, the transducer assembly 415 further comprises a transducer isolator 418 that extends about the transducer 410. The transducer isolator 418 extends generally along a longitudinal length of at least a portion of the probe and along one or both sides of the transducer 410 along regions between the transducer 410 and the adjacent optical windows 303. The transducer isolator 418 configured to provide an optical barrier between the transducer 410 and the optical windows 303. The transducer isolator 418 may be generally configured to reduce the optoacoustic effect of light generated by the light subsystem 129 on the transducer isolator 418 and/or the transducer assembly 415. For example, in operation, light from the light subsystem 129 may escape from the light path 132 or may be reflected from, rather than absorbed by, the volume 160 such that the light may result in the generation of an unintended acoustic response by one or more components of the probe 102. Additionally, in operation, an acoustic response may also be unintentionally generated in the tissue by stray or escaped light. The stray light may create a signal from tissue that is out-of-plane with respect to the transducer and is undesired. In an embodiment, the transducer isolator 418 may be configured so as to absorb optical energy and/or to reflect optical energy, and absorb and/or reflect acoustic energy to prevent undesired acoustic signal from reaching the transducer, while still allowing acoustic energy generated by the target tissue to reach the transducer 410, for example, such that the ultrasound transducer will detect the optoacoustic response from the volume 160.

In an embodiment, the transducer isolator 418 is formed from or comprises a silicone rubber material, for example, a room-temperature-vulcanizing (RTV) silicon rubber. The RTV silicon rubber may have large acoustic impedance mismatch with respect to the transducer or a specific index of refraction to control light transmission. Additionally or alternatively, in an embodiment the transducer isolator 418 is formed from or comprises a synthetic rubber such as a polychloroprene (e.g., neoprene rubber), or a plastic (e.g., polyethylene).

In an embodiment, the transducer isolator 418 comprises a colorant. For example, the transducer isolator 418 may be doped with $TiO_2$, for example, as a colorant. In an embodiment, the transducer isolator 418 may comprise, for example, be doped, with from about 2% to about 25%, or approximately 4% $TiO_2$, by weight.

Additionally or alternatively, in an embodiment the transducer isolator 418 is formed from or comprises a foam material. The foam material may be formed from closed-cell foam, for example, comprising a solid material defining a plurality of discrete pockets or void-spaces completely surrounded by the solid material. The foam material may be characterized as having a highly porous, large void-volume, material with micro sized voids. Further, it may be characterized as having a low loss tangent and thermal expansion. In some embodiments, the foam material may be white in color. Additionally or alternatively, in some embodiments the foam material may comprise a colorant, such as $TiO_2$. Alternatively, in some embodiment the foam material may be black in color.

Additionally or alternatively, in an embodiment the transducer isolator 418 further comprises boron nitride. The boron nitride may be in any suitable form, for example, in an amorphous form, a hexagonal form, a cubic form, a wurtzite form, or combinations thereof. The boron nitride may be present within the transducer isolator 418 in a suitable amount. For example, in an embodiment, the boron nitride may be present in the transducer isolator 418 in an amount from about 1% to about 20%, or from about 5% to about 10%.

Additionally or alternatively, in an embodiment the transducer isolator 418 further comprises a plurality of microspheres distributed within at least a portion of the transducer isolator 418. In an embodiment, air bubbles or low density particles may be incorporated into the transducer isolator 418 instead of, or in addition to, the microspheres, for example as microbubbles. In an embodiment, the microspheres, low density particles, or air bubbles may range in size from about 10 to about 250 microns. In an embodiment, the microspheres, low density particles, or air bubbles may range in size from about 50 to about 100 microns. In an embodiment, the microspheres, low density particles, or air bubbles may be present in the transducer isolator 418 in an amount from about 25% to about 75%, or from about 40% to about 60%, or about 50%, by volume of the transducer isolator 418.

In an embodiment, the transducer isolator 418 may be applied to one or more surfaces of the transducer assembly 415. In the embodiment of FIG. 4E, the transducer isolator 418 is disposed proximate to or adjacent to a distal surface 421 of the transducer 410 and proximate to or adjacent to at least a portion of lateral surfaces 423 of the transducer 410. For example, the transducer isolator 418 may cover at least a portion of the probe face and/or side lateral surfaces 423 of the transducer 410 and/or the transducer assembly 415. In an embodiment, the transducer isolator 418 may be applied to the transducer 410 and/or the transducer assembly 415 in a suitable thickness (as measured in a transverse direction extending from the transducer 410). The transducer isolator 418 need not be applied uniformly to the various surfaces of the transducer 410 and/or the transducer assembly 415. For example, the transducer isolator 418 may be applied to the distal surface 421 in a first thickness and to the lateral surfaces 423 at a second thickness. In an embodiment, the transducer isolator 418 may have a thickness from about 0.1 inches to about 0.5 inches, or from about 0.2 inches to about 0.3 inches.

In an embodiment, the transducer isolator 418 may form at least a portion of the acoustic lens 305. For example, in the embodiment of FIG. 4E, a portion of the transducer isolator 418 is disposed over at least a portion of the distal surface 421 of the transducer 410. The transducer isolator 418 may be configured to allow acoustic energy to reach the transducer 410, for example, such that the ultrasound transducer will detect the optoacoustic response from the volume 160. Optionally, the transducer isolator 418 may be formed as an air gap extending along the region designated as 418, thereby performing isolation. Air gaps provide strong isolation from acoustic signals that may be generated within structures of the probe surrounding the optical windows.

Additionally or alternatively, in an embodiment the material disclosed with respect to the transducer isolator 418 may substantially cover the distal surface 421 of the transducer 410, for example, to form the acoustic lens 305. For example, in an embodiment, the acoustic lens 305 may comprise a carrier material (e.g. RTV silicon rubber) that includes an optoacoustic barrier material such as titanium dioxide, boron nitride, barium sulfate, aluminum dioxide, or combinations thereof. In some embodiments, the boron nitride is present in the acoustic lens 305 at a level from about 1% to about 10%, or about 5%, by weight of the material. In some embodiments, the titanium dioxide is present in the acoustic lens 305 at a level of from 4% to 6% by weight of the material In an embodiment, the acoustic lens 305 may comprise one or more additional layers of suitable materials, for example, multiple layers. In an embodiment, the additional layers may be applied over the distal surface 421 of the transducer 410. In an embodiment, the acoustic lens 305 includes a first layer covering the distal surface 421 may include parylene, for example, as a precursor for the application of one or more other layers. In an embodiment, the parylene may be Parylene C. In an embodiment, the parylene layer may be applied directly to the distal surface 421 of the transducer 410, for example, to the piezoelectric transducer elements. In another embodiment, the distal surface 421 is fitted with a Polytetrafluoroethylene (PTFE) layer, for example, a "Teflon" layer, and the parylene layer is applied to the PTFE layer.

In an embodiment, the acoustic lens 305 includes a second layer covering the distal surface 421. The second layer may include a tie-layer, for example, generally configured to tie layers adjacent to the tie-layer together. In an embodiment, the tie-layer may comprise a transition metal. For example, the second layer may comprise a relatively thin layer of chromium or nickel. The tie-layer may be applied to the first layer, for example, to the parylene layer.

In an embodiment, the acoustic lens 305 includes a third layer covering the distal surface 421. The third layer may comprise a thin layer of metal such as brass, aluminum, copper, gold, silver or combinations thereof. In an embodiment, the distal surface 421 is first coated with parylene, then coated with chromium, then coated with gold, then coated with diamond-like carbon (DLC). The multiple layers may provide a durable, multi-layer coating that is effective to reduce the effective of optical energy on the transducer 410 and without any substantial adverse effect to the acoustic properties of the acoustic lens 305, and without any substantial adverse effect to the transducer assembly 415 to detect acoustic energy. In an embodiment, the multi-layer coatings covering the distal surface 421 may also be covered by the transducer isolator 418.

In an embodiment, the transducer isolator 418 may comprise a distal-most surface, for example, a surface proximate to and covering the distal surface 421 of the transducer isolator 418, characterized as curved or arcuate. For example, the transducer isolator 418 may comprise an outer surface, for example, the distal-most surface, that is convex with respect to the transducer 410.

In an embodiment, the transducer isolator 418 may be configured to secure the transducer assembly 415 within the transducer assembly opening 405 of the distal portion 402 of the housing 400. For example, in the embodiment of FIG. 4E, the transducer isolator 418 includes a built-in O-ring 419 or lip extending around at least a portion of the transducer assembly 415 and having a diameter or width greater than the diameter or width of the remainder of the transducer assembly 415.

The O-ring 419 may be sized or otherwise configured to engage a complementary feature within the distal portion 402. For example, the distal portion 402 may include retaining feature such a groove, chamfer, or other depression into which the rim 419 fits such that the transducer assembly is held in place within the distal portion 402 of the housing 400. In operation within the probe, the O-ring 419 is compressed firmly to mechanically seal the acoustic lens 305 within the probe housing 400. Because there is no adhesive applied, this configuration allows the acoustic lens 305 to be replaced or upgraded, which in turn may extend the working life of the probe.

Figure 4F:
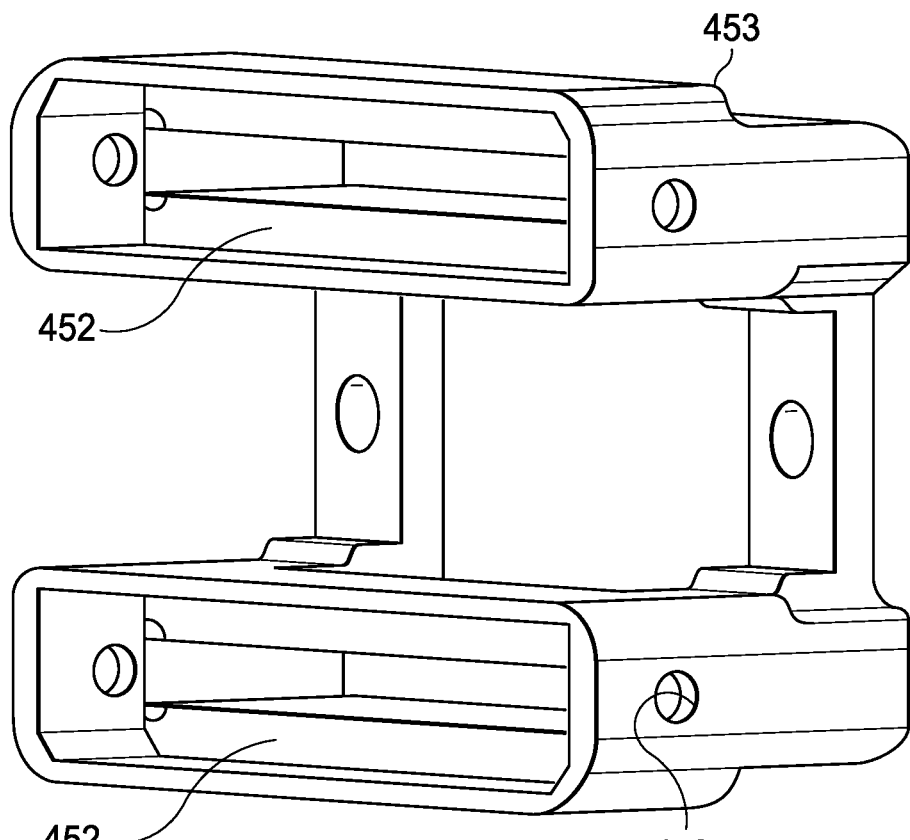
FIG. 4F shows a perspective view of an alignment bracket.

In an embodiment the probe 102 further comprises an alignment bracket 450. The alignment bracket 450 may be generally configured to retain the optical windows 303 within the probe 102 such that the optical windows 303 are held in a desired orientation. Referring to FIG. 4F, a perspective view of the alignment bracket 450 is illustrated. In the embodiment of FIG. 4F, the alignment bracket 450 includes optical window spaces 452. Each of the optical window spaces 452 is configured to securely receive one of the optical windows 303. For example, each of the optical window spaces 452 is configured to receive a proximal portion of one of the optical windows 303 therein. In an embodiment, the each of the optical window spaces 452 is configured to allow one of the optical windows 303 to be secured therein. For example, in the embodiment of FIG. 4F the alignment bracket 450 includes a plurality of threaded apertures 453, each configured to receive a set-screw or bond so as to secure the optical windows 303 with respect to the alignment bracket 450. In an embodiment, the alignment bracket 450 may be effective to ensure that the each of the optical windows 303 remains substantially in alignment with respect to the other optical window 303 and/or in a particular orientation with respect to the probe. For example, the alignment bracket 450 may hold the optical windows 303 in place such that the optical windows are substantially parallel and such that the optical windows are substantially parallel with respect to a longitudinal axis of the probe 102.

Figure 4G:
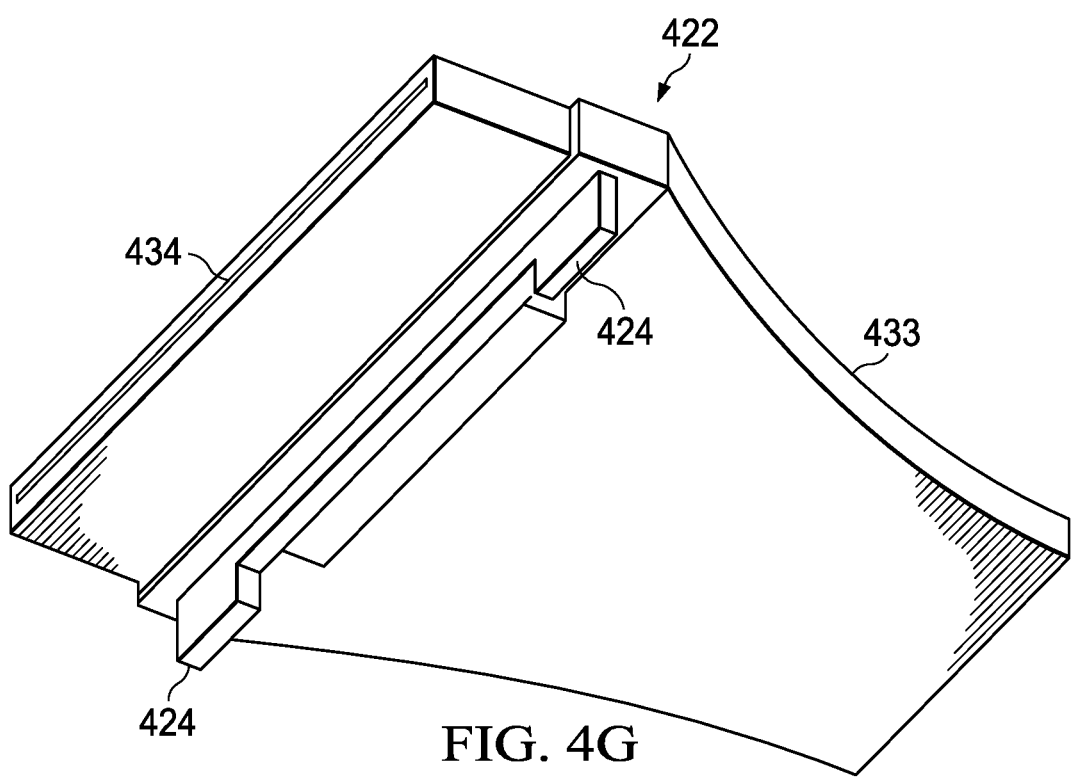
FIG. 4G shows a perspective view of a light bar guide.

In an embodiment, the alignment bracket 450 may also be generally configured to retain each of the optical windows 303 in proximity to a light bar guide 422. In an embodiment, the light bar guide 422 encases optical fibers that are part of the light path 132. Referring to FIG. 4G, a perspective view of the light bar guide 422 is illustrated in isolation. In the embodiment of FIG. 4G, the light bar guide 422 includes an optical fiber mounting slot 434 configured to receive the optical fibers and to retain the exposed ends of the optical fibers of the light path 132 in a desired alignment or orientation. In the embodiment of FIG. 4G, the light bar guide 422 also includes an optical fiber tray 433 configured to guide the optical fibers of the light path 132 away from the distal end of the light bar guide 422. The bracket 450 holds the optical window and transducer in alignment with respect to one reference point, and seals the air gap to prevent contamination from collecting in the air gap and then burning which would otherwise degrade the optics.

In an embodiment, the optical fibers making up the light path 132 may be randomly (or pseudo-randomly) distributed throughout the light bar guide 422, thus making specific locations on the light receiving end of the fiber optic bundle at least pseudo-random with respect to corresponding specific locations on the light emitting end of the optical fibers retained by the light bar guide 422. As used herein, reference to the optical fibers being randomly (or pseudo-randomly) distributed means that the mapping of fibers from the proximal end to the distal end is done such that a localized interference in the light path 132 (e.g., burnout of a group of adjacent optical fibers) or a localized phenomenon (e.g., non-uniform light at the entry point to the light path 132) will have an effect on the overall power transmitted, but will not have an operationally significant effect on any specific part of the distal end of the light path 132. Thus, two optical fibers adjacent at the proximal end are unlikely to be adjacent at the distal end of the light path 132. Where optical fiber bundles are fused at the proximal and distal ends, the randomization must be done before at least one end is fused. As used herein the term randomly (or pseudo-randomly) distributed optical fibers does not mean that two different light paths 132—that is, for different devices 100—must differ from each other. In other words, a single "random" mapping may be reproduced in the light path of different devices 100 while still meeting the criteria of being a randomized. Because light generally behaves in a Gaussian manner, the entry point to the light path 132 is typically less than perfectly uniform. Randomization, as discussed above, may accommodate for the non-uniform entry of light into the light path 132. Randomization may also provide homogenization of light fluence over area illuminated, as it may aid in more evenly distributing the light fluence.

In an embodiment, the optical fibers disposed within the optical fiber mounting slot 434 of the light bar guide 422 all end on substantially the same geometric surface, for example, a curved surface or a flat plane. In an embodiment, the fibers at the distal end, within a given light bar, may be grouped and sub-grouped in a manner that may help hold the fibers in position during manufacturing. Such grouping (such as in groups for the two light bars) and subgroupings (e.g., having subgroups per light bar) may further the even distribution over the geometric surface. Any number of subgroups may be used. In an embodiment, the number of subgroups is selected to be practical for fabrication and manufacturing. In an embodiment, the number of subgroups is selected to facilitate the manufacturing process. In an embodiment, the number of subgroups may be between 5 and 20, for example, about 15. In an embodiment, the fiber groups are formed by placing fiber subgroups between physical channels that are molded or machined into the light bar guide 422, for example, into its internal surfaces. Optionally, if the fibers can be physically distributed, the diffuser is not needed.

In an embodiment, after the fibers have been attached to the light bar guide 422, the fiber ends may be lapped and polished to provide for a more uniform angle of light emission. In an embodiment, the light bar guide 422, as installed in the assembled probe 102, directs the light emitting there-from at an angle normal to the distal probe face of the probe 102. In an embodiment, the distal end(s) of the light path 132 match, mirror, or closely approximate the shape of the acoustic transducer array.

The term bar, as used in "light bar guide" herein is not intended to import a specific shape. For example, the light bar guide 422 may guide the distal ends of optical fibers into substantially any shape such as, without limitation, a whole or part of a circle, oval, triangle, square, rectangle or any irregular shape.

Figure 4H:
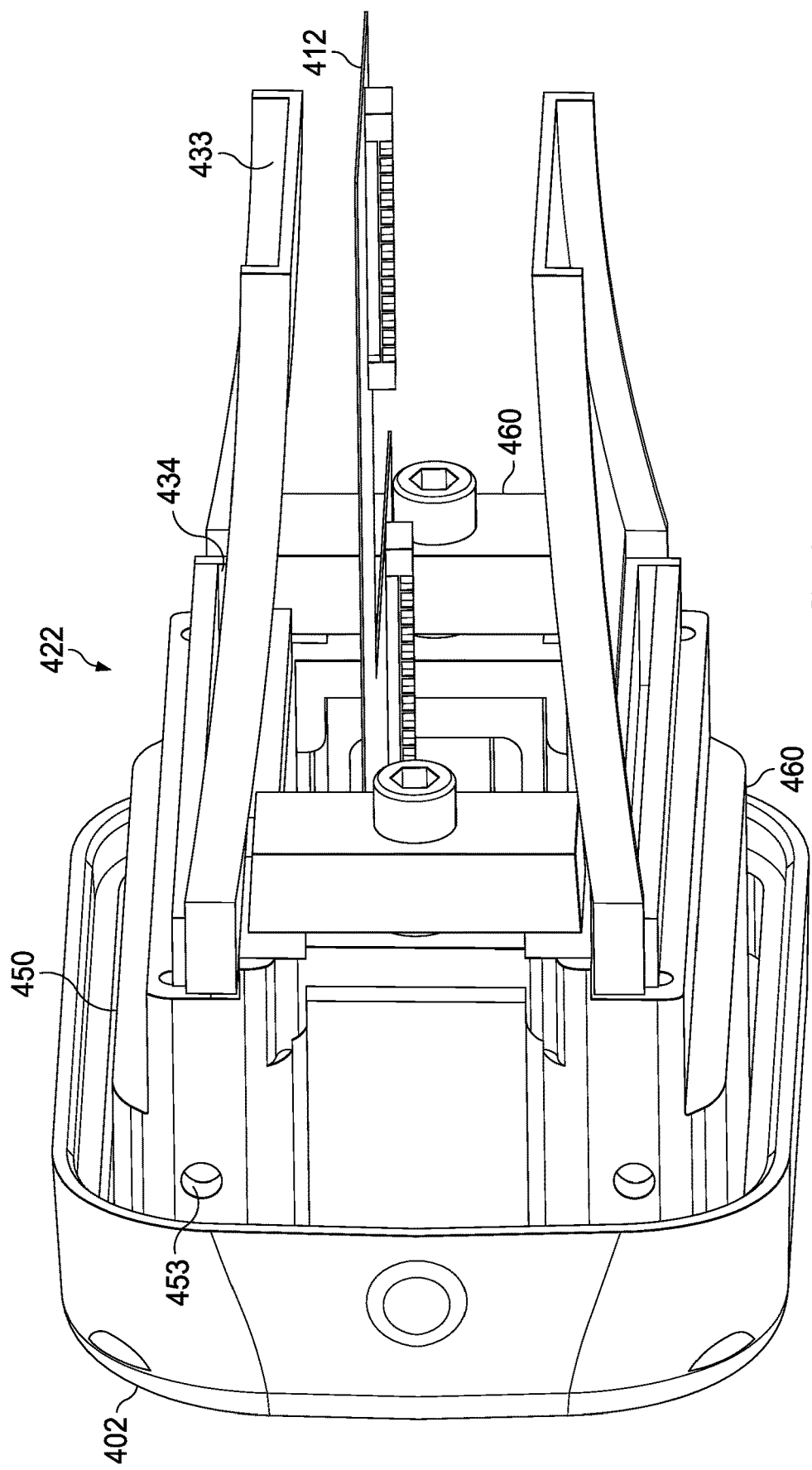
FIG. 4H shows a perspective view of the distal portion of the housing, the alignment bracket, and the light bar guides.
Figure 41:
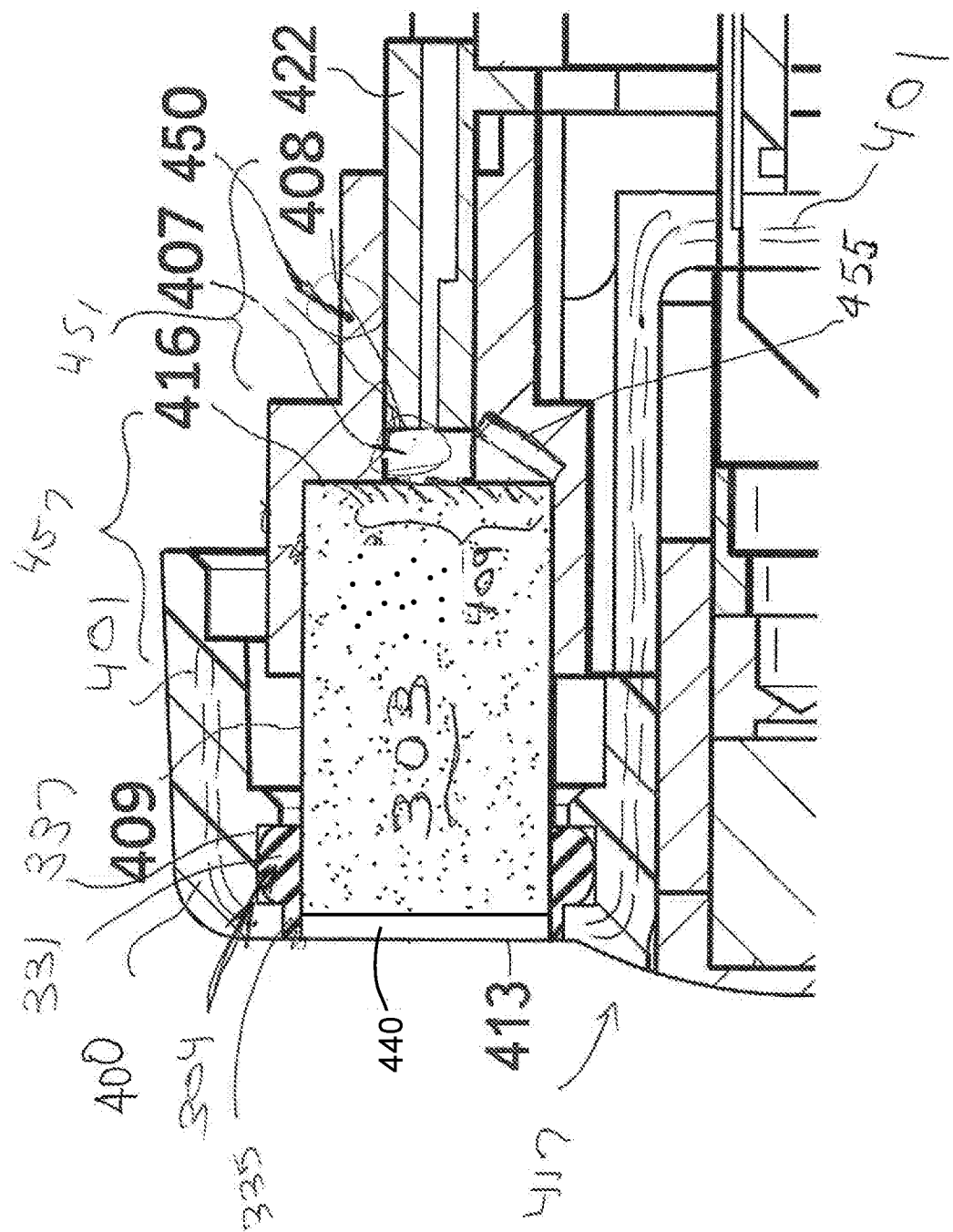

In an embodiment, the alignment bracket 450 may also be configured to hold the optical windows 303 in a desired proximity to the light bar guide 422, particularly, from the ends of the optical fibers making up the light path 132. As discussed herein, in an embodiment the alignment bracket 450 is configured to engage and retain the optical windows 303. In an embodiment, the alignment bracket 450 is also configured to hold the light bar guides 422 in a desired proximity to the optical windows 303. FIG. 4H illustrates a perspective view of the distal portion 402 of the housing 400, the alignment bracket 450, and the light bar guides 422. In the embodiment of FIG. 4H, the alignment bracket 450 and light bar guides are mechanically fixed to the distal portion 402. For example, in the embodiment of FIG. 4H, a clamping member 460 engages an inwardly-extending shoulder 424 on each of the light bar guides 422. The clamping member 460 may be mechanically-fixed to the alignment bracket 450 and the distal portion 402. Particularly, in the embodiment, the FIG. 4H, a plurality of machine screws extends through holes in the clamping member 460 and the alignment bracket 450 to engage threaded holes in the distal portion 402 and, thereby, to secure the light bar guide 422 and the alignment bracket 450 with respect to the distal portion 402. As such, the alignment bracket 450 may position the light bar guides 422 with respect to the optical windows 303. For example, the alignment bracket 450 may position the ends of the optical fibers held by the light bar guides 422 from the optical windows 303. In an embodiment, ends of the optical fibers are spaced from the proximal surface of the respective optical window 303. In an alternative embodiment, the ends of the optical fibers are adjacent to the proximal surface of the respective optical window 303.

When assembled, each of the respect the optical fiber trays 433 may extend inwardly from the engagement with the alignment bracket 450, for example, at an angle of about 3° from parallel to the longitudinal axis of the probe 102 (e.g., about 15° between each of the optical fiber trays). In an embodiment, the orientation of optical fiber trays 433, when assembled, may allow the housing 400 of the probe 102 to be relatively more compact and have improved ergonomics.

In an embodiment, the alignment bracket 450 may also retain the optical windows 303 in a desired proximity to with respect to the transducer assembly 415. In an embodiment, when assembled, the alignment bracket 450 fits within the distal portion 402 such that the transducer assembly 415 is spaced from the alignment bracket by gaps 454 on either side of the transducer assembly. In an embodiment, the probe 102 includes a light detector 455 disposed within each of the gaps 454. In various embodiments, the light detectors 455 may be effective to take measurements from which output energy can be estimated or deduced. In an embodiment, the light detector 455 will measure reflected energy such as energy reflected internally within the probe 102. In an embodiment, the light detector 455 will measure scattered energy. The measurement of the light detector 455 can be transmitted to the system chassis 101 via control path(s) 109, where it can be analyzed to deduce or estimate the light output of the probe 102. In an embodiment, control functionality in the system chassis 101 can control or regulate the light output of the light subsystem 129, and thus the light output of the probe 102 based on a measurement made by the light detector 455. In an embodiment, control functionality in the system chassis 101 can control or regulate the gain in the transducer receivers to compensate for variation of the light output of the probe 102 based on a measurement made by the light detector 455. In an embodiment, the computing subsystem 128 can trigger differing activity from light subsystem 129 over control signal line 106 based on a measurement made by the light detector 455. Additionally or alternatively, the light detector 455 may also measure light reflected from the tissue, for example, which can be used to determine amount of light entering tissue so that the system can adjust the light energy so as to maintain consistent light penetration across the different skin types. In an embodiment, a measurement made by the light detector 455 can be used to control for variations in the electrical system or the power to the device 100. Similarly, in an embodiment, a measurement made by the light detector 455 can be used to control for variations in the light path 132 or other optical elements of the device 100. In an embodiment, the light detector 455 can be used to cause the fluence of light output by the probe 102 to remain close to, but below, safe limits by accommodating for variations in electrical or optical characteristics that might otherwise cause the fluence of light output by the probe 102 to exceed or fall far below the safe limit.

The proximity of the optical windows 303 to the transducer assembly 415 allows light emitted from the optical window 303 to be emitted from a location close to the acoustic lens 305, and thus close to the plane of the transducer 410.

In an embodiment where the probe 102 has two optical windows 303, the angle of light emitting from both optical windows 303 can be adjustable, individually, or together. Where adjusting the angle of light emitting from the optical windows 303 together, the light direction would, in each case increase or decrease the angle of inward projection, that is, projection towards the plane normal to and intersecting the center of the transducer 410. In this manner, a larger light fluence can be directed deeper into the volume 160 (by angling toward normal), or shallower (by angling more inwardly).

Controlling the direction of the light angle can be done by moving the light bar guide 422, or it can be accomplished optically through the use of post-light path 132 optics. Optical solutions may include the use of one or more lenses and/or prisms to re-direct the light that has been transmitted through the light path 132, or by using an optical element having a variable index of refraction, such as, for example, an optical element having an index of refraction controlled in response to electric fields. Re-directed light can be directed to illuminate a desired area, such as an area directly beneath the transducer 410. Controlling the direction of light transmitted by the probe 102 is useful to maintain safe and optimize the direction of the light with respect to the skin and the transducers.

Also, in an embodiment the alignment bracket 450 may be effective to further impede an unintended optoacoustic response by a component of the probe 102. For example, the alignment bracket 450 may made from materials that reduce its optoacoustic response to light generated by the light subsystem 129. In an embodiment, the alignment bracket 450 is made from a material similar to the light contacting portions of the distal portion 402 and the first and second body portions 404, 406. As one example, the bracket 450 maybe Teflon coated.

In use, a coupling agent (e.g., gel) may be used to improve the acoustic contact between the distal end of probe 102 and the volume 160. If the coupling agent makes contact with the distal end of the optical fibers forming the light path 132, extraneous acoustic signal may be generated in response to light transmission over the light path 132. In an embodiment, the distal end of the probe 102, including optical window 303, mitigates the potential acoustic effect of a coupling agent in response to light emitting from the light path 132 by creating a gap between the coupling agent and the distal end of the optical fibers.

FIG. 4I illustrates an enlarged view of a distal portion of the probe 102. The probe 102 includes a housing 400 that includes the regions along which the double dashed line 401 extends. The housing 400 retains the sealing gasket 304 that holds the optical window at a select position and orientation within the housing 400. In an embodiment, one or more optical windows 303 may have a rectangular box-like shape, with a proximal end 416, one or more sides 409, and a distal end 413. The optical window 303 may be made of an optically transparent material, such as glass, polycarbonate, or the like. The distal end 413 is positioned adjacent to the probe face 417 of the probe 102 and may have an optical cover 440 provided thereover. The optical cover 440 may be made of an optically transparent material, such as glass, polycarbonate, or the like. A diffusion coating 413 is applied along at least a portion of the proximal end 416 of the optical window 303. As light enters the proximal end 416, the diffusion coating 409 evenly distributes light throughout the optical window 303. Optionally, a thin glass may used to seal in the housing at the exit, with the window located adjacent and no gasket is needed to seal.

The housing 400 includes a non-gassing (NG) support bracket 450 that define a non-gassing optical transition (NGOT) region located at an interface between the light path and a proximal end of the optical window. The NG support bracket 450 is configured to avoid producing out gas in a presence of heat due to light emitted from the light path. For example, the NG structural bracket 450 may be formed of aluminum or another non-gassing material. The bracket 450 includes proximal and distal sections 451, 457 that are formed in a role with one another. The proximal section 451 includes a passage therethrough that is configured to receive and retain at least a portion of the light guide 422. The distal section 457 includes a passage therethrough that is common with the passage through the proximal section 451. The passage within the distal section 457 is configured to support and retain the proximal end of the optical window 403. An optical transition zone 407 is formed at the proximal end 416 of the optical window 303. The optical transition zone 407 is located at an intermediate point between the proximal and distal sections of the bracket 450. The optical transition zone 407 represents an interface at which light, traveling along the light path enters the optical window 303. As nonlimiting examples, the optical transition zone 407 may correspond to an interface between a distal/discharge end of the light guide 422 and the proximal end 416 of the optical window 303. Alternatively, light guide 422 may be omitted entirely and the ends of the optical fibers positioned at the zone 407. In this alternative embodiment, the optical transition zone 407 would correspond to an interface between the distal/discharge ends of the array of optical fibers and the proximal end 416 of the optical window 303.

The aluminum bracket 450 encases the proximal end 416 and at least some of the one or more sides 409 of the optical window 303, while a distal end 413 of the optical window 303 projects outward beyond the bracket 450 and is held in the gasket 304. The distal end of the light bar 422 terminates at the optical transition zone 407. The Optical transition zone 407 is located at the interface between the optical fibers and the proximal end 416 of the optical window 303. The proximal end 416 of the optical window 303, the aluminum bracket 450, and the distal end of the light bar 408 may define an empty area or void as the optical transition zone 407, located between the optical window 303 and the light bar guide 422. When the optical transition zone 407 is formed as a void, the void may be air-filled. The optical transition zone 407 extends along at least some of the proximal end 416 of the optical window 303. The structural elements, that surround the optical transition zone 407, seal off the optical transition zone 407. The structural elements are formed of non-outgassing materials and therefore do not produce outgas even when heated by light that passes through the optical transition zone 407. In conventional approaches, as the light passed from the fiber to the optical window, stray light would enter the surrounding materials, heat the materials, and the materials would generate outgasses that would then condense and create a film or build up on the input/proximal side of the optical window 303. By isolating the optical transition zone 407 from any potential out gases generating materials, embodiments herein avoid coating buildup or a charring affect that could have been created otherwise if out gases were present in the Optical transition zone 407 and were heated until depositing material on surrounding surfaces. The light bar guide 422 comprises an optical fiber mounting slot 434 configured to receive the optical fibers of the light path 132. The aluminum bracket 450 seals the optical path between the optical window 303 and the light bar guide 422, encasing at least some of the optical window 303, at least some of the light bar guide 422, and all of the optical transition zone 407. In operation, for example, light emitted from the optical fibers contained within the light bar guide 422 passes through the optical transition zone 407. The optical transition zone 407 may represent a distance determined to provide an air-filled gap between the light bar guide 422 and the optical window 303. The aluminum bracket 450 may be configured to hold the optical window 303 in a position from the light bar guide 422 to achieve the desired optical transition zone 407, which results in a light path sealed by metal and glass. This configuration prevents stray light and outgassing on the proximal end 416 of the optical window 303 that may otherwise condensate and burn, reducing the efficiency of optical transmission. The emitted light may pass through the diffusing coating to disperse the light traveling through the optical window 303, resulting in a uniform distribution of light output. The diffused light may pass through the optical cover 440 to a patient's skin to provide desired light pulses required by the transducer 410 for proper optoacoustic results.

Figures 5A, 5B:
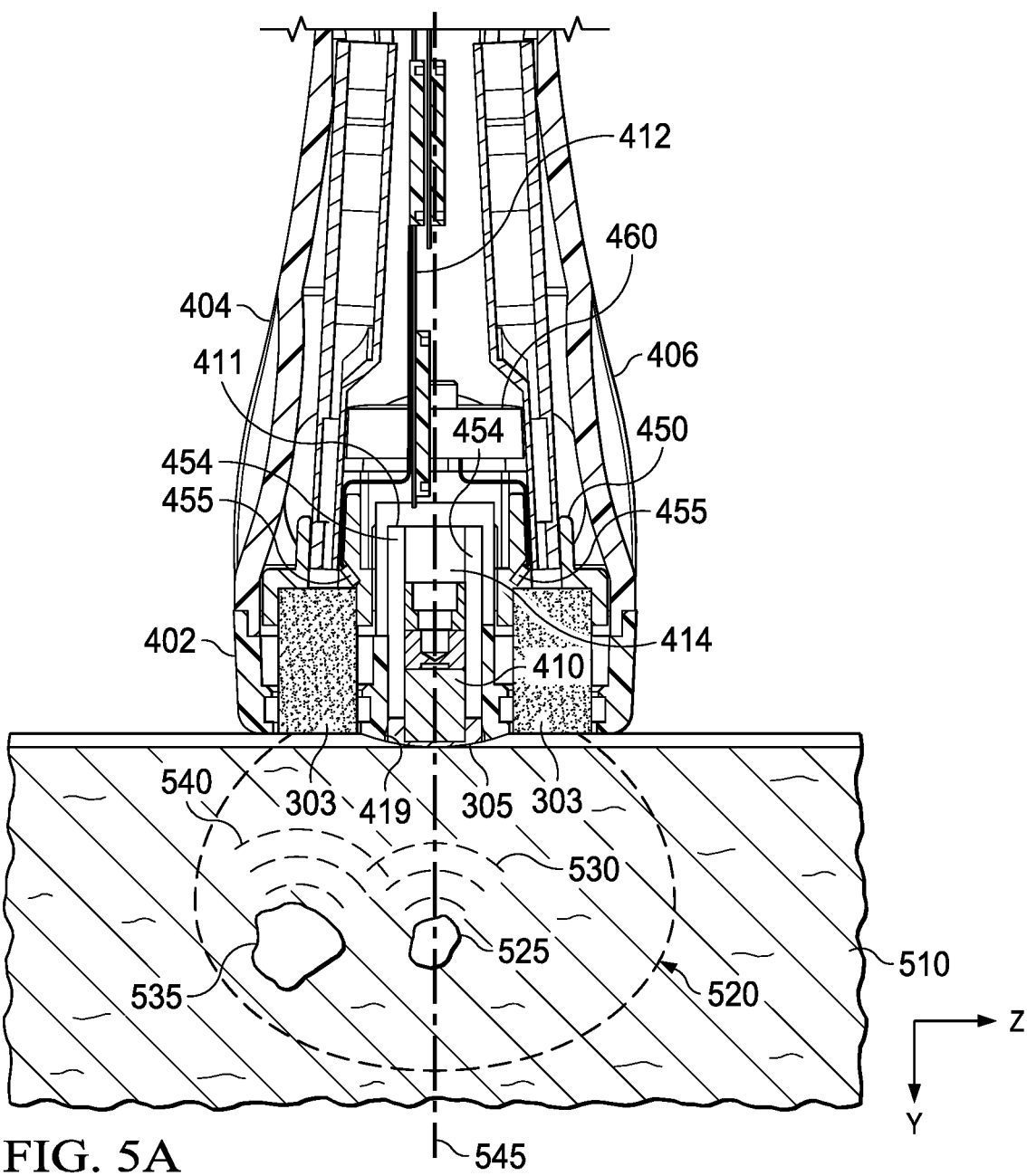
FIG. 5A shows an illustrative diagrammatic cutaway view of the probe shown in FIG. 3 with two optical beams and a single ultrasound transducer array.
FIG. 5B shows an illustrative diagrammatic view of a sectional view along the longitudinal length of the single ultrasound transducer array of the probe shown in FIG. 5A.

FIG. 5A shows a cutaway view taken along the centerline of the wider probe face of one embodiment of an assembled probe 102 such as the probe shown in FIG. 4. The distal ends of the optical fibers making up the light path 132 may be positioned such that they do not create a physical sound conduction path to the volume 160 or to the transducers 410. Specially selected materials, as discussed herein, can be used to ensure that the light bar guide 422 reduces and/or minimizes the physical sound conduction path between the distal end of the light path 132 and the volume 160 or the transducers 410.

An opening (not shown) in the first and second body portions 404, 406 provides an opening for light path 132, electrical path 108 and optional power and control path(s) 109 to enter the inside of the probe 102. In an embodiment, a rubber grommet (not shown) may be used to provide stability and strain relief to the paths or lines passing into the probe 102 through opening.

In an embodiment, the optical fibers may be positioned away from the surface of a volume to be illuminated. Moving the end of the optical fibers away from the surface of the volume to be illuminated will cause the beams emitted from each optical fiber to expand and produce a more uniform area of light distribution. One potential issue associated with moving the optical fibers away from the surface of the volume to be illuminated, is the optoacoustic effects caused by stray portions of the expanding beam. Another potential issue is the effect of enlarging the distance (between the end of the optical fibers and the surface to be illuminated) on the shape or size of a probe. Further, increasing the number of optical fibers (and thus enlarging the area of the fiber bundle emitting light) will increase the cost, weight and flexibility of the light path 132 (FIG. 1), and may also affect the size of the probe.

Because the probe 102 is designed to be handheld, it is desirable to keep the probe head (the wider, distal portion of the probe 102) short so that the probe's stem (the narrower, proximal portion of the probe 102) is relatively close to the surface of volume 160. Additionally, because the probe 102 is designed to be handheld, its total thickness is also a consideration for comfort, convenience and operational effectiveness. Accordingly, locating the distal ends of the fibers forming light path 132 at a sufficient distance from the optical window 303 to permit light expansion to fill the optical windows 303 with uniform light fluence is not preferred. Similarly, using a very large number of fibers to enlarge the area of the fiber bundle held by the light bar guide 422 at the distal end of the light path 132 and thereby attempting to permit light expansion to fill the optical windows 303 with uniform light fluence is also not preferred as it would, among other things cause undue weight, inflexibility, size and cost. Indeed, light expansion is a common undesired occurrence in existing probes. Moreover, reducing the size of the optical window 303 would reduce the total potential safe energy output of the device, and thus, is also not preferred.

In an embodiment, the light bar guides 422 are angled inward toward the ultrasonic imaging plane on the end retaining the distal ends of the fibers. The inward angling of the distal end of the light bar guide 422 permits the light emitting there-from to better fill, and thus, evenly illuminate the optical window 303. The inward angling tends to cause the direction of the light incident on the surface of the volume 160 to strike the surface at an angle less than normal, and thus, potentially, to better propagate into the volume 160 beneath the acoustic lens 305 covering the transducers 410.

Turning back to FIG. 1, because the probe 102 is intended for handheld use, the weight and flexibility of the light path 132, the electrical path 108 and the optional power and control path(s) 109 is of consideration. In an embodiment, to make the light path 132 lighter and more flexible, the light path 132 is constructed from as few fibers as possible. A limiting factor on the minimum number of fibers that can be used is the amount of light carried across the light path 132. The transmission of too much light over a fiber will damage the fiber. The light path 132 must carry the total amount of light that will be fluent on the surface of the volume 160, plus any light lost (e.g., absorbed or scattered) between the light subsystem 129 and the surface of the volume 160 illuminated. Since the maximum area of illumination is known not to exceed the size of the optical window 303, and because the area of illumination is subject to fluence limits per unit area, a total light energy carried by the light path 132 can be approximated by multiplying the fluence limit by the size of the optical windows 303.

In an embodiment, the number of optical fibers required for uniform distribution of energy may be determined based on a plurality of internal probe elements: (1) the geometry of the optical fiber bundle, (2) the properties of the diffuser (angles and optical damage), and (3) the length of optical window 303. The diffuser creates substantially totally internal reflection of light as it propagates through the optical window 303, thereby forming a homogeneous distribution of the light throughout the interior body of the optical window 303. First, in an embodiment, the geometry of the optical fiber bundles may include the diameter of the optical fibers and the shape of the fiber bundles. For example, optical fibers with smaller diameters may be more compliant than larger diameter optical fibers when bending. Also, smaller diameter optical fibers may be more compliant when determining a shape for the optical fiber bundle. For example, packing optical fibers in rectangular-shaped bundles in one or more rows may allow more illumination and uniform distribution of energy as well as reducing light expansion. Second, the properties of the diffuser that may be required for uniform distribution of energy may include using specific angles of the diffuser and choosing an optical window material based on an optical damage threshold. For example, in an embodiment, choosing a diffuser angle between 0° and 50° for diffuser height and between 0° and 20° for diffuser width may provide results that are necessary for uniform distribution of energy. In another embodiment, the optical window material may be chosen, based on a damage threshold, to be glass. Glass has a high damage threshold, which may be greater than 5 J/cm2. The high threshold is necessary for minimizing the length of the probe, as well as durability and efficiency. Third, in an embodiment, the optical fiber count necessary for uniform distribution may be based on the length of the optical window. For example, having a longer optical window will allow more fibers and accordingly more illumination. The length of the optical window depends on a combination of length, diffuser angle, and distribution of optical fibers at end of the optical fiber bundle. The length of the optical window may range from 10 mm to 20 mm and may be an array stretched longer than the acoustic transducer to avoid edge effects. In an embodiment, the width of the optical window may range from 3 cm to 5 cm. Diffraction properties of the optical window may be affected by differing widths. In an embodiment, the optical window may be formed of a single piece of glass. In another embodiment, the optical window may be formed with two or more pieces of glass. Also, in an embodiment, the uniform distribution of energy may exceed 85 mJ measured from the one or more optical windows.

In an embodiment, the width (A) of the optical window depends on the width of the transducer. In other words, the width of the optical window is a function of the width of the transducer (Tx width) as represented by the formula hereafter: A=F(Tx width). In an embodiment, the height (B) of the optical window depends on the number of diffuser angle in the glass of the optical window. In other words, the height of the optical window is a function of the diffuser angle as represented by the formula hereafter: B=F(diffuser angle). In an embodiment, the length (L) of the optical window depends on the number of diffractions in the glass of the optical window. In other words, the length of the optical window is a function of the number of diffractions as represented by the formula hereafter: L=F(# of diffractions). In an embodiment, the choice of glass (G) in the optical window depends on the desired index of refraction. In other words, the type of glass in the optical window is a function of the desired index of refraction as represented by the formula hereafter: G=F(index of refraction). In an embodiment, an energy density may be calculated by dividing the total light energy (E) by the area of the optical window (A·B). In an embodiment, the energy density must be uniform to reduce hot spots, ensuring safety for patients and probe operators, and the energy density must be less than a threshold established by the Food and Drug Administration (FDA). In an embodiment, the energy density threshold may be 20 mJ/cm² as represented by the formula hereafter: E/A·B<20 mJ/cm². The FDA provides numbers for the human safe level of fluence.

The volume 160 illuminated generally has its own optoacoustic response, which is especially apparent where light fluence is greatest, namely, at the surface of the volume 160. Increasing the area of illumination onto the surface of the volume 160 (e.g., by increasing the size of the optical window 303 and beam) reduces the optoacoustic affect generated by the surface of the volume 160 itself, and thus may reduce the undesirable optoacoustic signal generated by the surface of the volume 160 itself as compared to a desired signal representing the inhomogenities 161, 162.

In addition to unwanted optoacoustic signal generated by the surface of the volume 160 itself, there may be other sources of unwanted optoacoustic signals that can be detected by the transducers 410, such as the side walls surrounding the space between the optical windows 303 and the respective light bar guides 422, the acoustic lens 305 and portions of the housing 400.

In an embodiment, the walls surrounding the space between the optical windows 303 and the respective light bar guides 422 may be made from a material that has high acoustic absorption properties and/or that is white and/or has high light scattering and/or reflecting properties. Using materials having these characteristics may reduce unwanted optoacoustic signals that can be detected by the ultrasound transducer. In an embodiment, the light bar guides 422 can be made from a resin material such as Micro-Mark CR-600, a two part high performance casting resin that dries to a white color.

In an embodiment, a layer (not shown) of material that has high acoustic absorption properties and/or that is white and/or has high light scattering properties is placed between the transducer assembly 415 and the light bar guides 422 in the assembled probe 102. Alternatively, the layer may be applied directly to the transducer assembly 415 or the light bar guide 422 where the two parts contact in the assembled probe 102. This layer may reduce unwanted optoacoustic signals that can be detected by the ultrasound transducer. In an embodiment, the layer can be made from a resin material such as Micro-Mark CR-600, a two part high performance casting resin that dries to a white color. In an embodiment, the layer (not shown) may also comprise a reflective coating. In an embodiment, a reflective coating of gold is applied to the layer to reflect light that might otherwise strike the layer.

In an embodiment, anti-reflective coatings may be used to reduce the optoacoustic signature of the optical window 303 and/or the beam expander. In an embodiment, magnesium fluoride may be used as an anti-reflective coating on the optical window 303 and/or the beam expander. Anti-reflective coatings may be used to reduce and/or minimize energy absorbed or reflected by the optical window 303.

In an embodiment, the optoacoustic signature of the transducer assembly 415 and/or acoustic lens 305 can be reduced by whitening. In an embodiment, an acoustic lens 305 comprising RTV silicon rubber may be whitened and have its optoacoustic signature reduced by being doped with about 4% TiO₂. It is believed that the TiO₂ doping increases the reflectivity of the acoustic lens and therefore the absorption, and also has a scattering effect that tends to diffuse the optoacoustic response of the RTV silicon rubber, bringing the response down to a lower frequency which can be more easily filtered. As discussed above, the outer surface of the transducer assembly 415 and/or acoustic lens 305 may be given a metal coating, such as gold, copper, aluminum or brass. In an embodiment, the metal coating, and in particular, gold reduces the optoacoustic signature of the transducer assembly 415 and/or acoustic lens 305. It is believed that gold reduces the optoacoustic signature of the acoustic lens 305 because of its high reflectivity in the light spectrum. In an embodiment, the acoustic lens may not be whitened and may retain its natural color, or be colored differently to minimize optical absorption at one or more particular wavelengths. In an embodiment, the acoustic lens may be made of materials other than RTV silicon rubber, such as, for example, Buna-N rubber (i.e., nitrile rubber) or latex rubber.

As discussed above, the optical fibers at the end of the light path 132 are retained by the light bar guide 422 with all of the fiber ends retained by the light bar guide 422 located on substantially the same plane. In an embodiment, the fiber ends may be fixed in place using mechanical force, an adhesive, or a combination of mechanical force and an adhesive. The fibers may be glued near their distal end to keep them in the desired location and pattern, and/or to reduce output of mechanical energy due to laser firing. In an embodiment, the spaces between optical fibers fixed within the light bar guide 422 may be filled with a material having one or more of the following characteristics: sound absorbing, light scattering, white and/or light reflecting. In an embodiment, the optical fibers, which may be encased by a light bar guide 422 at the distal end of the light path 132 are fused. Fusing fibers at the distal end of the light path 132 may permit the light emitting from the light path to be more uniform.

In an embodiment, a reflective coating is placed on areas of the distal portion 402 and the first and second body portions 404, 406 where laser light emanating from the light path 132 may strike it, including with the assembled probe, and in the areas designed to make skin contact, e.g., near the optical window 303 and other portions of the distal end of the probe 102. In an embodiment, the distal portion 402 and the first and second body portions 404, 406 are coated in gold where laser light emanating from the light path 132 may, or is likely to strike it. In an embodiment, portions of the distal portion 402 and the first and second body portions 404, 406 may be made from gold, although at present this may be cost prohibitive.

In an embodiment, a proximity detector system (not shown) is used to determine that the distal end of the probe 102 is on or very near the surface of a volume. Among the reasons such a proximity detector system is desirable is that it can be used to prevent pulsing of the light subsystem 129 when the probe 102 is not in close proximity to a volume 160 under inspection, or to be inspected. This may be a safety issue as the light subsystem 129 may produce light at levels that can be harmful, e.g., to the eyes. The proximity detector system may be implemented in the form of: a mechanical contact switch at the distal end of the probe; an optical switch looking at reflections of a non-harmful beam from the surface of the volume 160; a conductive switch that is closed by contact with the volume 160 and/or any acoustic gel or other materials between the volume 160 and the distal end of the probe; a conductive switch and a standoff comprising a conductive surface for contact with the distal end of the probe 102; a conductive switch and a thin, optically and acoustically transparent, conductive surface applied to the surface of the volume 160 of interest; an acoustic transducer switch that can detect close proximity of the volume 160 by transmitting and looking for the reflection of a sound within a specific time; an acoustic transducer switch that can detect close proximity of the volume 160 by using a narrow shape sound transmitter and receiver and using the reflection to detect proximity; using one or more of the transducers in the transducer array as a proximity detector by looking for a signal return; or by operating the device 100 in an ultrasound mode and looking for an ultrasound image.

In an embodiment, a safety feature would prevent disconnection of the probe 102 from the flexible cable when the system is in operation (e.g. when the laser is firing). To implement this safety feature, in an embodiment, the device 100 can use control path(s) 109 to operate a mechanical lock on the connector between the probe and the flexible connector. In an embodiment, a fail-secure mechanical lock would only permit disconnection of the probe 102 from the flexible cable when a specific control path(s) 109 was at voltage greater than a prespecified amount.

As discussed above, the device 100 comprises a probe 102 that, in an embodiment, is capable of transmitting both ultrasound and light to a volume 160, and is capable of receiving and processing an ultrasonic response to the transmitted ultrasound and light. The ultrasonic response to the transmitted ultrasound is typically a narrow bandwidth around the transmit frequency, with a percent bandwidth of about 70% and having no meaningful response below 2 MHz, while the ultrasonic response to transmitted light is typically in a much broader range, such as the range of about 50 kHz to 20 MHz or more, typically centered in the range of 6 MHz to 8 MHz. In an embodiment, ultrasound is transmitted and received by the transducers 410, while light is transmitted by a light sources 130, 131, across the light path 132, and across the optical window 303 or other aperture, the ultrasonic response thereto is received by separate transducers (not shown) tuned to receive a select frequency range typically generated by the optoacoustic effect. The separate transducers are operated with high impedance amplifiers, e.g., having an impedance of more than 200 ohms, and preferably being about 500 ohms or more. Where the optoacoustic response is received by separate transducers, or by the same transducers using differing impedance loads from their use for ultrasound response, the signals representing the ultrasound response may be carried back to the system chassis 101 on separate wires of the electrical path 108 from the signals representing optoacoustic response.

In an embodiment, ultrasound is transmitted by the transducers 410, and the ultrasonic response thereto is received by the transducers 410, and light is transmitted by light sources 130, 131, across the light path 132, and out the optical window 303, and the ultrasonic response thereto is also received by the transducers 410. In such an embodiment, the transducers 410 are operated with high impedance amplifiers having an impedance of more than 1k ohms and less than about 100 k ohms, and more preferably between 2 k ohms and 10 k ohms input impedance. In an illustrative embodiment, the transducers 410 may be operated with a 5 k ohms input impedance amplifier.

In an embodiment, where the probe 102 is equipped with transducers 410 and separate transducers (not shown) tuned to receive the higher (vs. broader) frequency range typically generated by the optoacoustic effect, the optoacoustic response for light that is transmitted by light sources 130, 131, across the light path 132, and out the optical window 303, may be received by both the transducers 410 and by the separate transducers. Using both sets of transducers to receive ultrasound responsive to the optoacoustic effect may capture additional data that can be used to better analyze inhomogenities 161, 162 within a volume 160.

Advantages exist in connection with each of the differing transducer geometries discussed above. The straight linear array is compact, cost efficient, easily handled, and is the most commonly used in standard ultrasound B-mode imaging. The curved or winged linear arrays may conform better to the irradiated volume, and thus, provide better coupling. The non-linear (multiple row, also known as 1.5 dimensional) arrays permit additional angles from which to resolve the optical return signal from a given voxel, which may improve resolution and/or add clarity and contrast to the image and/or may better support three-dimensional imaging applications. Flexible arrays may also provide better coupling with the volume. The non-linear arrays can allow transducer elements that are optimized for ultrasound to co-exist with transducer elements that are optimized for optoacoustics within the same probe. Different transducer elements are used to create either the US or OA images.

An optoacoustic return signal can be generally acquired within a window of less than about 100 microseconds. Using a generally accepted approximation for the speed of sound in tissue of around 1,500 m/s, a 100 microsecond acquisition window may correspond to a depth of up to about 15 centimeters. In an embodiment, an optoacoustic return signal can be acquired within a window of about 65 microseconds, and contain information from as deep as about 10 centimeters. In an embodiment, the frequency of light events is anticipated to be generally on the order of every 50 to 100 milliseconds (0.05 to 0.1 seconds). Accordingly, the data acquisition may occur less than 1% of the time, and closer to between 0.1% and 0.2% of the time, leaving more than 99% of the time where no data acquisition is occurring. Electrical noise may be created by powering the light subsystem 129 and/or other components of the device 100. Accordingly, in an embodiment, to prevent electrical noise from affecting the data acquisition, a synchronization is utilized to prevent powering unnecessary components during that period, leaving power only to the preamps, analog-to-digital converters and multiplexer. In an embodiment, the synchronization between power and data acquisition allows for the power system to be optimally electrically quiet during the acquisition time period. In an embodiment, this may be achieved by powering down noisy digital components during this period or allowing charged capacitors to power the acquisition hardware at this time. In an embodiment, this is triggered by the same trigger that starts the acquisition cycle and is controlled by the master processor to control the turning on/off of the peripheral components not involved with the acquisition cycle. In an embodiment, this takes from a few nanoseconds to a few microseconds. In an embodiment, the same synchronization signal can be used to synchronize one or more of the other switching power supplies within and/or associated with the OA system. By controlling one or more such switching power supply, electrical noise produced by the power supply (e.g., switching transients) can be caused to occur at the same time. In an embodiment, by using a synchronization signal, electrical noise produced by the power supplies in the OA system can be purposefully staggered, leaving temporal windows of electrical quiet during which data may be acquired.

As discussed above, in an embodiment, the same transducers are used to receive acoustic-generated ultrasound and to receive the optoacoustic return signal. The geometry of acoustic-generated ultrasound transducers is not optimal for receiving the optoacoustic return signal. Accordingly, in an embodiment, separate transducers are used for the acoustic-generated ultrasound and the optoacoustic return signal. The acoustic-generated ultrasound transducers can have a narrower band because the transducer itself sends the signal that it needs to detect. The optoacoustic return signal transducer can have a wider band, such as, for example, 50 kHz to 20 MHz. This wider band is preferred, among other reasons, because gain falls faster with depth on the optoacoustic return signal. Thus, in an embodiment, a plurality of transducers is used to receive the acoustic-generated ultrasound and a separate plurality of transducers is used to receive the optoacoustic return signal. In an embodiment, the plurality of transducers used to receive the acoustic-generated ultrasound and the separate plurality of transducers used to receive the optoacoustic return signal comprise approximately the same number of transducers. In an embodiment, the plurality of transducers used to receive the acoustic-generated ultrasound and the separate plurality of transducers used to receive the optoacoustic return signal each comprise at least 128 transducers, and more preferably, would comprise at least 192 transducers. In an embodiment, the plurality of transducers used to receive the acoustic-generated ultrasound and the separate plurality of transducers used to receive the optoacoustic return signal each comprise at least 256 transducers. In an embodiment, the transducers used to receive the optoacoustic return signal have a wider band frequency response than separate transducers used to receive the acoustic-generated ultrasound. In such an embodiment, the transducers used to receive the optoacoustic return signal have a frequency response from at least about 1 MHz to 5 MHz, and more preferably, from about 100 kHz to about 10 MHz, and even more preferably from about 50 kHz to about 20 MHz. In such an embodiment, the transducers used to receive the optoacoustic return signal may use high impedance amplifiers, such as 1 kΩ or more, and more preferably, 5 kΩ or more. In such an embodiment, the transducers used to receive the acoustic-generate ultrasound would use amplifiers having an impedance of less than 1 kΩ and more preferably about 200Ω. The use of separate transducers would eliminate the need for relay system 110, and the switching of the transducer outputs thereby between the optoacoustic processing and overlay system 140 and the ultrasound instrument 150.

As discussed above, in an embodiment, the same transducers are used to receive acoustic-generated ultrasound and to receive the optoacoustic return signal. Where the same transducers are used to receive acoustic-generated ultrasound and to receive the optoacoustic return signal, amplifiers should be used that have an input impedance value within the range of about 1-10 kΩ, and more preferably amplifiers should be used that have an impedance of approximately 5 kΩ.

In an embodiment, the sampling of an optoacoustic return signal is performed in a variable manner, where the gain of the amplifiers associated with each of the sampled channels is adjusted over time, and is hereinafter referred to as time gain compensation or TGC. TGC ramps up gain on the acoustic input as the optoacoustic return signal becomes fainter, thus more accurately sampling the signal, and providing more normalized collected data and maintaining good signal-to-noise ratio as the signal become fainter. Optoacoustic return signal becomes fainter with time for several reasons, including that the later optoacoustic return signals have generally traveled further. Thus, generally optoacoustic return signal becomes fainter as the depth of a target increases. However, the magnitude (and thus needed gain) of optoacoustic return signals are also affected by the location and source of illumination. Generally, less light penetrates to deeper depths, and thus, the optoacoustic return signals are fainter because an optoacoustic event occurring at the surface of a volume generally induces a smaller response at a deeper depth. TGC is utilized to compensate for the later, fainter optoacoustic return signals.

The device 100 may comprise sensors (not shown) that can measure power and from that infer both total and peak power of the light subsystem 129, and performance and efficiency of the light path 132. In an embodiment, sensors, for example, photodetectors such as light detectors 455, can be placed within or in close proximity to the light subsystem 129 and within or in close proximity to the probe 102. In each case, the sensors would take a measurement during the illumination of a light sources 130, 131 which can be used to infer total and peak power. For this purpose, one or more light detectors 455 can be placed inside the probe 102 to measure reflection from the optical window. Similarly, one or more light detectors 455 can be placed within the light subsystem 129 to measure light reflected therein. Deviation over time in the measurements inferred between the two sensor locations may be indicative of anomalies in the light path 132.

Discussing now an embodiment of the system having light detector 455 such as photodetectors within or in close proximity to the probe 102. In an embodiment, one or more light detectors 455 may be placed within the probe, in the gap 454 to measure reflection from the optical window. Alternatively, or additionally, in an embodiment, one or more light detectors 455 may be provided light directly from a component of the light path 132, such as from one or a small plurality of the optical fibers that make up the light path 132. Alternatively, or additionally, in an embodiment, one or more light detector 455 may be provided light by another path provided within the probe. Thus, for example, one or more light detectors 455 could be located within the end of the probe opposite the optical windows 303, and an auxiliary light path can e.g., carry light directly from the light path 132 or reflected from the optical window or otherwise, to the one or more light detectors 455. Alternatively, or additionally, in an embodiment, one or more light detectors 455 may be arranged to detect light originating in the light path 132 after it has been reflected from the surface of volume 160. Using information from sensors arranged to detect light reflected from the surface of volume 160, in combination with information concerning the light transmitted through the optical window 303 towards the volume 160 (such as information from sensors measuring output from the light subsystem 129 or from the optical window 303), can provide diagnostic information concerning the volume 160. Such diagnostic information may include the absorptiveness, or the darkness, of the volume 160.

In an embodiment, the foregoing light detectors 455 can be tuned to specific wavelengths through the use of an optical filter. Thus, for example, light detectors 455 within or in close proximity to the probe 102, light detectors 455 within or in close proximity to the light subsystem 129, light detectors 455 receiving light from an auxiliary light path and/or sensors arranged to detect light reflected from the surface of the volume 160, can be filtered to discriminate between the wavelengths of light produced by the light subsystem 129 and/or any extraneous light. Accordingly, sensors may be provided to detect (or potentially to reject) specific light frequencies, such as the light from one of the two light sources 130, 131.

In an embodiment, one or more light detectors 455 within or in close proximity to the probe 102 can be used as part of a triggering system and method for starting detection optoacoustic return signal data. In such a triggering system or method the detection of a specific threshold value of light by the one or more light detectors 455 can send a detection control signal to the computing subsystem 128. In an embodiment, the detection control signal is sent over the power and control path(s) 109 to the optoacoustic processing and overlay system 140. The detection control signal is used by the computing subsystem 128 to initiate (after any appropriate delay, if any) the process of obtaining the optoacoustic return signal data, for example, by "sampling" data from the ultrasound transducer elements. As discussed above, because the one or more light detectors 455 can be optically filtered to detect specific light frequencies, the detection control signal may be specific to one or more frequencies of light, and may initiate differing sampling rates, or delays, based upon the different frequency of light.

In an embodiment, one or more light detectors 455 within or in close proximity to the probe 102 can be used as part of a system and method for safely starting the device 100 and then bringing the laser to its safe power potential. Although laser light sources (e.g., 130, 131) generally have a controllable power output, many factors can affect the total power output by a light source regardless of its setting. Ambient temperature, for example, may affect the power output by a laser. Similarly, fluctuations in electrical power can also affect the power output by a laser. In addition, the light path 132 can negatively affect the light output of laser light sources (e.g., 130, 131). Fibers within the light path 132 can burn out or lose transmission properties as they age or are used. Moreover, fibers that are positioned in a bend can lose transmission properties. Thus, the setting of a light source (e.g., 130, 131) to a particular output level is not necessarily determinative of the light that reaches the other end of the light path 132, and ultimately, the volume 160. Accordingly, in an embodiment, the light source (e.g., 130, 131) is set to a relatively low power. The relatively low power should be selected to be a power which, in the event everything is functioning at its peak output or conductivity, would not exceed a desired maximum fluence on the volume 160. Once the light source (e.g., 130, 131) is pulsed, a measurement from the one or more light detectors 455 is used to infer the fluence of light delivered to the volume 160. In the event that this inferred fluence is lower than the desired fluence level (or a desired range of fluence levels), the output from the light source can be increased, and the process repeated. Likewise, in the event that the inferred light fluence is higher than a desired maximum, the output from the light source can be decreased. Because the device 100 is capable of a significant number of laser events per second, the rate of increase to the light output, and thus, the potential increase in the fluence level between laser events, can be kept relatively small. In an embodiment, the amount of change in output from the light source may be larger when the inferred fluence is farther away from the desired fluence level (or a desired range of fluence levels), and smaller when the inferred fluence is closer to the desired fluence level.

In addition to providing a method for safely starting the optoacoustic system and bringing the laser to its safe power potential, the same process can be run as a closed loop control to ensure that the laser fluence is being monitored and controlled, and that to the extent it exceeds a predefined threshold such coming within some margin of a safety limit, its output power can be lowered. Similarly, operating the process as a closed loop control can also ensure that the laser output is being set to a maximum desirable setting even as the operating conditions of the device 100 (e.g., ambient temperature and electrical power) change, and regardless of the existing or changing condition of the light path 132. Keeping the laser at or close to its highest safe level permits the largest light fluence, and thus, strongest optical return signal. In an embodiment, one or more of the following: the target fluence level, the acceptable hysteresis around the target fluence level and a maximum fluence level, are user selectable, and when selected can be used by the processing running as a closed loop control to maintain the laser as specified. The closed loop control process can be used to normalize pulse-to-pulse power output.

In an embodiment, where the measurement taken at the one or more probe-proximate light detectors 455 falls below a predetermined threshold for a given laser output, as a failsafe, the lasers may be shut down. Such a level may reflect a failure or detachment of the light path 132, or other unsafe condition.

In an embodiment, having one or more light detectors 455 within or in close proximity to the probe 102 and one or more light detectors 455 within or in close proximity to the light subsystem 129, the light detectors 455 can be utilized as part of a system for and method to detect faults in the light path 132 or to provide a safety control for faults in the light path. In an embodiment, the light output of the light subsystem 129 would be expected to be proportional to the light output of the light path 132 and the light fluence exiting the optical windows 303. The use of one or more light subsystem-proximate sensors can permit detection of differences in the expected amount of the light incident on the several light detectors 455. As discussed above, the light path 132 can negatively affect the light output by of laser light sources (e.g., 130, 131). For example, the light path 132 can be negatively affected by burn out, old or broken fibers within the bundle. Thus, setting a light source (e.g., 130, 131) to a particular output level is not necessarily determinative of the light that reaches the other end of the light path 132, and ultimately, the volume 160. By employing both one or more light subsystem-proximate sensors and one or more probe-proximate light detectors 455, performance of the light path 132 can be detected and monitored.

In an embodiment, the one or more light subsystem-proximate light detectors 455 are used to measure the power of the light entering the light path 132 and one or more probe-proximate light detectors 455 are used to measure the power of the light that has been transmitted through the light path 132. The measurement taken at the one or more light subsystem-proximate sensors may be used to predict a measurement at the one or more probe-proximate light detectors 455. In an embodiment, deviation from the predicted measurement at the one or more probe-proximate light detectors 455 can be used to identify potential problems with the light path 132. In an embodiment, the sensor readings are recorded with other data concerning the event. In an embodiment, deviations are assessed to determine whether action needs to be taken, for example, whether the user needs to check the light path 132 connections, or whether the light path 132 is in need of maintenance (e.g., straightening, cleaning, lapping and polishing or other maintenance) or even replacement. In an embodiment, where the measurement taken at the one or more probe-proximate light detectors 455 deviates from its predicted measurement by more than a predetermined amount, as a failsafe, the lasers may be shut down. Such a deviation may represent a failure or detachment of the light path 132 or other fault or unsafe condition.

In an embodiment, having one or more light detectors 455 within or in close proximity to the probe 102 and/or one or more light detectors 455 within or in close proximity to the light subsystem 129, the measurements from the sensors, along with the other settings of the machine (including the commanded light output) should be stored with the data other data associated with the light pulse, such as the optoacoustic return signal. In operation, the probe 102 includes a light detector 455 disposed within the one or more airgaps 407. In various embodiments, the light detectors 455 may take measurements from a given subsystem from which output energy can be estimated or deduced, such as the one or more optical windows 303. In an embodiment, the light detector 455 measures reflected energy within the probe 102. In an embodiment, the one or more optical windows 303 may reflect at least some energy from the optical path. The reflected energy from the one or more optical windows 303 may be measured by the light detector 455. The measurement of the light detector 455 can be transmitted to the system chassis 101 via control path(s) 109, where it can be analyzed to deduce or estimate the light throughput of the probe 102. In an embodiment, the measurement of the light detector 455 may be utilized to estimate the probe transmission. Additionally or alternatively, the light detector 455 may also measure light reflected from the tissue, for example, which can be used to determine an amount of light entering tissue so that the system can adjust the light energy so as to maintain consistent light penetration across different skin types. In an embodiment, the adjusting of the system results in a real-time calibration of the probe. In an embodiment, a measurement made by the light detector 455 when the probe is not in contact with a patient measures the transmission efficiency of the system. For example, measurements taken when a probe is new are compared to real-time measurements of a probe in use, resulting in constant feedback regarding efficiency and degradation of the probe and its optical components. Thus, a probe can be replaced before probe failure or inefficiencies that may cause readings outside of accepted parameters. In an embodiment, a measurement made by the light detector 455 when the probe is in contact with a patient measures reflectance energy. Total energy and reflectance may be measured using data from the one or more optical windows 303.

In an embodiment, information associated with a probe's own response characteristics may be stored within the probe itself and can be reported to the optoacoustic processing and overlay system 140 via power and control path(s) 109. In an alternative embodiment, information associated with a probe's own response characteristics may be stored outside the probe and can be associated with a serial number or other identifier of the probe. The optoacoustic processing and overlay system 140 can obtain the probe response characteristics after identifying the probe for use. In an embodiment, the probe response characteristics may be stored in a network accessible location, either on a local disk, network, or on the Internet, and are made accessible to the optoacoustic processing and overlay system 140 via a connection (not shown) to that disk, network or the Internet. In an embodiment, the optoacoustic processing and overlay system 140 would obtain a unique identifier from the probe and would thereafter query a database on the local device, network, or over the Internet, to obtain response characteristics for the probe associated with the unique identifier. Probe response characteristics may be recorded and stored at or near the time the probe is manufactured. In an embodiment, probe response characteristics may be updated by running a specialized test on the probe—the test having a known/expected response.

The probe identifier may be obtained by the optoacoustic processing and overlay system 140 after machine startup, but before engaging the light output. In an embodiment, the probe identifier is recorded on a bar code on the probe, and the bar code is scanned prior to the device causing light output. In an embodiment, the probe identifier is recorded on a computer-readable memory in the probe, and is queried by, or reported to the optoacoustic processing and overlay system 140 after startup, but prior to engaging the light output.

Because the probe identifier is known, the device can maintain statistics of probe usage. For example, in an embodiment, the device may maintain statistics of the operation of the probe in optoacoustic mode, including, e.g., the number and type of light output events that have occurred, and the number of ultrasound events that have occurred. Statistics can also be maintained concerning total light energy output from the probe (which may be deduced from an internal optical sensor, not shown). In an embodiment, the response characteristics of the probe and the probe statistics can be available to any device 100 on which the probe 102 is mounted. Thus, for example, such characteristics and statistics can be stored in a manner that they are accessible over the Internet. In an embodiment, a VPN is used for security on the Internet.

In an embodiment, where the light path 132 is fixedly attached to the probe 102, the probe usage statistics may also be relevant to the fiber optics. For example, the fibers in the light path 132 may degrade with time and/or use resulting in some loss of transmission, e.g., broken or burned fibers. Accordingly, in an embodiment, the device can maintain statistics relevant to total light energy, peak light energy and the number of pulses passed through a light path 132. In an embodiment, sensors in the probe can detect information about the energy output of the light path, and sensors in the light subsystem 129 can detect information about the energy output of the light subsystem 129. By detecting variation in the sensors at the two ends over time, maintenance issues can be identified. For example, seeing a decrease at the probe-side sensors relative to the light subsystem-side sensors may indicate that the light path 132 is degrading and needs replacement. Moreover, a specific difference between the probe-side sensors and the light subsystem-side sensors may result in a condition that causes the device 100 to indicate that it is in need of maintenance. In an embodiment, where the difference is greater than a specific safety threshold, the device 100 may fail to continue to emit light events. In an embodiment, the information reported by these sensors may be stored with the usage statistics.

In an embodiment, where the light path 132 is completely or partially detachable from the probe 102, the detachable portion of the light path may have its own unique identifier. Where the detachable portion of the light path has its own unique identifier, usage statistics that relate to that portion of the light path may be maintained in much the same manner as the usage statistics for the probe but associated with the light path or portion.

One use of the device 100 is performing imaging examinations on humans for breast cancer detection. A device 100 may be a multimodality system incorporating optoacoustic imaging capability and ultrasound imaging capability. An advantage of optoacoustic imaging over ultrasound imaging alone is that it provides very high contrast images which may provide for the direct functional evaluation of tumors.

Figure 6:
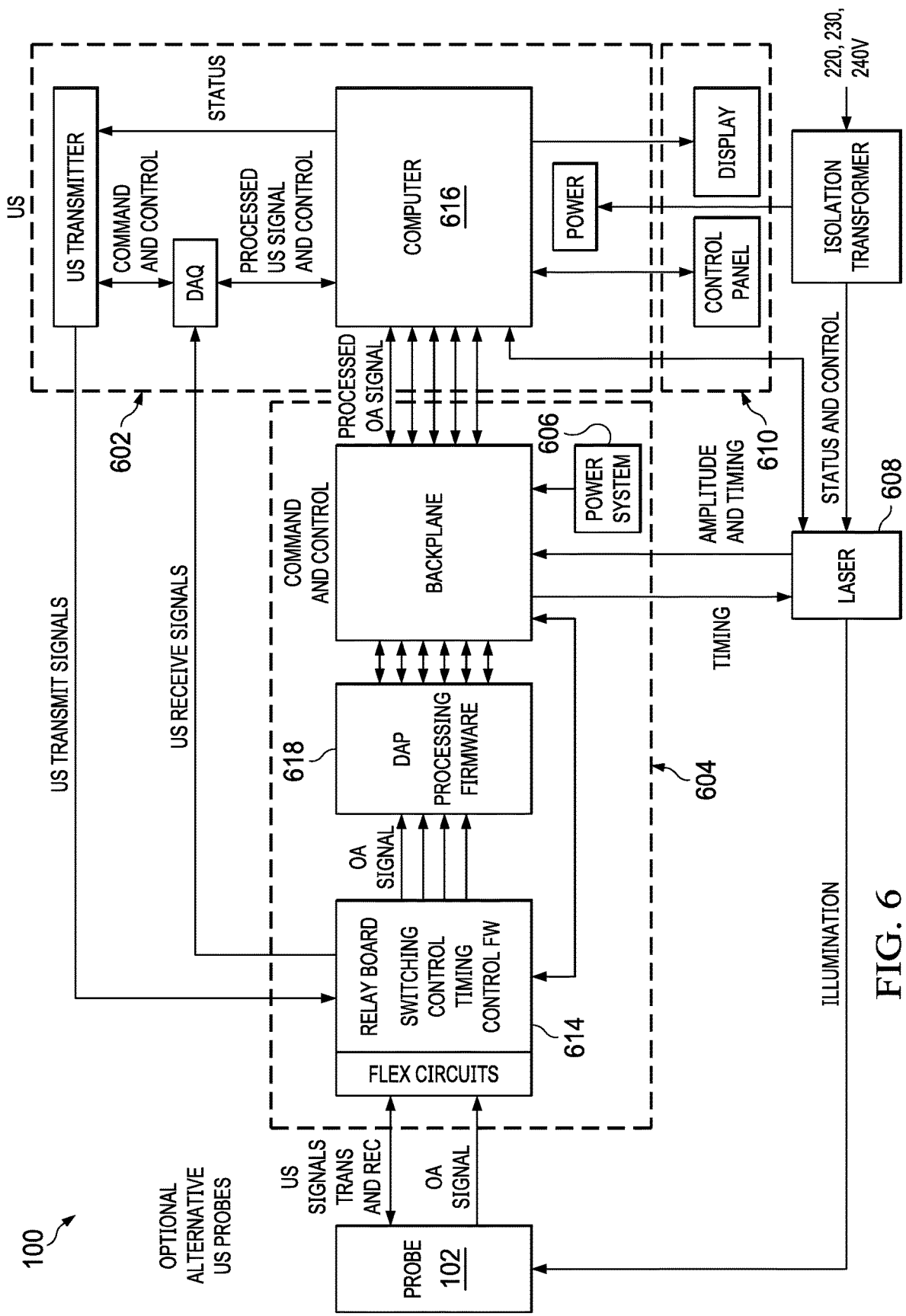
FIG. 6 shows a schematic block diagram illustrating hardware components of the system.

A block diagram of an embodiment of the clinical system is shown in FIG. 6 that illustrates the interaction between major subsystems and the type of signals they represent. In an embodiment, device 100 provides an integrated system consisting of the following subsystems: ultrasound subsystem 602, optoacoustic electronics subsystem 604, power supply subsystem 606, probe 102 and illumination/laser subsystem 608, which may be housed in one console, and the control and display subsystem 610 that can be attached to a console. The ultrasound subsystem 602, the optoacoustic electronics subsystem 604 and the control & display subsystem 610 will be referred to hereinafter collectively as the UOA.

The ultrasound subsystem 602 may be, e.g., a fully functional stand-alone ultrasound system. The ultrasound subsystem 602 includes an ultrasound transmitter 612 that outputs an ultrasound signal that is used to stimulate tissue. The ultrasound transmitter 612 provides its output to a relay board 614 in the optoacoustic electronics subsystem 604 which switches the ultrasound signal to the probe 102. The ultrasound subsystem further includes a data acquisition board, or DAQ, that receives ultrasound signals from the relay board 614 and processes them for transmission to and further processing by a computer 616. The computer 616 provides signal processing, user interface, and command and control functionality through software. The computer 616 includes one or more computer-readable medium for storage of programming as well as data generated by the system. The computer-readable medium may be in the form of volatile and/or non-volatile RAM, ROM, solid state drive, optical media, magnetic media (e.g., hard drive) or other storage device. The memory and storage may be integrated into or physically separate from the remaining components of the computer. The computer 616 further receives and transmits command and control signals to the DAQ for control of the data acquisition process and the ultrasound transmitter.

The optoacoustic electronics subsystem 284 includes a relay board 614 that provides switching functionality for alternately switching received ultrasound signals to the DAQ of the ultrasound subsystem 602 and received optoacoustic signals to a digital acquisition and processing (DAP) board 618. The relay board 614 includes firmware for both switching control and timing control. In an embodiment, flex circuits that form ultrasound transducers for both transmitting and receiving ultrasound signals are integrated into the relay board 614. The DAP 618 receives and processes the OA signal and outputs processed OA signals to the computer 616. The computer 616 provides command and control signals via a backplane to the DAP 618 and the relay board 614 and provides timing signals via the backplane to the illumination/laser subsystem 608.

In an embodiment, the device 100 uses a probe 102 including an array of transducers and an opening through which laser light can pass. In use, an operator manipulates controls and views the display as they move the probe 102 over the body or other volume to identify critical image characteristics. In an ultrasound mode the laser light source has no emission. In an optoacoustic mode the laser emits light according to specific preconfigured and/or operator set up parameters. In an embodiment, the hand-held probe may be manipulated in a similar fashion to the manipulation of an ultrasound probe. In an embodiment, the device 100 includes an operator selectable operational mode whereby an optoacoustic mode and ultrasound mode are interlaced.

In an embodiment, the device 100 includes an illumination source capable of providing two output wavelengths according to specific preconfigured and/or operator set up parameters. In an embodiment, the operator will be able to select either a neodymium-doped yttrium aluminum garnet or Nd:YAG laser output at 1064 nm or an Alexandrite laser output at 757 nm, or to select the use of both laser outputs. When two wavelengths are selected, the laser subsystem, according to specific preconfigured and/or operator set up parameters, may alternate between the two wavelengths one after the other, or in other preconfigured or operator set up cycles. In an embodiment, laser operating parameters such as energy, pulse rate, and wavelength will be operator selectable, and subject, however, to specific preconfigured parameters.

In an embodiment, communication of the laser energy will be via a fiber optic bundle with a detachable mechanism. The detachable mechanism for interfacing the laser output to the fiber optic bundle includes a safety interlock/ laser shutdown if disconnected. In an embodiment, the laser subsystem components include heat exchangers; pulse drivers; direct laser controls; laser power supplies; laser power management; laser head(s), cavities and optics; control and drive electronics; electronic interface ports; and a laser output port.

In an embodiment, the laser is completely controlled by the UOA control system. The clinical device may be powered ON/OFF by the use of a low current key switch located near the user control panel. Through the action of this low current switch, closure will cause the secondary output of a 230 VAC isolation transformer to be applied to each of the subsystems, including the laser. Opening this switch removes power from each of the subsystems.

In an embodiment, the laser subsystem consists of a Q-Switched Nd:YAG laser and an Alexandrite Q-Switched laser with a common concentric output connector designed to have a fiber optic bundle attached. It contains all necessary electronics, cooling, power management, optics, and connections necessary to meet operational requirements.

As discussed above, according to specific preconfigured parameters, in an embodiment, the operator will be able to select the device 100 laser light output from the Nd:YAG (1064 nm) only or select laser light output from the Alexandrite (757 nm) only or alternating the laser light output of both wavelengths. In an embodiment, selection will be accomplished via RS232 commands from the UOA.

In an embodiment, the time between wavelength changes will preferably be less than 0.05 seconds, and the time delay to initiate the response to a wavelength change shall be less than 0.01 seconds (which is included in the 0.05 seconds to change wavelengths). This would allow a command to be 0.01 seconds before the actual wavelength change is made. These timing parameters will permit the device 100 to be capable of alternating the wavelength output at a rate up to 20 times per second so as to interleave each separate wavelength operating at 10 pulses per second.

In an embodiment, the laser output pulse width for the Nd:YAG laser is approximately 7 ns but as long as practical, and in any case should be less than 25 ns for the best pulse stability. The laser output pulse width for the Alexandrite laser may be less than approximately 60 ns and more preferably less than approximately 50 ns. In an embodiment, no satellite pulse (a secondary laser pulse occurring shortly after the primary pulse) is allowed for either laser. As discussed above, in an embodiment, one or more light sources other than the Nd:YAG or Alexandrite lasers may be employed. Thus, for example, in an embodiment, one quickly tunable laser could be deployed to create two or more separate wavelengths in sequential light pulses during operation of the device.

The pulse rate may be operator selectable. In an embodiment, the pulse rate is operator selectable from 2, 5, 10 PPS for each wavelength, and when interlace is selected the pulse rate will double to 4, 10, 20 PPS. In an embodiment, the maximum time to select between pulse rates will be 10 seconds. The pulse rate for each laser wavelength will be independent of single wavelength or interlace operation.

In an embodiment, the energy per pulse (laser output) that will be directed into the fiber bundle will be variable between 25 mJ to 250 mJ in a minimum of 15 steps for each wavelength. In an embodiment, the control will be via the RS232 port. Energy per pulse will be independently adjustable for each wavelength. In an embodiment, the maximum time for the output energy to be affected post selection will be approximately 2 seconds.

It is desirable to minimize the unintended pulse-to-pulse variation. Accordingly, in an embodiment, the (uncontrolled) pulse-to-pulse energy variation will be less than 3% RMS from the output of either laser after 50 laser pulses.

In an embodiment, a measure of the output energy of each pulse (both wavelengths) will be made and will be communicated with an analog output pulse to the UOA. In an embodiment, the pulse will be a stretched representation of the optically detected pulse. The amplitude will be a representation of the energy of each output pulse. In an embodiment, the amplitude will be 0 to 5 V peak with 5V peak equal to the maximum energy expected. In an embodiment, the driver for these signals may be DC coupled throughout and drive a 1000 ohm termination with 0 to 5 Volts. In an embodiment, the pulse may be peak detected and stretched by at least 200 ns but the peak must occur before 2 us to permit, that at least two samples are captures, when employing a 6.8 MHz anti-aliasing filter at 20 M samples/sec. In an embodiment, a 20 M samples/sec sampling unit is located in the UOA electronics. Interface connectors may use BNC on the laser subsystem. The connector output can be provided on either a single BNC connector or a pair of BNC connectors, In an embodiment, each rising edge of the laser pulses will be detected and communicated to the UOA in a TTL format over a coax cable with a BNC connector. In an embodiment, separate signals, coax cables and connector may be used for each additional wavelength. In an embodiment, the signal will be a positive going TTL signal that will have a duration of at least 1 microsecond. In an embodiment, the UOA termination will be AC coupled into 50 ohms.

In an embodiment, there will be a sync pulse jitter test. The test may use an oscilloscope with the trigger using the TTL sync pulse. The input will be the output of a wideband optical test detector that is sampling the output of the laser pulse. The RMS jitter of the optical detected waveform is preferably less than about 6 ns.

In an embodiment, each detected optical pulse for each wavelength is made available at two test connectors external to the laser system. In an embodiment, the test connectors will be BNC connectors, and the drivers for the signals should be able to drive a 50 ohm scope load. These test signals may be used to support system testing and evaluation. In an embodiment, there is a separate output for each wavelength from the sync detectors to an analog driver for a 50 ohms output load—the amplitude can be a percentage of the actual pulse out of the optical detector.

In an embodiment, a fiber optical bundle interfaces to the output of the combined laser output port. In an embodiment, the optical output will be horizontal at the front-right of the optical unit. A quick disconnect connector may to be used to connect the fiber bundle to the laser output port.

In an embodiment, the mount for the fiber cable provides self-alignment to the laser energy output. In an embodiment, a ceramic disk with a 6 mm centered aperture will be installed at the output of the fiber optic mount to minimize damage to the fiber bundle. In embodiment, a micro switch is engaged when the fiber bundle has made connection. The micro switch functions as a safety interlock and is used to ensure that the laser cannot be fired unless the micro switch is closed.

In an embodiment, the laser output beam shape will be circular. In an embodiment, the beam profile will be flattened to approximate a top hat shape to ensure homogeneous illumination of the optical fiber. In an embodiment, the beam width will be 6 mm in diameter at the 10% level. For safety and consistency, the beam shape should not substantially deviate from this shape; in an embodiment, the beam shape does not deviate from this shape by more than 3% RMS over time and from pulse-to-pulse.

In an embodiment, the output of each laser will be approximately 6.25 mm onto the fiber optics, and the beam should not have hot spot(s), including after extensive use. In an embodiment, both beam shapes (for the Nd:YAG and the Alexandrite) will be equal in diameter to within 5% of the 6 mm diameter. For the purposes herein, a hot spot is defined as a 15% variation in energy density over any 2 mm segment of the beam cross section. In an embodiment, the laser beam must be aimed at the output connector such that 98% of the output energy is transmitted into the fiber cable. In an embodiment, a mechanism is provided for achieving laser beam alignment in the field.

In an embodiment, the laser spectral width will be less than 30 nm at the Full Wave Half Maximum or FWHM level and the spectral characteristics are preferably stable and do not vary from pulse-to-pulse by more than 3 nm RMS.

In an embodiment, the major operating modes of the device 100 are:

a. Off mode: where all power has been turned off and no current should be flowing within the laser subsystem. This can be accomplished by turning OFF the main circuit breaker or by turning the power key switch to off. In this case power may still be connected to the isolation transformer.

b. Sleep mode or ultrasound only mode: Almost all power is shut down for all operations but with sufficient energy to place the laser subsystem into the "on" mode. For example only the laser control unit is power up.

c. On Mode: Warm Up Period: Places all necessary power ON to allow the laser to be warmed up. The laser will measure and report to the UOA the laser head temperature. Once the laser head temperature has reached a pre-determined value the UOA will place the laser system into the "standby mode". In an embodiment, the laser subsystem will not be allowed to go into the "standby mode" until sufficient warm up has occurred.

d. Standby Mode: Allows the laser to be placed into the "ready mode" quickly from a Ready Mode command.

e. Ready Mode: Places the laser into the emission mode but the shutter remains closed. In an embodiment, the emission mode can be started a pre-specified interval, e.g., within 1 second or after 20 pulses, after the emission mode command.

f. Emission mode: Provides specified output energy for as long as this mode is commanded. In this mode the laser provides for its lamp sync and driver, the Q-Switch delay and driver and the pulse rate as determined from external command. The wavelength output will be as determined from external command.

In an embodiment, the laser subsystem will have the capability to go from any operating mode to any lower operating mode directly: "off" being the lowest operating mode and "emission" being the highest operating mode. For example, in an embodiment, the operator will be able to go from the emission mode to the standby, on, sleep or off mode directly. Preferably, the operator will not be able to go from off to emission directly without first going through the modes between.

In an embodiment, the laser will operate with internal synchronism and the UOA will derive its synchronism from the laser via it sync signal outputs. In an embodiment, time sensitive interfaces (synchronism signals) will be interfaced using TTL signals, while computer interface information will be via RS232 interface. In an embodiment, the wavelength selection mode (single YAG, single ALEX, interlace mode) will be selected via RS232 and the control unit will produce the internal commands in interlace or single mode with the right timing. In an embodiment, electronics will validate the present laser emission thru energy photodiode and/or sync pulses and/or Q-Switch TTL sync outputs.

In an embodiment, a shutter will open to allow laser light to be emitted (defined as the emission mode). In an embodiment, the shutter will remain closed unless two conditions exist—a foot switch closure and an RS-232 command. But, as long as the foot switch remains closed and an RS232 command exists the emission will exist. Both the foot switch closure and the RS232 must both be present to achieve emissions. The foot switch closure may provide within the switch a double contact, NC and NO using a three-wire interface. When either or both the foot switch and RS232 command is changed emission will cease to exist via a closure of the shutter, preferably within about 0.5 seconds. The laser subsystem may remain in the Ready mode until commanded otherwise.

In an embodiment, the laser operating system shall keep a non-volatile time-stamped record of error codes, of lamp shots, and operational events, for the purpose of accountability and troubleshooting. The non-volatile record may be readable, and possibly erasable, via RS-232 commands. In an embodiment, erasure of the non-volatile record requires a password or other access device. In an embodiment, a log consisting of not less than 50 events may be sufficient. In an embodiment, the UOA can poll the number of messages and read them.

In an embodiment, the laser subsystem will monitor the temperature of the lasers heads and report each to the UOA on a periodic basis, permitting the UOA to avoid instructing the laser to go into the Ready Mode unless the laser head has reached an acceptable temperature, and automatically placing the laser subsystem into the off mode if the temperature is unexpectedly outside of its appropriate operating range.

In an embodiment, wires to pockets cell and all internal high radiated signals should be shielded. To mitigate electromagnetic radiation during the imaging time of the device 100, the lamp driver recharging should be delayed by more than 70 microseconds after the Q-Switch. During recharge the electromagnetic radiation must be sufficiently low so as not to interfere with ultrasound or OA imaging.

In an alternative embodiment, a control signal can be used to suppress power supply switching noise during OA data acquisition, and also during US data acquisition. For example, a TTL trigger from within the laser circuitry may be generated such that a logic HIGH would cause the internal switching power supply to stop its internal oscillator that drives the switching PWM (pulse width modulation) circuitry that powers the flash lamp circuits, and/or any other switching operation, and when at a logic LOW would resume normal operation. In an embodiment, this control may not be asserted for more than certain ON time (e.g., 100 microseconds), and to not exceed a certain duty cycle. In an embodiment, a trigger signal could be negative logic wherein a logic LOW would stop the oscillator and a logic HIGH would allow it to resume. In an embodiment, the trigger signal can be applied to one or more other switching power supplies within the laser and/or elsewhere in the OA system, which may suppress electrical noise from the power supply during the non-oscillatory interval. In an embodiment, the data acquisition period should be within the interval during which the one or more switching power supplies have the switching circuitry inhibited. Even where a switching power supply is of a type that is not PWM controlled, the trigger can in any event be used to inhibit operation of the internal oscillator used to control the switching functions.

Out-of-Plane Artifacts

Referring back to FIG. 5A, the probe 102 provides two optical beams emerging from the two optical windows 303 which illuminate a tissue site 510 through the epidermis or skin 515 of the tissue site 510. The two optical beams merge and are scattered by the skin 515 and the tissue site 510 to form a pattern of scattered light 520. As indicated above, the electromagnetic energy illuminating the tissue site may be absorbed or reflected by tissue structures such as, for example, a tissue structure 525, which generates acoustic energy waves such as, for example, acoustic waves 530, that propagate through the tissue site 510. A portion of the acoustic waves 530 impinge upon the acoustic lens 305 to the transducer 410 and are converted to electrical acoustic signals that are stored and processed as described above. In one embodiment, the optical beams exiting through the optical windows 303 impinge on the skin 515 from both sides of the transducer 410. In another embodiment, the optical beams preferably enter the skin 515 as close to each other as possible to form as much of the pattern of scattered light 520 as possible directly underneath the transducer 410. Positioning the optical beams as close as possible provides maximum fluence in an image plane extending from the transducer 410 into the tissue site 510.

The term "image plane" may broadly refer to a two-dimensional image or region generated for visualizing a thin tissue slice when the probe 102 is positioned adjacent the skin 515 of the tissue site 510 with the image extending into the depths of the tissue site on a Y-axis 570 directly under the array of transducers 410 in a direction generally orthogonal to the surface of the transducer 410. In the embodiment shown in FIG. 5A, a cross section of an image plane is illustrated by a dashed line 545. Referring to FIG. 5B, a sectional view along the longitudinal length of the transducer 410 is shown comprising a plurality of transducer elements 550 forming a transducer array 555 wherein the transducers elements 550 are aligned on an X-axis parallel to the transducer array 555. In an embodiment, the image plane may be image plane 560 extending into the depths of the tissue from an X-axis 565 directly under the transducer array 555 at a specific time that is used to visualize a thin tissue slice as described above. In this embodiment, the cross-section of the image plane 560 is shown in FIG. 5A as the dashed line 545.

A tissue structure may be described as being an "in-plane" or "out-of-plane" tissue structure depending on its location with respect to the image plane itself when the probe 102 is located at a specific position on the skin 515 with a specific orientation to the skin 515. In one embodiment, the tissue structure 525 may be referred to as an in-plane tissue structure when the tissue structure 525 intersects the image plane 525 as shown in both FIGS. 5A and 5B. In another embodiment, a tissue structure may be referred to as an out-of-plane tissue structure such as, for example, tissue structure 535 when the tissue structure does not intersect the image plane 560 as shown with reference to the cross-section of the image plane in FIG. 5A. Because the out-of-plane tissue structure 535 does not intersect the image plane 560, the tissue structure 535 does not appear in the image plane 560 itself and, as such, is not shown in FIG. 5B. Regardless of whether a tissue structure is characterized as an "in-plane" or "out-of-plane" tissue structure during a specific light event at a specific point in time, both will generate acoustic energy waves when illuminated. For example, the tissue structure 535 also generates acoustic energy waves such as, for example, out-of-plane acoustic energy waves 540 that propagate through the tissue site 510, a portion of which impinge upon the acoustic lens 305 to the transducer 410 along with the portion of the acoustic waves 530 generated by the in-plane tissue structure 525.

Because biological tissue scatters impinging light in many directions, the scattered light 520 is not confined to a specific image plane such as, for example, the image plane 560. Moreover, the geometric arrangement of the optical components of the optoacoustic system such as, for example, the optical windows 303 and the transducer 410, may also illuminate out-of-plane tissue structures which generate undesired acoustic energy waves. Thus, such out-of-plane tissue structures and geometric anomalies can produce acoustic energy waves that are undesired and interfere with the desired acoustic energy waves generated by a tissue structure of interest such as, for example, a malignant tumor. Consequently, these undesired acoustic energy waves produce unwanted out-of-plane artifacts in an image plane such as, for example, the image plane 560 in FIG. 5B.

(a) Suppressing Out-of-Plane Artifact Using Higher Dimensional Array

As indicated above, the transducer array may have transducer elements arranged in different geometries such as, for example, the linear transducer array 555 wherein the transducer elements are arranged in a line and nonlinear transducer arrays which includes multiple row arrays also known as 1.5 dimensional arrays. Nonlinear transducer arrays permit additional angles from which to resolve the optical return signals from a given voxel within the tissue site. Using nonlinear transducer arrays may improve resolution and/or add clarity and contrast to the image because higher dimensional transducer arrays can collect more information about the voxels within the tissue site. This conditional information helps identify and localize the out-of-plane artifacts generated by the out-of-plane tissue structures, such as tissue structure 535, so that the optoacoustic signals resulting from the optoacoustic response can be suppressed or canceled.

For example, in an embodiment, the probe 102 may include a 1.25D, 1.5D, 1.75D or 2D nonlinear transducer array of elements rather than a linear transducer array, i.e., a 1D transducer array. The 1.25D, 1.5D, or 1.75D arrays comprise several rows of 1D transducer elements, each connected in different corresponding electrical configurations. When the transducer elements are not confined to a single 1D line configuration, the recorded data provides more information about the location of the out-of-plane tissue structures in relation to the imaging plane such as the out-of-plane tissue structure 535 shown in FIG. 5A. Because more information is available to better localize the out-of-plane tissue structure 535, the ability of the processing systems to suppress undesired optoacoustic signals from the out-of-plane tissue structure 535 is enhanced.

For example, in an embodiment, a probe 102 with a 2D array of elements (e.g. with elements populated on a fine grid) may be used to determine relative bearings of acoustic energy waves that propagate through the tissue site 510 and impinge upon the plurality of transducer elements comprising 2D array of elements. These acoustic energy waves may be generated by an "in-plane" 525 or "out-of-plane" 535 structure during a specific light event at a specific point in time as disclosed herein. Referring again to FIG. 5B, a sectional view along the longitudinal length of the transducer 410 is shown comprising a plurality of transducer elements 550, wherein the transducer elements are aligned along the X-axis. In a 2D array the transducer 410 may further include rows of transducer elements 550 (not shown), wherein the rows of transducer elements 550 are aligned along the Z-axis, thereby forming a grid of transducer elements 550. In an embodiment, the rows of transducer elements 550 aligned along the Z-axis may be parallel.

A bearing may be determined for each of the acoustic waves impinging upon the 2D array based upon, at least in part, an analysis of the measured signal strength at each transducer element 550, the speed of sound in tissue, the relative spacing of the transducer elements 550 and the time interval between the acoustic wave impinging upon each of the plurality of transducer elements 550 comprising the 2D array. For example, if an acoustic wave is incident upon two transducer elements other than perpendicular to the axis of the two transducer elements, the acoustic wave will have to travel some distance Ad further in order to reach one of the two transducer elements 550. Having determined the distance Ad the angle of incident may be calculated. In a 2D array comprising a plurality of transducer elements aligned along the X-axis and the Z-axis a bearing may be established for each of the acoustic waves impinging upon the transducer 410. The bearing may be used to determine whether the acoustic wave energy originated from an "in-plane" 525 or an "out-of-plane" 535 structure, wherein an optoacoustic signal resulting from out-of-plane structure may be suppressed or canceled.

In an embodiment, a 2D array of elements (e.g. with elements populated on a fine grid) may perform well but may be large and can require a high number of electrical connections that would need to be sampled. Furthermore, with fixed arrays of only several rows of elements (e.g. five closely spaced rows of elements), the separation between the first row and the last row may be insufficient to localize out-of-plane sources, especially for large objects and/or structures which comprise low frequency signal content (e.g., below 1 MHz) in optoacoustics. This is because signals generated by light absorbed by an object involving a short optical pulse (e.g. 10 ns pulse width) produce a very broad frequency content. In certain circumstances, higher frequency signal content can be better localized with a smaller separation between first row and last row compared to lower frequency signal content which would require a larger separation to localize. In certain circumstances, characterizing system spatial resolution performance involves using high-frequency producing (e.g. small) targets; however, design objectives to remove out-of-plane signal are different from design objectives to improve spatial resolution.

The present system and methods are described above with reference to block diagrams and operational illustrations of methods and devices comprising an optoacoustic probe. It is understood that each block of the block diagrams or operational illustrations, and combinations of blocks in the block diagrams or operational illustrations, may be implemented by means of analog or digital hardware and computer program instructions. These computer program instructions may be provided to a processor of a general purpose computer, special purpose computer, ASIC, FPGA or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

As used in this description and in the following claims, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds.

As used in this specification and the appended claims, the term "or" is generally employed in its sense including "and/or" unless the content clearly dictates otherwise.

The recitation herein of numerical ranges by endpoints includes all numbers subsumed within that range (e.g. 1 to 5 includes 1, 1.5, 2, 2.75, 3, 3.80, 4, and 5).

Unless otherwise indicated, all numbers expressing quantities of ingredients, measurement of properties and so forth used in the specification and claims are to be understood as being modified in all instances by the term "about," unless the context clearly dictates otherwise. Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the scope of the claims, each numerical parameter should at least be construed in light of the number of reported significant digits and by applying ordinary rounding techniques. Any numerical value, however, inherently contains certain errors necessarily resulting from the standard deviations found in their respective testing measurements.

Those skilled in the art will recognize that the methods and systems of the present disclosure may be implemented in many manners and as such are not to be limited by the foregoing example embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

Various modifications and alterations to the invention will become apparent to those skilled in the art without departing from the scope and spirit of this invention. It should be understood that the invention is not intended to be unduly limited by the specific embodiments and examples set forth herein, and that such embodiments and examples are presented merely to illustrate the invention, with the scope of the invention intended to be limited only by the claims attached hereto. Thus, while the invention has been particularly shown and described with reference to a preferred embodiment thereof, it will be understood by those skilled in the art that various changes in form and details may be made therein without departing from the spirit and scope of the invention.

What is claimed is:

1. An optoacoustic probe for optoacoustic imaging of a tissue, the probe having a distal end operable to contact the tissue and a proximal end, the probe comprising:
   a transducer assembly configured to receive optoacoustic return signals;
   an optical window configured to carry light along a light path to the tissue; and
   a housing comprising:
      (i) a distal portion having a probe face that includes an acoustic opening into which the transducer assembly is disposed and an optical opening into which the optical window is disposed, the transducer assembly and the optical window extending proximally from the probe face; and
      (ii) a gasket disposed within the optical opening at the probe face and engaging and extending around the optical window, the gasket configured to form an optoacoustic barrier to optically and acoustically isolate a portion of the optical window from the housing of the probe.

2. The optoacoustic probe of claim 1, wherein the transducer assembly comprises an acoustic lens in acoustic communication with an acoustic transducer, the acoustic lens having a distal face and a proximal end, the distal face being adjacent to the probe face, and the proximal end being adjacent the acoustic transducer, wherein the gasket is positioned between the optical window and the acoustic lens.

3. The optoacoustic probe of claim 1, wherein the housing is made from an optically reflective material that comprises at least one of acrylonitrile-butadiene styrene or polybutylene terephthalate.

4. The optoacoustic probe of claim 1, wherein the gasket comprises a crystal structure having anisotropic thermal expansion properties that form the optoacoustic barrier by constrain generation of acoustic waves from stray light within the gasket, thereby constraining propagation of acoustic waves from the gasket to the housing.

5. The optoacoustic probe of claim 4, wherein the gasket comprises silicone embedded with the crystalline structure, the crystalline structure comprising at least one of i) titanium dioxide or ii) boron nitride, at a level of from 1% to 15% by weight of the gasket to provide the at least partial optical isolation.

6. The optoacoustic probe of claim 4, wherein the gasket comprises silicone embedded with microspheres at a level of from 2% to 25% by weight of the gasket to provide the at least partial acoustic isolation.

* * * * *